(12) United States Patent
Wang et al.

(10) Patent No.: US 9,226,923 B2
(45) Date of Patent: Jan. 5, 2016

(54) SPIROCYCLIC MOLECULES AS PROTEIN KINASE INHIBITORS

(75) Inventors: Zhaoyin Wang, Kirkland (CA); Lianhai Li, Pierrefonds (CA); Zhigang Wang, Lachine (CA)

(73) Assignee: Nanjing Allgen Pharma Co. Ltd., Nanjing (CN)

( * ) Notice: Subject to any disclaimer, the term of this patent is extended or adjusted under 35 U.S.C. 154(b) by 0 days.

(21) Appl. No.: 14/234,586

(22) PCT Filed: Jul. 26, 2012

(86) PCT No.: PCT/CA2012/000709
§ 371 (c)(1),
(2), (4) Date: Apr. 14, 2014

(87) PCT Pub. No.: WO2013/013308
PCT Pub. Date: Jan. 31, 2013

(65) Prior Publication Data
US 2014/0243303 A1    Aug. 28, 2014

Related U.S. Application Data

(60) Provisional application No. 61/457,980, filed on Jul. 27, 2011.

(51) Int. Cl.
*C07D 401/14* (2006.01)
*A61K 31/4439* (2006.01)
*A61K 45/06* (2006.01)

(52) U.S. Cl.
CPC ............. *A61K 31/4439* (2013.01); *A61K 45/06* (2013.01); *C07D 401/14* (2013.01)

(58) Field of Classification Search
CPC ........................... C07D 401/04; C07D 417/12
USPC ............................................ 546/275.4, 269.7
See application file for complete search history.

(56) References Cited

U.S. PATENT DOCUMENTS 6,603,008 B1 *  8/2003  Ando et al. ................ 546/269.7

FOREIGN PATENT DOCUMENTS

CA      2577937 A1      3/2006
WO    2010135524    *  11/2010   ........... C07D 413/04

OTHER PUBLICATIONS

International Search Report corresponding to PCT/CA2012/000709 dated Oct. 10, 2012 (5 pages).

* cited by examiner

*Primary Examiner* — Noble Jarrell
(74) *Attorney, Agent, or Firm* — Kilpatrick, Townsend & Stockton LLP

(57) ABSTRACT

The present invention relates to spirocyclic compounds of formula I, namely spirocyclic (1H-pyrazol-4-yl)-3-(1-(2,6-dichloro-3-fluorophenyl)ethoxy)pyridin-2-amines having protein kinase inhibitory activity, and methods of synthesizing and using such compounds. Preferred compounds are c-Met and/or ALK inhibitors useful for the treatment of abnormal cell growth, such as cancers.

(I)

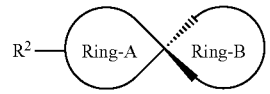

$R^2$ is selected from

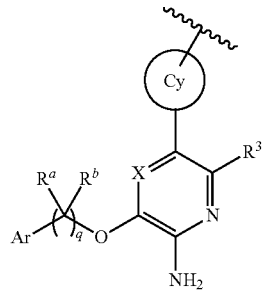

10 Claims, No Drawings

SPIROCYCLIC MOLECULES AS PROTEIN KINASE INHIBITORS

CROSS-REFERENCE TO RELATED APPLICATIONS

This application claims priority of U.S. provisional patent application 61/457,980, filed on Jul. 27, 2011, the specification of which is hereby incorporated by reference.

BACKGROUND (a) Field

The invention relates generally to novel chemical compounds and methods. More particularly, the invention provides novel spirocyclic molecules, having protein tyrosine kinase inhibitory activity, and methods of synthesizing and using such compounds. Preferred compounds are c-Met and/or ALK inhibitors useful for the treatment of abnormal cell growth, such as cancers.

(b) Related Prior Art

The protein kinases represent a large family of proteins which play a central role in the regulation of a wide variety of cellular processes and maintain control over cellular function. A partial, non limiting, list of such kinases includes ALK, abl, Akt, bcr-abl, Blk, Brk, c-kit, c-met, c-src, CDKl, CDK2, CDK3, CDK4, CDK5, CDK6, CDK7, CDK8, CDK9, CDKIO, bRaf, cRafl, CSK, EGFR, ErbB2, ErbB3, ErbB4, Erk, Pak, fes, FGFRI, FGFR2, FGFR3, FGFR4, FGFR5, Fgr, flt-1, flt-3, Fps, Frk, Fyn, Hck, IGF-IR, INS-R, Jakl, Jak2, Jak3, KDR, Lck, Lyn, FAK, MEK, p38, PDGFR, PDC, PKC, PYK2, ros, tie, tie2, Pim-1, P13k, TRK and Zap70. Abnormal protein kinase activity has been related to several disorders, ranging from non-life threatening diseases such as psoriasis to extremely serious diseases such as cancers.

This invention concerns a new family of novel spirocyclic compounds that are c-Met and/or ALK inhibitors and their use in treating cancers and other diseases. Unexpectedly, the novel spirocyclic compounds of the present invention exhibit improved inhibitory activity against ALK mutant enzymes that are more resistant to Crizotinib, therefore may provide a more effective treatment for diseases caused by abnormality of ALK enzyme.

SUMMARY

According to an embodiment, there is provided a compound of Formula I

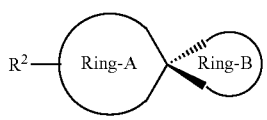

(I)

or a pharmaceutically acceptable salt, hydrate or solvate thereof, wherein:
Ring A may be a 3 to 12 membered carbocyclic ring, or is a 3 to 12 membered carbocyclic ring in which one or more carbon ring atoms may be replaced with one or more O, S, —C(O)—, —C(S)— and $NR^1$; and wherein the Ring A may be unsubstituted or substituted by one or more $R^c$;
Ring B may be a 3 to 12 membered carbocyclic ring, or may be a 3 to 12 membered carbocyclic ring in which one or more carbon ring atoms may be optionally replaced with one or more O, S, —C(O)—, —C(S)— and $NR^1$; and wherein the Ring B may be unsubstituted or substituted by one or more $R^c$;
$R^1$ may be independently chosen from hydrogen, $C_{1-12}$ alkyl, $C_{1-12}$ alkyl in which one carbon atom may be replaced with Si, O, S atom, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —S(O)$_m R^4$, —SO$_2 NR^4 R^5$, —S(O)$_2 OR^4$, —C(O)R$^4$, —NR$^4$C(O)R$^5$, —(CR$^6$R$^7$)$_n$C(O)OR$^4$, —(CR$^6$R$^7$)$_n$OR$^4$, —(CR$^6$R$^7$)$_n$C(O)NR$^4$R$^5$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, and wherein each hydrogen in $R^1$ may be unsubstituted or substituted by $R^c$, or one of the hydrogen in $R^1$ may be replaced with —P(O)(OR$^9$)$_2$—;
$R^c$ may be independently chosen from halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —S(O)$_m R^4$, —S(O)$_2 NR^4 R^5$, —S(O)$_2 OR^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$OR$^4$, —(CR$^6$R$^7$)$_n$C(O)NR$^4$R$^6$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, —NH$_2$, SF$_5$, —OH, —O—$C_{1-12}$alkyl, —O—(CH$_2$)$_n$$C_{3-12}$ cycloalkyl, —O—(CH$_2$)$_n$$C_{6-12}$ aryl, —O—(CH$_2$)$_n$(3-12 membered heteroalicyclic ring) or —O—(CH$_2$)$_n$(5-12 membered heteroaryl ring);
and wherein each hydrogen in $R^c$ may be unsubstituted or substituted by $R^8$, and wherein $R^c$ groups on adjacent atoms are uncombined or combine to form a $C_{6-12}$ aryl, 5-12 membered heteroaryl ring, $C_{3-12}$ cycloalkyl or 3-12 membered heteroalicyclic ring;
$R^2$ may be selected from

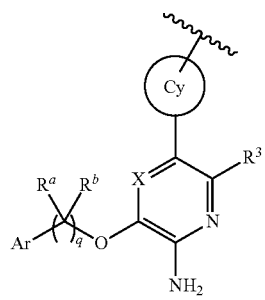

wherein:
X may be N or $CR^{12}$;
Ar may be $C_{6-12}$ aryl, 5-12 membered heteroaryl ring, $C_{3-12}$ cycloalkyl or 3-12 membered heteroalicyclic ring, and Ar may be unsubstituted or substituted by one or more $R^c$ groups;

may be selected from $C_{6-12}$ aryl, 5-12 membered heteroaryl ring, $C_{3-12}$ cycloalkyl or 3-12 membered heteroalicyclic ring, wherein

may be unsubstituted or substituted by one, two or three $R^c$ groups;

$R^3$ may be chosen from hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, $-S(O)_m R^4$, $-SO_2 NR^4 R^5$, $-S(O)_2 OR^4$, $SF_5$, $-NO_2$, $-NR^4 R^5$, $-(CR^6 R^7)_n OR^4$, $-CN$, $-C(O)R^4$, $-OC(O)R^4$, $-O(CR^6 R^7)_n R^4$, $-NR^4 C(O)R^5$, $-(CR^6 R^7)_n C(O)OR^4$, $-(CR^6 R^7)_n NCR^4 R^5$, $-C(=NR^6)NR^4 R^5$, $-NR^4 C(O)NR^5 R^6$, $-NR^4 S(O)_2 R^5$ or $-C(O)NR^4 R^5$, and each hydrogen in $R^3$ may be unsubstituted or substituted by $R^8$;

$R^4$, $R^5$, $R^6$ and $R^7$ are independently chosen from hydrogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring;

or any two of $R^4$, $R^5$, $R^6$ and $R^7$ bound to the same nitrogen atom, together with the nitrogen to which they are bound, may combine to form a 3 to 12 membered heteroalicyclic ring or a 5-12 membered heteroaryl ring or a 3 to 12 membered heteroalicyclic ring or a 5-12 membered heteroaryl ring containing 1 to 3 heteroatoms selected from N, O, and S;

or any two of $R^4$, $R^5$, $R^6$ and $R^7$ bound to the same carbon atom may combine to form a $C_{3-12}$ cycloalkyl, $C_{6-12}$ aryl, 3-12 membered heteroalicyclic or 5-12 membered heteroaryl ring;

and each hydrogen in $R^4$, $R^5$, $R^6$ and $R^7$ may be unsubstituted or substituted by $R^8$, or two hydrogen atoms on the same carbon atom in $R^4$, $R^5$, $R^6$ and $R^7$ may be unsubstituted or are an oxo substituent;

$R^8$ may be independently chosen from halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, $-NH_2$, $-CN$, $-OH$, $-O-C_{1-12}$alkyl, $-O-(CH_2)_n C_{3-12}$ cycloalkyl, $-O-(CH_2)_n C_{6-12}$ aryl, $-O-(CH_2)_n (3-12$ membered heteroalicyclic ring) or $-O-(CH_2)_n (5-12$ membered heteroaryl ring); and each hydrogen in $R^8$ may be unsubstituted or substituted by $R^{11}$;

$R^9$ may be independently chosen from a $C_{1-12}$ alkyl, aryl, heteroaryl which may be unsubstituted or substituted;

$R^{10}$ may be independently chosen from a $C_{1-12}$ alkyl which may be unsubstituted or substituted;

$R^{11}$ may be independently chosen from halogen, $C_{1-12}$ alkyl, $C_{1-12}$ alkoxy, $C_{3-12}$ cycloalkyl, $C_{6-12}$ aryl, 3-12 membered heteroalicyclic ring, 5-12 membered heteroaryl ring, $-O-C_{1-12}$ alkyl, $-O-(CH_2)_n C_{3-12}$ cycloalkyl, $-O-(CH_2)_n C_{6-12}$ aryl, $-O-(CH_2)_n (3-12$ membered heteroalicyclic ring), $-O-(CH_2)_n (5-12$ membered heteroaryl ring) or $-CN$, and each hydrogen in $R^{11}$ may be unsubstituted or substituted by halogen, $-OH$, $-CN$, $-C_{1-12}$ alkyl which may be unsubstituted, or partially halogenated or fully halogenated, $-O-C_{1-12}$ alkyl which may be unsubstituted or partially halogenated or fully halogenated, or substituted with $-C(O)-$;

$R^{12}$ may be chosen from hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, $-S(O)_m R^4$, $-SO_2 NR^4 R^5$, $-S(O)_2 OR^4$, $SF_5$, $-NO_2$, $-NR^4 R^5$, $-(CR^6 R^7)_n OR^4$, $-CN$, $-C(O)R^4$, $-OC(O)R^4$, $-O(CR^6 R^7)_n R^4$, $-NR^4 C(O)R^5$, $-(CR^6 R^7)_n C(O)OR^4$, $-(CR^6 R^7)_n NCR^4 R^5$, $-C(=NR^6)NR^4 R^5$, $-NR^4 C(O)NR^5 R^6$, $-NR^4 S(O)_2 R^5$ or $-C(O)NR^4 R^5$, and each hydrogen in $R^{12}$ may be unsubstituted or substituted by $R^3$;

$R^a$ and $R^b$ may be independently chosen from hydrogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, $-(CR^6 R^7)_n OR^4$, $-CN$, $-C(O)R^4$, $-(CR^6 R^7)_n C(O)OR^4$, $-(CR^6 R^7)_n NCR^4 R^5$ or $-C(O)NR^4 R^5$; and $R^a$ or $R^b$ are uncombined or, together with the carbon to which they may be attached to, $R^a$ and $R^b$ form a 3-12 membered ring or a 3-12 membered ring which contains one or more heteroatom chosen from $NR^4$, O, S, Si; or $R^a$ and $R^b$ may combine with a ring atom of Ar or a substituent of Ar to form a $C_{5-12}$ cycloalkyl, 5-12 membered heteroalicyclic ring fused to Ar; and each hydrogen in $R^a$ and $R^b$ may be unsubstituted or substituted by $R^c$;

each m may be independently 0, 1 or 2;

each n may be independently 0, 1, 2, 3 or 4;

q may be 1, 2, 3 or 4.

The

may be selected from

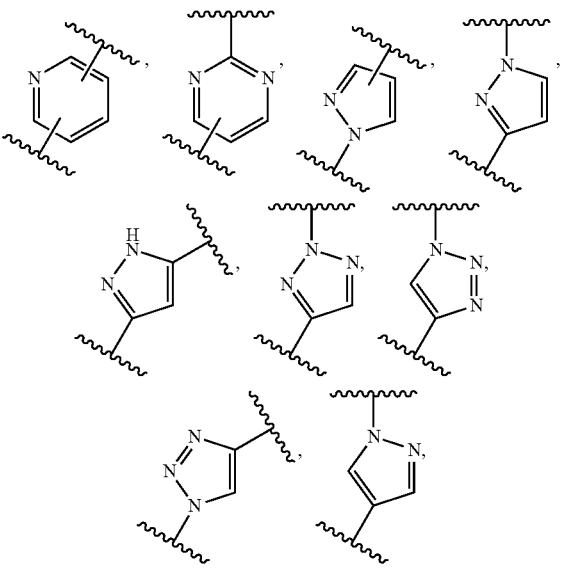

or an aryl, bicyclic aryl, bicyclic heteroaryl, unsubstituted or substituted by one, two or three $R^c$ groups as defined above.

The compound may be selected from:

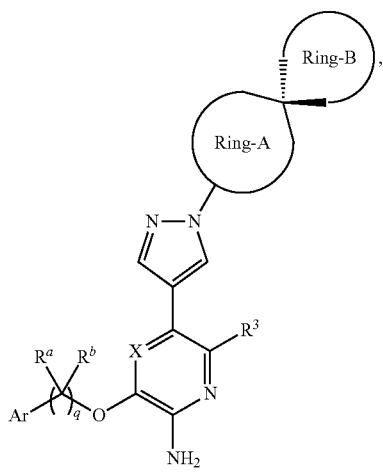

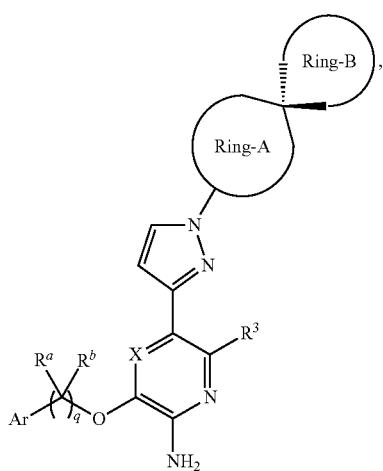

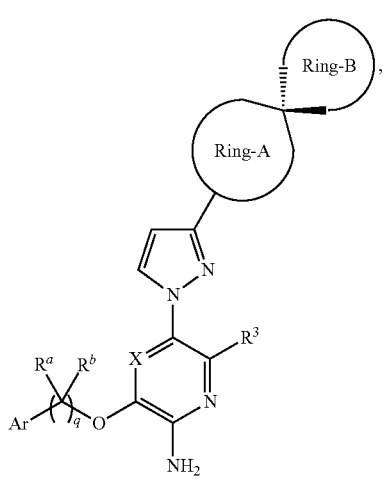

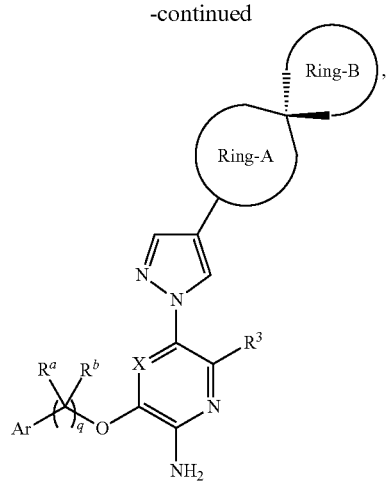

wherein:
Ring A may be a 3 to 12 membered carbocyclic ring or a 3 to 12 membered carbocyclic ring in which one or more carbon ring atoms may be replaced with one or more O, S, —C(O)—, —C(S)— and $NR^1$; and wherein the Ring A may be unsubstituted or substituted by one or more $R^c$;

Ring B may be a 3 to 12 membered carbocyclic ring or a 3 to 12 membered carbocyclic ring in which one or more carbon ring atoms may be replaced with one or more O, S, —C(O)—, —C(S)— and $NR^1$; and wherein the Ring B may be unsubstituted or substituted by one or more $R^c$;

$R^1$ may be independently chosen from hydrogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —S(O)$_m$R$^4$, —SO$_2$NR$^4$R$^5$, —S(O)$_2$OR$^4$, —C(O)R$^4$, —NR$^4$C(O)R$^5$, —(CR$^6$R$^7$)$_n$C(O)OR$^4$, —(CR$^6$R$^7$)$_n$OR$^4$, —(CR$^6$R$^7$)$_n$C(O)NR$^4$R$^5$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, and wherein each hydrogen in $R^1$ may be unsubstituted or substituted by $R^c$;

X may be N or $CR^{12}$;

Ar may be $C_{6-12}$ aryl, 5-12 membered heteroaryl ring, $C_{3-12}$ cycloalkyl or 3-12 membered heteroalicyclic ring, and wherein Ar may be unsubstituted or substituted by one or more $R^c$ groups;

$R^3$ may be chosen from hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —S(O)$_m$R$^4$, —SO$_2$NR$^4$R$^5$, —S(O)$_2$OR$^4$, SF$_5$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, and wherein each hydrogen in $R^3$ may be unsubstituted or substituted by $R^8$;

$R^c$ may be independently chosen from halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —S(O)$_m$R$^4$, —S(O)$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$OR$^4$, —(CR$^6$R$^7$)$_n$C(O)NR$^4$R$^5$, —(CR$^6$R$^7$)$_n$NCR$^4$R$^5$, —C(=NR$^6$)NR$^4$R$^5$, —NR$^4$C(O)

NR$^5$R$^6$, —NR$^4$S(O)$_2$R$^5$ or —C(O)NR$^4$R$^5$, —NH$_2$, SF$_5$, —OH, —O—C$_{1-12}$alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic ring) or —O—(CH$_2$)$_n$(5-12 membered heteroaryl ring);

and wherein each hydrogen in R$^c$ may be unsubstituted or substituted by R$^8$, and wherein R$^c$ groups on adjacent atoms are uncombined or combine to form a C$_{6-12}$ aryl, 5-12 membered heteroaryl ring, C$_{3-12}$ cycloalkyl or 3-12 membered heteroalicyclic ring;

R$^4$, R$^5$, R$^6$ and R$^7$ may be independently chosen from hydrogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic ring, 5-12 membered heteroaryl ring; or any two of R$^4$, R$^5$, R$^6$ and R$^7$ bound to the same nitrogen atom, together with the nitrogen to which they are bound, may combine to form a 3 to 12 membered heteroalicyclic ring or a 5-12 membered heteroaryl ring or a 3 to 12 membered heteroalicyclic ring or a 5-12 membered heteroaryl ring containing 1 to 3 heteroatoms selected from N, O, and S; or any two of R$^4$, R$^5$, R$^6$ and R$^7$ bound to the same carbon atom combine to form a C$_{3-12}$ cycloalkyl, C$_{6-12}$ aryl, 3-12 membered heteroalicyclic ring or 5-12 membered heteroaryl ring; and each hydrogen in R$^4$, R$^5$, R$^6$ and R$^7$ may be unsubstituted or substituted by R$^8$, or two hydrogen atoms on the same carbon atom in R$^4$, R$^5$, R$^6$ and R$^7$ may be unsubstituted or an oxo substituent;

R$^8$ may be independently chosen from halogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic ring, 5-12 membered heteroaryl ring, —NH$_2$, —CN, —OH, —O—C$_{1-12}$alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic ring) or —O—(CH$_2$)$_n$(5-12 membered heteroaryl ring); and each hydrogen in R$^8$ may be unsubstituted or substituted by R$^{11}$;

R$^{11}$ may be independently chosen from halogen, C$_{1-12}$ alkyl, C$_{1-12}$ alkoxy, C$_{3-12}$ cycloalkyl, C$_{6-12}$ aryl, 3-12 membered heteroalicyclic ring, 5-12 membered heteroaryl ring, —O—C$_{1-12}$ alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic ring), —O—(CH$_2$)$_n$(5-12 membered heteroaryl ring) or —CN, and each hydrogen in R$^{11}$ is unsubstituted or substituted by halogen, —OH, —CN, —C$_{1-12}$ alkyl which may be unsubstituted or partially halogenated or fully halogenated, —O—C$_{1-12}$ alkyl which may be unsubstituted or partially halogenated or fully halogenated, or substituted with —CO;

R$^{12}$ may be chosen from hydrogen, halogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic ring, 5-12 membered heteroaryl ring, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, and each hydrogen in R$^{12}$ may be unsubstituted or substituted by R$^3$;

R$^a$ and R$^b$ may be independently chosen from hydrogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic ring, 5-12 membered heteroaryl ring, —(CR$^6$R$^7$)$_n$OR$^4$, —CN, —C(O)R$^4$, —(CR$^6$R$^7$)$_n$C(O)OR$^4$, —(CR$^6$R$^7$)$_n$NCR$^4$R$^5$ or —C(O)NR$^4$R$^5$; and R$^a$ or R$^b$ are uncombined or, together with the carbon to which they may be attached to, R$^a$ and R$^b$ may form a 3-12 membered ring or a 3-12 membered ring which contains one or more heteroatom chosen from NR$^4$, O, S, Si; or R$^a$ and R$^b$ may combine with a ring atom of Ar or a substituent of Ar to form a C$_{6-12}$ cycloalkyl, 5-12 membered heteroalicyclic ring fused to Ar; and each hydrogen in R$^a$ and R$^b$ may be unsubstituted or substituted by R$^c$;

each m may be independently 0, 1 or 2;

each n may be independently 0, 1, 2, 3 or 4;

q may be 1, 2, 3 or 4;

or a pharmaceutically acceptable salt, hydrate or solvate thereof.

The compound may be selected from:

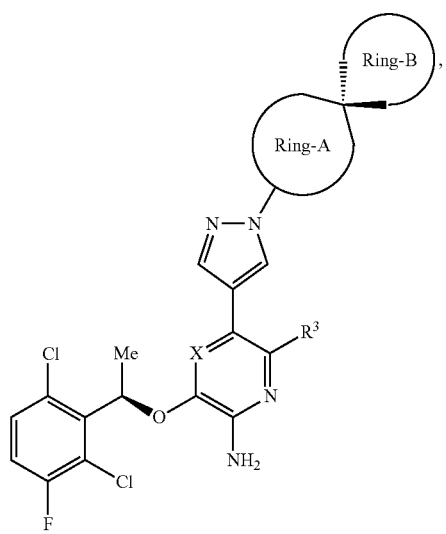

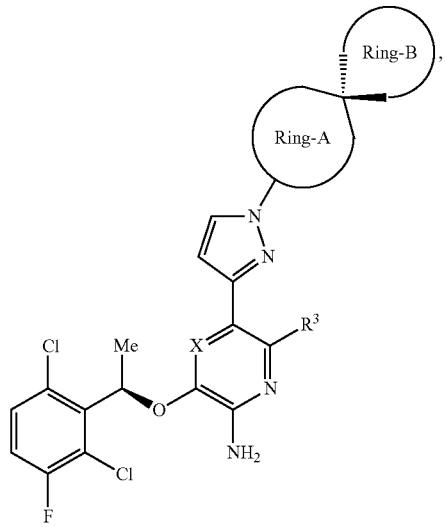

-continued
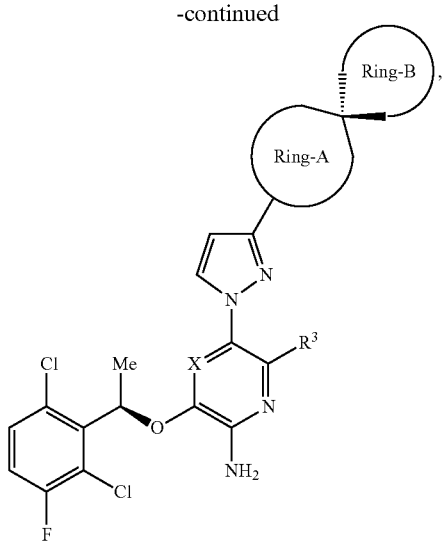
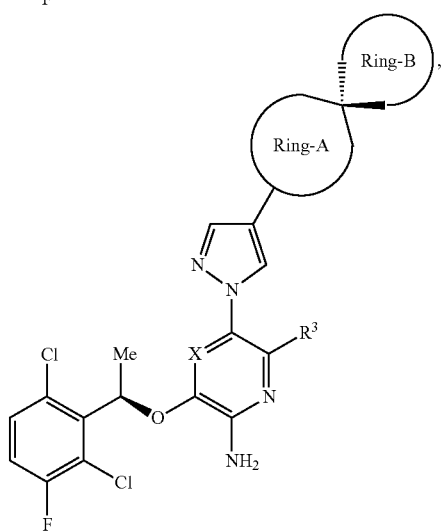
wherein X, Ring-A, Ring-B and $R^3$ may be as defined above.
The compound may be selected from:
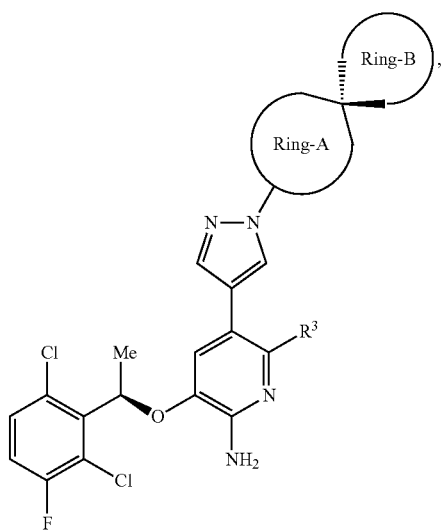
wherein $R^3$, Ring-A and Ring-B are defined as above.
The
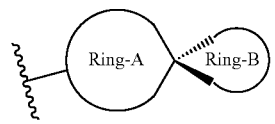
may be selected from the group consisting of:
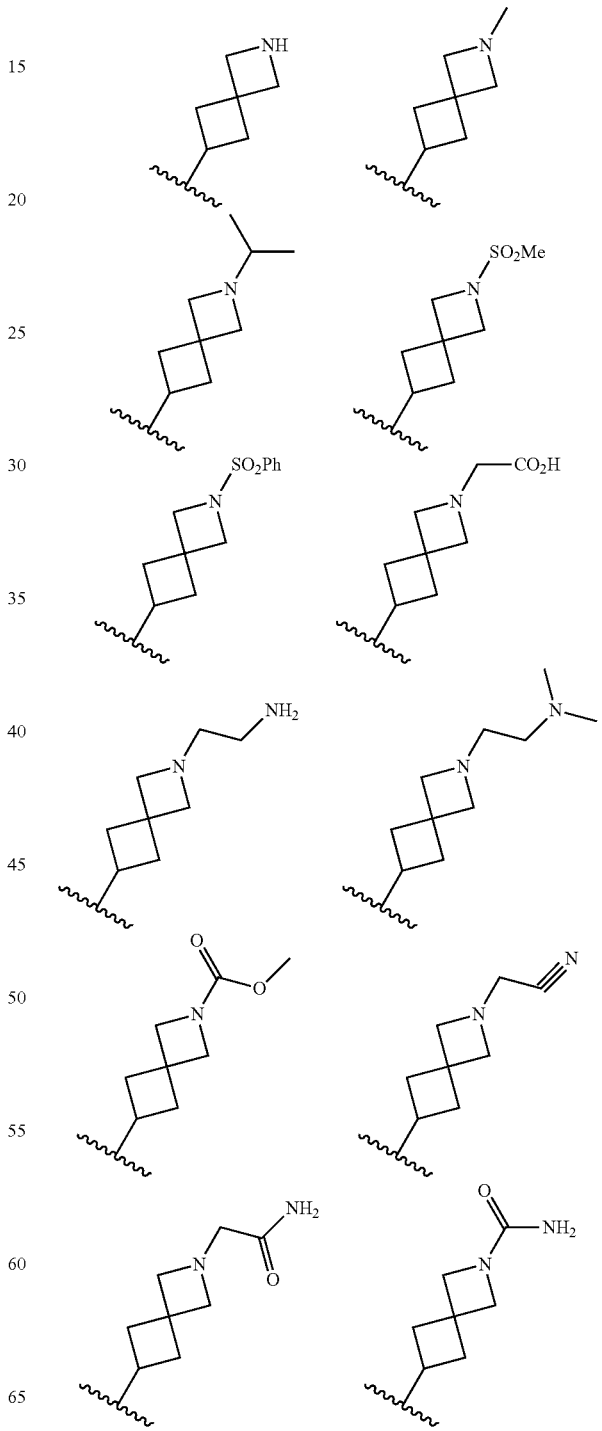

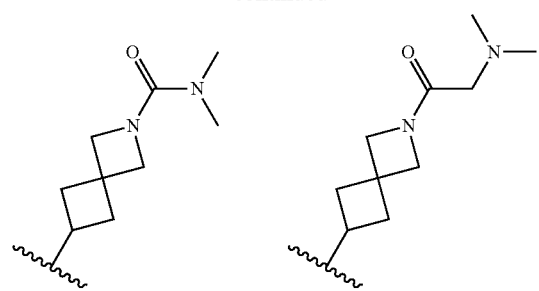
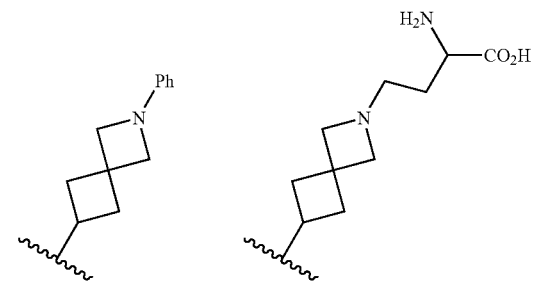
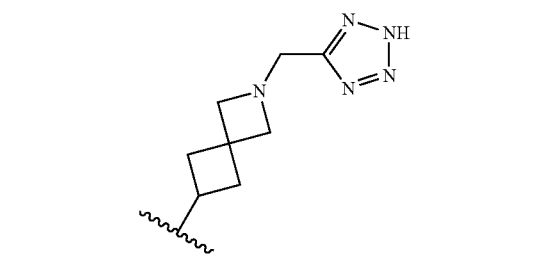
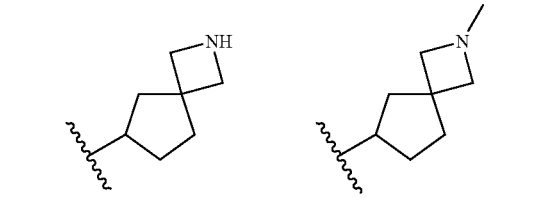
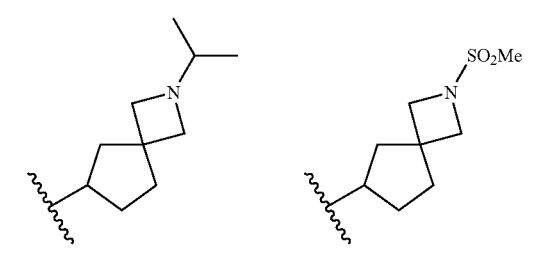
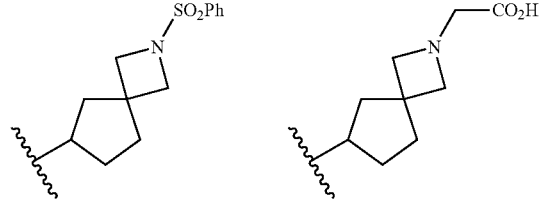
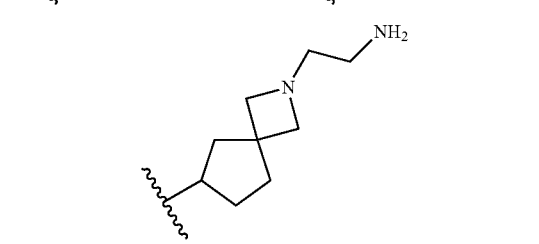
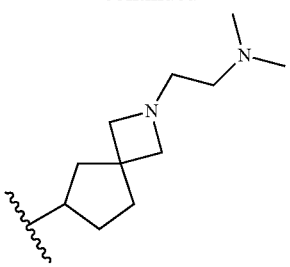
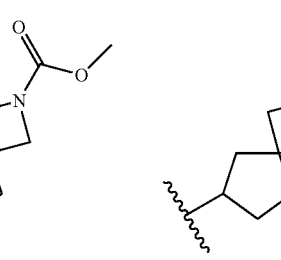
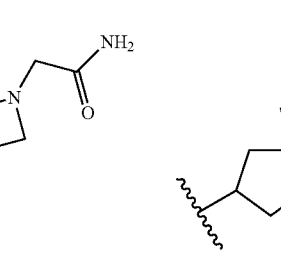
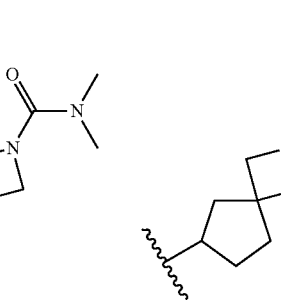
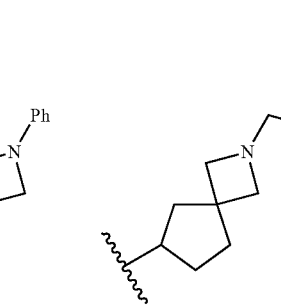
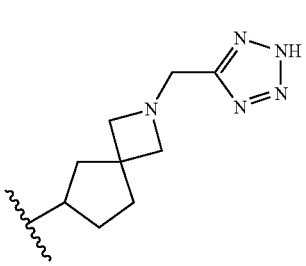

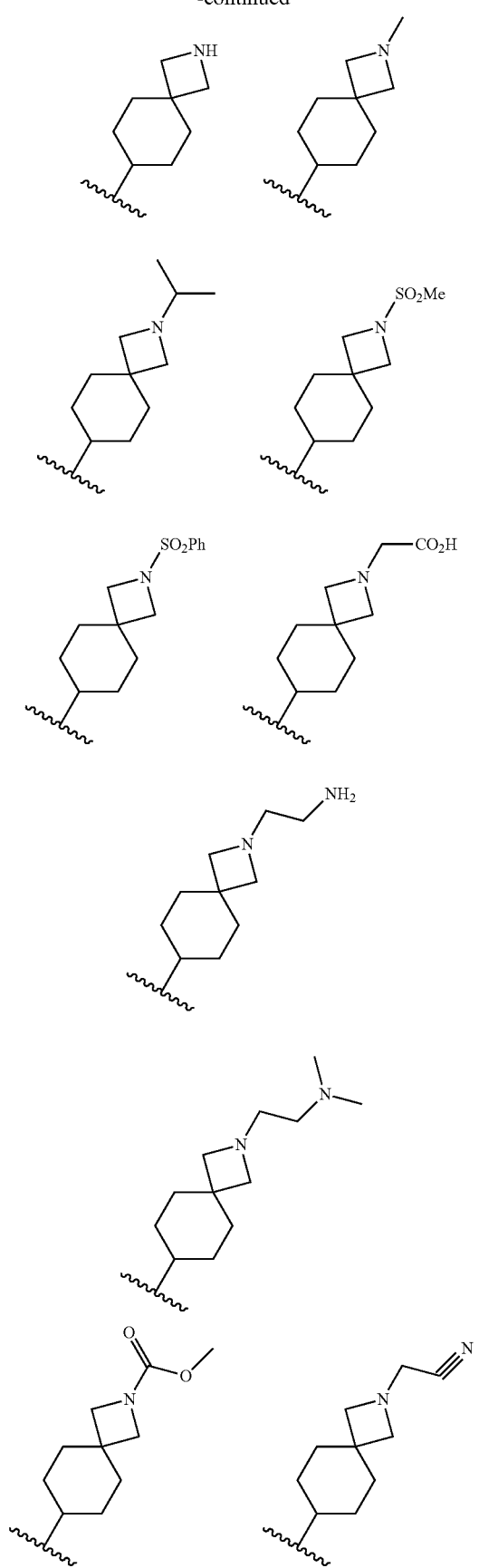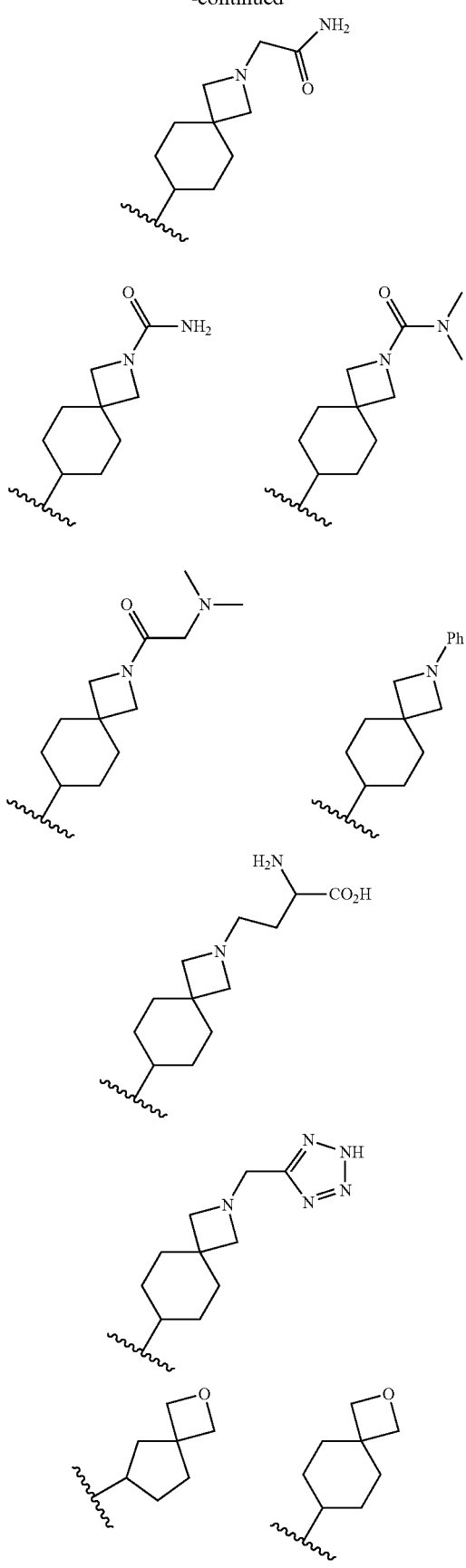

-continued
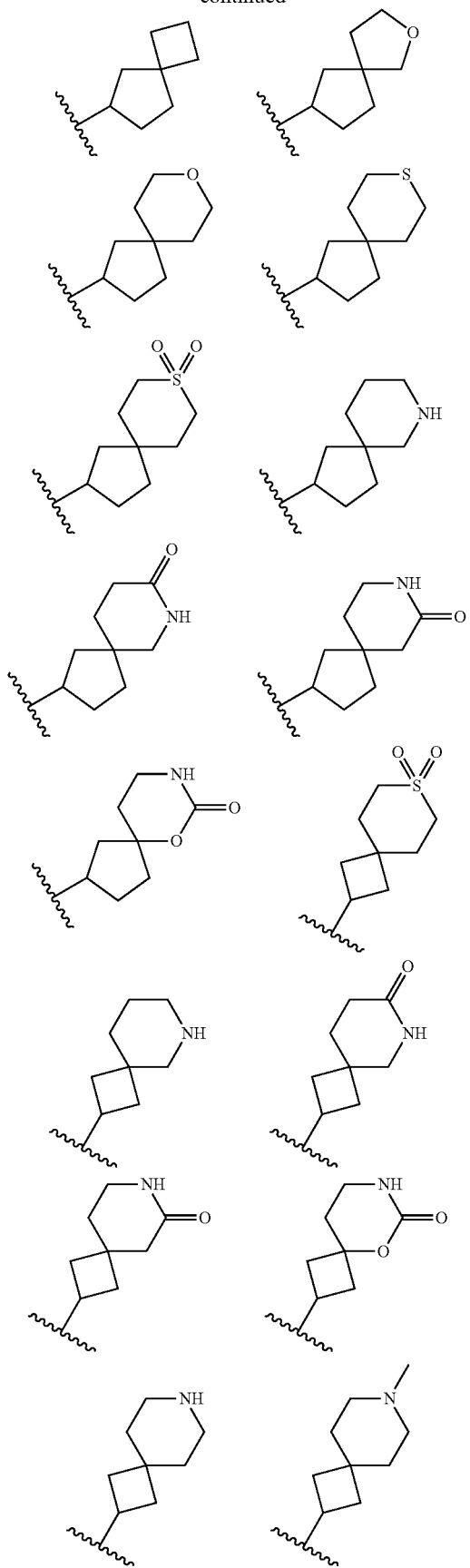
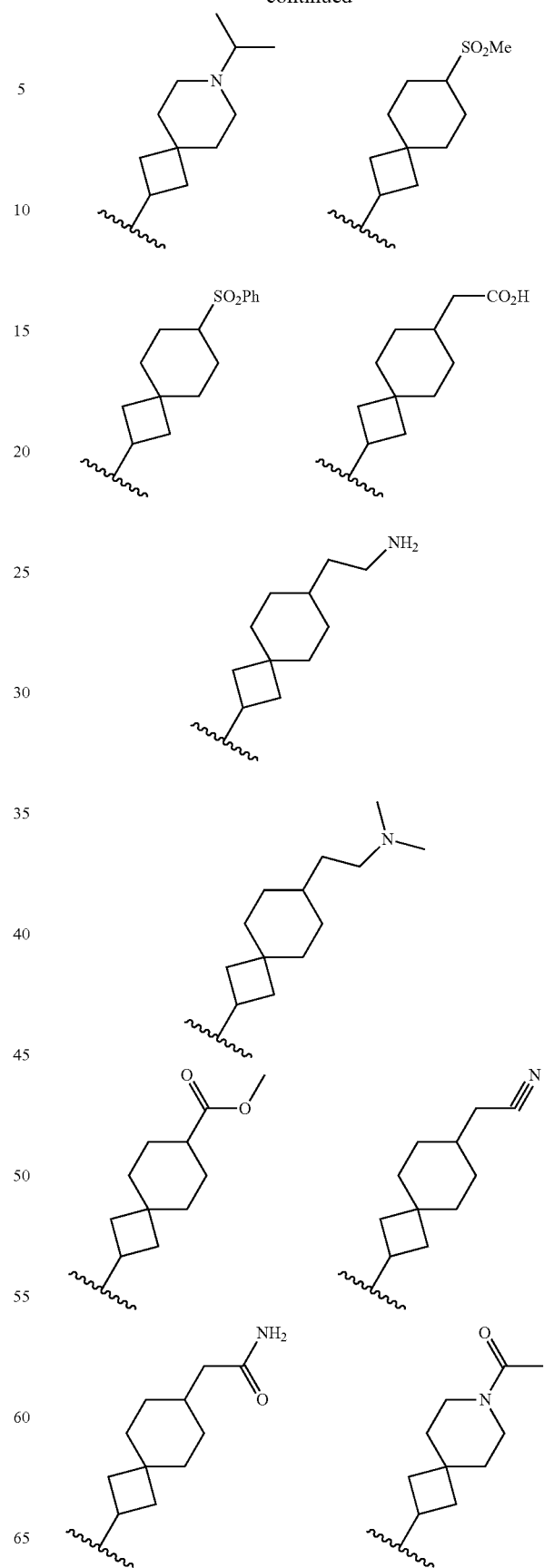

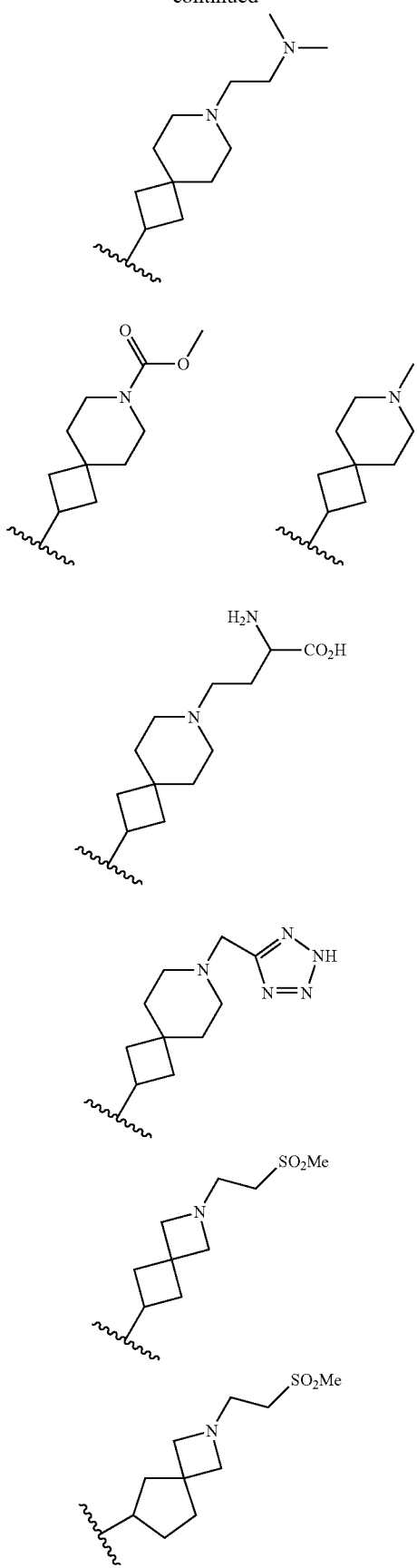
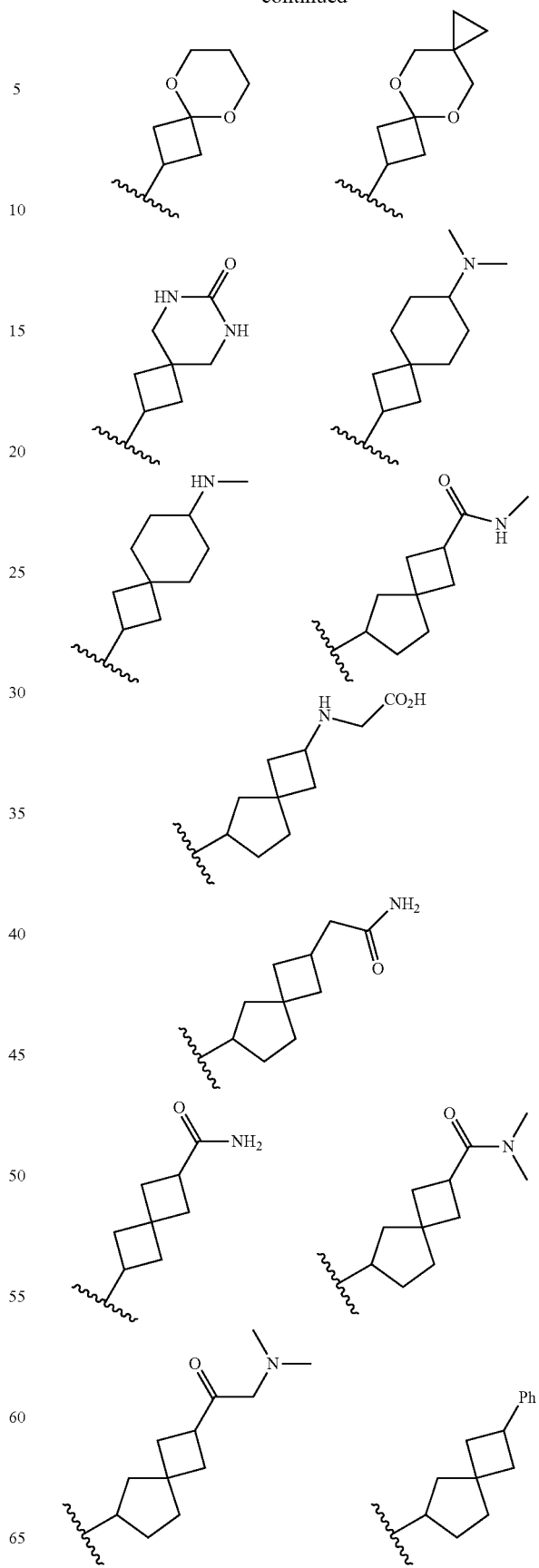

-continued

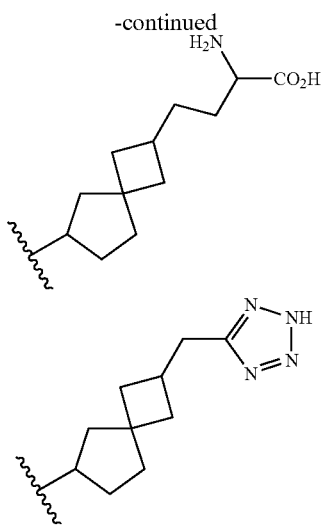

The compounds may be:
(±)-5-(1-(2-azaspiro[3.3]heptan-6-yl)-1H-pyrazol-4-yl)-3-(R)-1-(2,6-dichloro-3-fluorophenyl)ethoxy)pyridin-2-amine;
(R)-5-(1-(2-azaspiro[3.3]heptan-6-yl)-1H-pyrazol-4-yl)-3-((R)-1-(2,6-dichloro-3-fluorophenyl)ethoxy)pyridin-2-amine;
(R)-5-(1-(7-azaspiro[3.5]nonan-2-yl)-1H-pyrazol-4-yl)-3-(R)-1-(2,6-dichloro-3-fluorophenyl)ethoxy)pyridin-2-amine;
(R)-5-(1-(2-azaspiro[3.5]nonan-7-yl)-1H-pyrazol-4-yl)-3-((R)-1-(2,6-dichloro-3-fluorophenyl)ethoxy)pyridin-2-amine; and
(R)-5-(1-(6-azaspiro[3.5]nonan-2-yl)-1H-pyrazol-4-yl)-3-(1-(2,6-dichloro-3-fluorophenyl)ethoxy)pyridin-2-amine.

According to an embodiment, there is provided a composition comprising a combination of a compound of any the present invention and an anti-cancer agent selected from a cytotoxic agent, a antimitotic agent, an anti-metabolite, a proteasome inhibitor, a HDAC inhibitor and another kinase inhibitor.

According to an embodiment, there is provided a method treating a cancer in a patient in need thereof by administering to the patient a therapeutically effective amount of a compound of the present invention, or the composition of the present invention, or both, wherein the cancer is chosen from cancer of bladder, cancer of brain, cancer of breast, cancer of uterus, chronic lymphoid leukemia, colon cancer, esophagus cancer, liver cancer, lymphoblastic leukemia, follicular lymphomas, melanomas, malignant homeopathies, myelomas, ovarian cancer, non-small-cell lung cancer, prostate cancer, small-cell lung cancer, and lymphoid malignancy of B-cell origin.

According to an embodiment, there is provided a method of treating a patient afflicted with cancer by administering to the patient a therapeutically effective amount of a compound of the present invention in combination with radiotherapy.

According to an embodiment, there is provided a use of a compound of the present invention, or a composition of the present invention, or both, for the treatment of a cancer.

The cancer may be chosen from cancer of bladder, cancer of brain, cancer of breast, cancer of uterus, chronic lymphoid leukemia, colon cancer, esophagus cancer, liver cancer, lymphoblastic leukemia, follicular lymphomas, melanomas, malignant homeopathies, myelomas, ovarian cancer, non-small-cell lung cancer, prostate cancer, small-cell lung cancer, and lymphoid malignancy of B-cell origin.

The following terms are defined below.
Abbreviations used herein have their conventional meaning within the chemical and biological arts.

"alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

"Fluoroalkyl" means alkyl as defined above wherein one or more hydrogen atoms have been replaced by fluoro atoms.

"Alkylene" by itself or as part of another substituent means a divalent radical derived from an alkyl, as exemplified, but not limited, by —$CH_2CH_2CH_2CH_2$—, —$CH_2CH$=$CHCH_2$—, —$CH_2C$≡$CCH_2$—, —$CH_2CH_2CH$($CH_2CH_2CH_3$)$CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. A "fused analog" of cycloalkyl means a monocyclic rings fused to an aryl or heteroaryl group in which the point of attachment is on the non-aromatic portion. Examples of cycloalkyl and fused analogs thereof include cyclopropyl, cyclobutyl, cyclopentyl, cyclohexyl, cycloheptyl, tetrahydronaphthyl, decahydronaphthyl, indanyl, and the like.

"Alkoxy" means alkoxy groups of a straight or branched having the indicated number of carbon atoms. $C_{1-6}$alkoxy, for example, includes methoxy, ethoxy, propoxy, isopropoxy, and the like.

"Heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cycloalkoxy" means cycloalkyl as defined above bonded to an oxygen atom, such as cyclopropyloxy.

"Fluoroalkoxy" means alkoxy as defined above wherein one or more hydrogen atoms have been replaced by fluoro atoms.

"Aryl" means mono- or bicyclic aromatic rings containing only carbon atoms. A "fused analog" of aryl means an aryl group fused to a monocyclic cycloalkyl or monocyclic heterocyclyl group in which the point of attachment is on the aromatic portion. Examples of aryl and fused analogs thereof include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. A "fused analog" of heteroaryl means a heteroaryl group fused to a monocyclic cycloalkyl or monocyclic heterocyclyl group in which the point of attachment is on the aromatic portion. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

The said alkyl groups, cycloalkyl, alkynyl, alkenyl, aryl groups and heteroaryl groups referred to in the definitions are unsubstituted or are substituted by at least one substituent selected from the group consisting of substituents.

The said substituents are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent-x groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms, aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl(alkyl)amino groups having from 1 to 6 carbon atoms, alkanoylaminoalkyl groups having from 1 to 6 carbon atoms in both the alkanoyl and alkyl part, alkanoyl(alkyl)aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from 1 to 4 carbon atoms;

"Heterocyclyl" means mono- or bicyclic saturated rings containing at least one heteroatom selected from N, S and O, each of said ring having from 3 to 10 atoms in which the point of attachment may be carbon or nitrogen. A "fused analog" of heterocyclyl means a monocyclic heterocycle fused to an aryl or heteroaryl group in which the point of attachment is on the non-aromatic portion. Examples of "heterocyclyl" and fused analogs thereof include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrugs may also have improved solubility in pharmaceutical compositions over the parent drug. An example, without limitation, of a prodrug would be a compound of any of Formula I, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

DESCRIPTION OF THE INVENTION

The present invention provides novel spirocyclic molecules and methods of preparing and potential therapeutic uses of these novel compounds. The inventive compounds may provide an effective treatment of proliferative diseases such as cancers and neurologic diseases, that are more resistant to Crizotinib The present invention provides in part compounds of Formula I, which are useful as c-MET and/or ALK inhibitors:

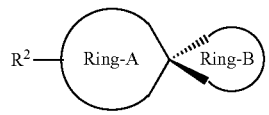

Formula I or a pharmaceutically acceptable salt thereof, wherein:

Ring A is a 3 to 12 membered carbocyclic ring in which one or more carbon ring atoms are optionally replaced with one or more O, S, —C(O)—, —C(S)— and $NR^1$; Ring A is also optionally substituted by one or more $R^c(s)$;

Ring B is a 3 to 12 membered carbocyclic ring in which one or more carbon ring atoms are optionally replaced with one or more O, S, —C(O)—, —C(S)— and $NR^1$; Ring B is also optionally substituted by $R^c$;

$R^1$ is independently hydrogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —S(O)$_m R^4$, —SO$_2 NR^4 R^5$, —S(O)$_2 OR^4$, —C(O)$R^4$, —NR$^4$C(O)$R^5$, —(CR$^6$R$^7$)$_n$C(O)OR$^4$, —(CR$^6$R$^7$)$_n$OR$^4$, —(CR$^6$R$^7$)$_n$C(O)NR$^4$R$^5$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, each hydrogen in $R^1$ is optionally substituted by $R^c$. $R^1$ can also be a $C_{1-12}$ alkyl, in which one carbon atom is optionally replaced with Si, O, S atom or one of the protons in $R^1$ is optionally replaced with —P(O)(OR$^9$)$_2$;

$R^c$ is independently chosen from halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —S(O)$_m R^4$, —S(O)$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$OR$^4$, —(CR$^6$R$^7$)$_n$C(O)NR$^4$R$^5$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, —NH$_2$, SF$_5$, —OH, —O—C$_{1-12}$alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic ring) or —O—(CH$_2$)$_n$(5-12 membered heteroaryl ring);

and wherein each hydrogen in $R^c$ is unsubstituted or substituted by $R^8$, and wherein $R^c$ groups on adjacent atoms are uncombined or combine to form a $C_{6-12}$ aryl, 5-12 membered heteroaryl ring, $C_{3-12}$ cycloalkyl or 3-12 membered heteroalicyclic ring;

n is selected from 1 to 4.

$R^2$ is selected from

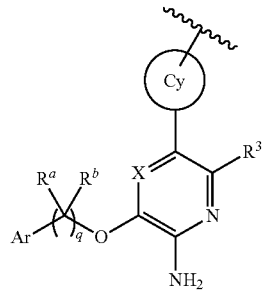

wherein:
X is N or $CR^{12}$; Ar is $C_{6-12}$ aryl, 5-12 membered heteroaryl ring, $C_{3-12}$ cycloalkyl or 3-12 membered heteroalicyclic ring, and Ar is optionally substituted by one or more $R^c$ groups;

is selected from $C_{6-12}$ aryl, 5-12 membered heteroaryl ring, $C_{3-12}$ cycloalkyl or 3-12 membered heteroalicyclic ring, optionally substituted by one, two or three $R^{cc}$ groups;
$R^3$ is hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —S(O)$_m$R$^4$, —SO$_2$NR$^4$R$^5$, —S(O)$_2$OR$^4$, —SF$_5$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, and each hydrogen in $R^3$ is optionally substituted by $R^8$; $R^{cc}$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —S(O)$_m$R$^4$, —S(O)$_2$NR$^4$R$^5$, —S(O)$_2$OR$^4$, —SF$_5$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$OR$^4$, —(CR$^6$R$^7$)$_n$C(O)NR$^4$R$^5$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, each hydrogen in $R^{cc}$ is optionally substituted by $R^8$, and $R^c$ groups on adjacent atoms may combine to form a $C_{6-12}$ aryl, 5-12 membered heteroaryl ring, $C_{3-12}$ cycloalkyl or 3-12 membered heteroalicyclic ring;

$R^4$, $R^5$, $R^6$ and $R^7$ is independently hydrogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring; or any two of $R^4$, $R^5$, $R^6$ and $R^7$ bound to the same nitrogen atom may, together with the nitrogen to which they are bound, be combined to form a 3 to 12 membered heteroalicyclic or 5-12 membered heteroaryl ring optionally containing 1 to 3 heteroatoms selected from N, O, and S; or any two of $R^4$, $R^5$, $R^6$ and $R^7$ bound to the same carbon atom may be combined to form a $C_{3-12}$ cycloalkyl, $C_{6-12}$ aryl, 3-12 membered heteroalicyclic ring or 5-12 membered heteroaryl ring; and each hydrogen in $R^4$, $R^5$, $R^6$ and $R^7$ is optionally substituted by $R^8$, or two hydrogen atoms on the same carbon atom in $R^4$, $R^5$, $R^6$ and $R^7$ is optionally an oxo substituent; $R^8$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —NH$_2$, —CN, —OH, —O—C$_{1-12}$ alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic ring) or —O—(CH$_2$)$_n$(5-12 membered heteroaryl ring); and each hydrogen in R$^8$ is optionally substituted by R$^{11}$;

R$^9$ is independently a C$_{1-12}$ alkyl, aryl, heteroaryl which is optionally substituted;

R$^{10}$ is independently a C$_{1-12}$ alkyl which is optionally substituted;

R$^{11}$ is independently halogen, C$_{1-12}$ alkyl, C$_{1-12}$ alkoxy, C$_{3-12}$ cycloalkyl, C$_{6-12}$ aryl, 3-12 membered heteroalicyclic ring, 5-12 membered heteroaryl ring, —O—C$_{1-12}$ alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic ring), —O—(CH$_2$)$_n$(5-12 membered heteroaryl ring) or —CN, and each hydrogen in R$^{11}$ is optionally substituted by halogen, —OH, —CN, —C$_{1-12}$ alkyl which may be partially or fully halogenated, —O—C$_{1-12}$ alkyl which may be partially or fully halogenated, or substituted with —CO;

R$^{12}$ is hydrogen, halogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic ring, 5-12 membered heteroaryl ring, —S(O)$_m$R$^4$, —SO$_2$NR$^4$R$^5$, —S(O)$_2$OR$^4$, SF$_5$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, and each hydrogen in R$^{12}$ is optionally substituted by R$^3$;

R$^a$ and R$^b$ is independently hydrogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic ring, 5-12 membered heteroaryl ring, —(CR$^6$R$^7$)$_n$OR$^4$, —C(O)R$^4$, —OC(O)R$^4$, —(CR$^6$R$^7$)$_n$C(O)OR$^4$, —(CR$^6$R$^7$)$_n$NCR$^4$R$^5$ or —C(O)NR$^4$R$^5$; together with the carbon to which they are attached to, R$^a$ or R$^b$ may combine to form a 3-12 membered ring which may contains one or more heteroatom such as NR$^4$, O, S, Si. R$^a$ or R$^b$ may also combine with a ring atom of Ar or a substituent of Ar to form a C$_{5-12}$ cycloalkyl, 5-12 membered heteroalicyclic ring; and each hydrogen in R$^a$ and R$^b$ is optionally substituted by R$^c$;

each m is independently 0, 1 or 2; each n is independently 0, 1, 2, 3 or 4; q is 1, 2, 3 or 4;

or a pharmaceutically acceptable salt, hydrate or solvate thereof.

In a particular aspect of this embodiment,

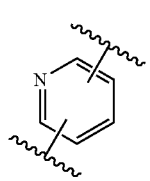

is selected from

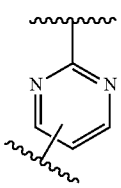 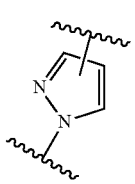 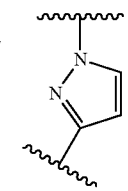

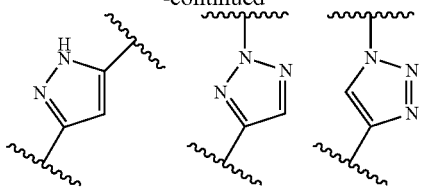

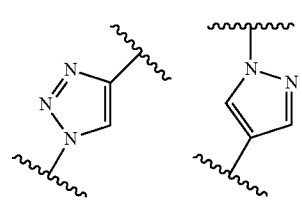

or an aryl, bicyclic aryl, bicyclic heteroaryl, optionally substituted by one, two or three R$^c$ groups.

In another embodiment, the invention provides a compound with R$^2$ having the following (R)-stereo-configuration:

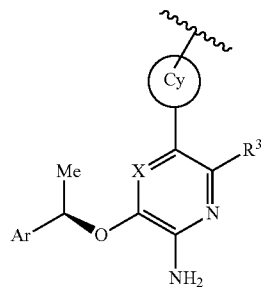

Wherein Ar, Cy, X and R$^3$ are defined as aforesaid.

In another embodiment, the invention provides a compound of the following

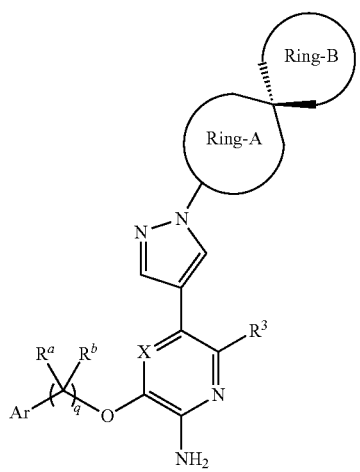

-continued

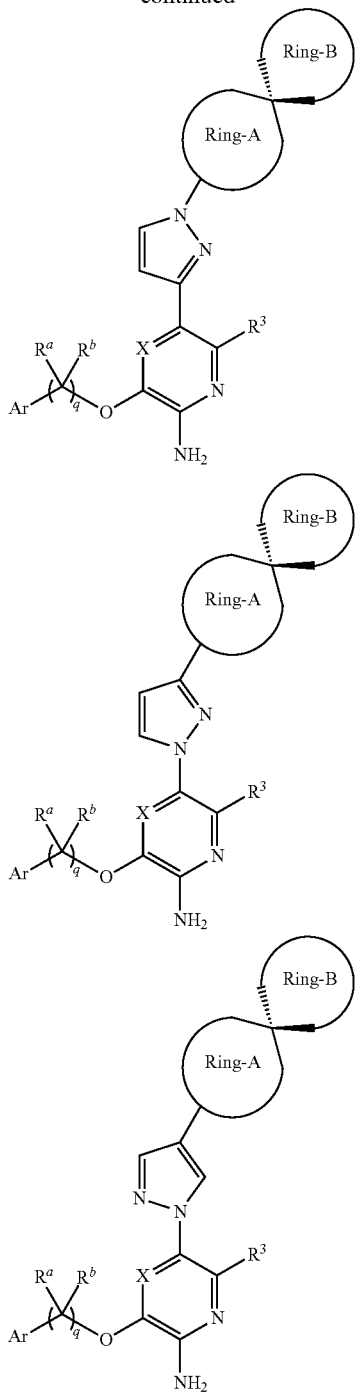

wherein:

Ring A is a 3 to 12 membered carbocyclic ring in which one or more carbon ring atoms are optionally replaced with one or more O, S, —C(O)—, —C(S)— and NR$^1$; Ring A is also optionally substituted by one or more R$^c$;

Ring B is a 3 to 12 membered carbocyclic ring in which one or more carbon ring atoms are optionally replaced with one or more O, S, —C(O)—, —C(S)— and NR$^1$; Ring B is also optionally substituted by one or more R$^c$;

R$^1$ is independently hydrogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —S(O)$_m$R$^4$, —SO$_2$NR$^4$R$^5$, —S(O)$_2$OR$^4$, —CN, —C(O)R$^4$, —OC(O)R$^4$, —O(CR$^6$R$^7$)$_n$R$^4$, —O(CR$^6$R$^7$)$_n$OR$_4$, —NR$^4$C(O)R$^5$, —(CR$^6$R$^7$)$_n$C(O)OR$^4$, —(CR$^6$R$^7$)$_n$OR$^4$, —(CR$^6$R$^7$)$_n$C(O)NR$^4$R$^5$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, each hydrogen in R$^1$ is optionally substituted by R$^c$;

X is N or CR$^{12}$; Ar is $C_{6-12}$ aryl, 5-12 membered heteroaryl ring, $C_{3-12}$ cycloalkyl or 3-12 membered heteroalicyclic ring, and A is optionally substituted by one or more R$^c$ groups; R$^3$ is hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, and each hydrogen in R$^3$ is optionally substituted by R$^8$; R$^c$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —S(O)$_m$R$^4$, —S(O)$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$OR$^4$, —(CR$^6$R$^7$)$_n$C(O)NR$^4$R$^5$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, each hydrogen in R$^c$ is optionally substituted by R$^8$, and R$^c$ groups on adjacent atoms may combine to form a $C_{6-12}$ aryl, 5-12 membered heteroaryl ring, $C_{3-12}$ cycloalkyl or 3-12 membered heteroalicyclic ring; R$^4$, R$^5$, R$^6$ and R$^7$ is independently hydrogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring; or any two of R$^4$, R$^5$, R$^6$ and R$^7$ bound to the same nitrogen atom may, together with the nitrogen to which they are bound, be combined to form a 3 to 12 membered heteroalicyclic or 5-12 membered heteroaryl ring optionally containing 1 to 3 heteroatoms selected from N, O, and S; or any two of R$^4$, R$^5$, R$^6$ and R$^7$ bound to the same carbon atom may be combined to form a $C_{3-12}$ cycloalkyl, $C_{6-12}$ aryl, 3-12 membered heteroalicyclic ring or 5-12 membered heteroaryl ring; and each hydrogen in R$^4$, R$^5$, R$^6$ and R$^7$ is optionally substituted by R$^8$, or two hydrogen atoms on the same carbon atom in R$^4$, R$^5$, R$^6$ and R$^7$ is optionally an oxo substituent; R$^8$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —NH$_2$, —CN, —OH, —O—$C_{1-12}$alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic ring) or —O—(CH$_2$)$_n$(5-12 membered heteroaryl ring); and each hydrogen in R$^8$ is optionally substituted by R$^{11}$;

R$^{11}$ is independently halogen, $C_{1-12}$ alkyl, $C_{1-12}$ alkoxy, $C_{3-12}$ cycloalkyl, 12 aryl, 3-12 membered heteroalicyclic ring, 5-12 membered heteroaryl ring, —O—$C_{1-12}$ alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic ring), —O—(CH$_2$)$_n$(5-12 membered heteroaryl ring) or —CN, and each hydrogen in R$^{11}$ is optionally substituted by halogen, —OH, —CN, —$C_{1-12}$ alkyl which may be partially or fully halogenated, —O—$C_{1-12}$ alkyl which may be partially or fully halogenated, or substituted with —CO;

R$^{12}$ is hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —S(O)$_m$R$^4$, —SO$_2$NR$^4$R$^5$, —S(O)$_2$OR$^4$, SF$_5$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, and each hydrogen in R$^{12}$ is optionally substituted by R$^3$; R$^a$ and R$^b$ is independently hydrogen, halogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic ring, 5-12 membered heteroaryl ring, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —NR$^4$C(O)R$^5$, —(CR$^6$R$^7$)$_n$C(O)OR$^4$, —(CR$^6$R$^7$)$_n$NCR$^4$R$^5$, —NR$^4$C(O)NR$^5$R$^6$, —NR$^4$S(O)$_2$R$^5$ or —C(O)NR$^4$R$^5$; together with the carbon to which they are attached to, R$^a$ or R$^b$ may combine to form a 3-12 membered ring which may contains one or more heteroatom such as NR$^4$, O, S, Si. R$^a$ and R$^b$ may also combine with a ring atom of A or a substituent of A to form a C$_{3-12}$ cycloalkyl, 3-12 membered heteroalicyclic ring, C$_{6-12}$ aryl or 5-12 membered heteroaryl ring ring fused to A; and each hydrogen in R$^a$ and R$^b$ is optionally substituted by R$^c$;

each m is independently 0, 1 or 2; each n is independently 0, 1, 2, 3 or 4; q is 1, 2, 3 or 4;

or a pharmaceutically acceptable salt, hydrate or solvate thereof.

In another embodiment, the invention provides a compound of the following

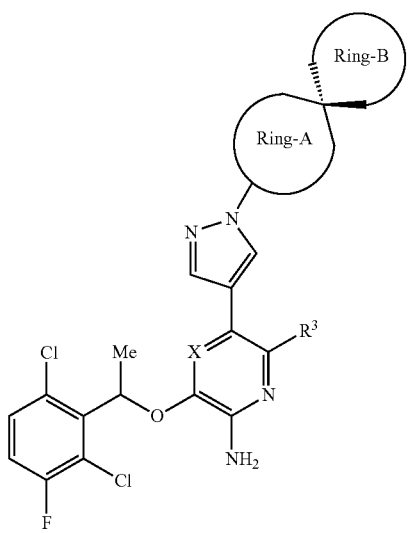

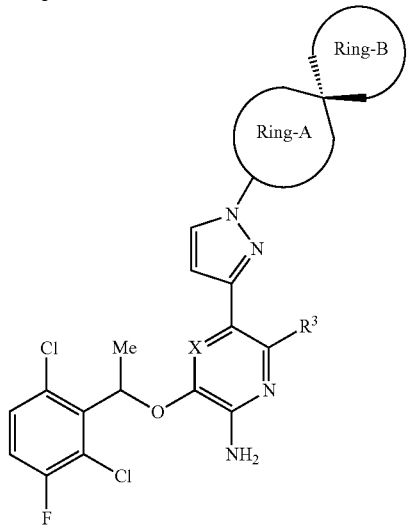

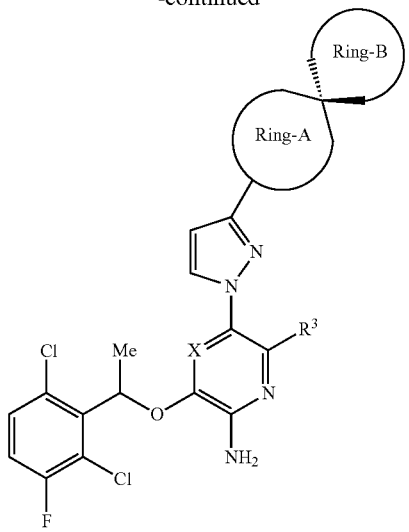

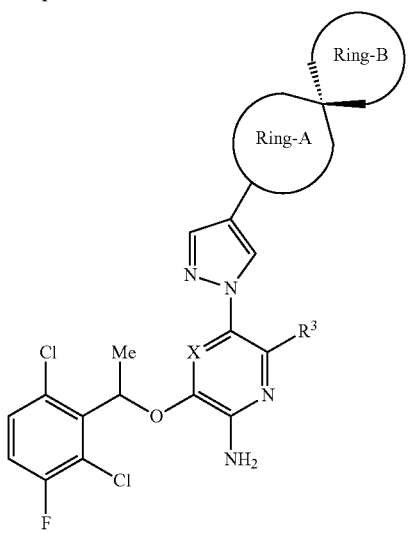

wherein:

Ring A is a 3 to 12 membered carbocyclic ring in which one or more carbon ring atoms are optionally replaced with one or more O, S, —C(O)—, —C(S)— and NR$^1$; Ring A is also optionally substituted by one or more R$^c$;

Ring B is a 3 to 12 membered carbocyclic ring in which one or more carbon ring atoms are optionally replaced with one or more O, S, —C(O)—, —C(S)— and NR$^1$; Ring B is also optionally substituted by one or more R$^c$;

R$^1$ is independently hydrogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic ring, 5-12 membered heteroaryl ring, —S(O)$_m$R$^4$, —SO$_2$NR$^4$R$^5$, —S(O)$_2$OR$^4$, —C(O)R$^4$, —NR$^4$C(O)R$^5$, —(CR$^6$R$^7$)$_n$C(O)OR$^4$, —(CR$^6$R$^7$)$_n$OR$^4$, —(CR$^6$R$^7$)$_n$C(O)NR$^4$R$^5$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, each hydrogen in R$^1$ is optionally substituted by R$^c$;

X is N or CR$^{12}$; R$^3$ is hydrogen, halogen, C$_{1-12}$ alkyl, C$_{2-12}$ alkenyl, C$_{2-12}$ alkynyl, C$_{3-12}$ cycloalkyl, C$_{6-12}$ aryl, 3-12 membered heteroalicyclic, 5-12 membered heteroaryl ring, —S(O)$_m$R$^4$, —SO$_2$NR$^4$R$^5$, —S(O)$_2$OR$^4$, SF$_5$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, and each hydrogen in $R^3$ is optionally substituted by $R^8$; $R^c$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl ring, —S(O)$_m$R$^4$, —S(O)$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$OR$^4$, —(CR$^6$R$^7$)$_n$C(O)NR$^4$R$^5$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, each hydrogen in $R^c$ is optionally substituted by $R^8$, and $R^c$ groups on adjacent atoms may combine to form a $C_{6-12}$ aryl, 5-12 membered heteroaryl ring, $C_{3-12}$ cycloalkyl or 3-12 membered heteroalicyclic ring; $R^4$, $R^5$, $R^6$ and $R^7$ is independently hydrogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl ring; or any two of $R^4$, $R^5$, $R^6$ and $R^7$ bound to the same nitrogen atom may, together with the nitrogen to which they are bound, be combined to form a 3 to 12 membered heteroalicyclic or 5-12 membered heteroaryl ring optionally containing 1 to 3 heteroatoms selected from N, O, and S; or any two of $R^4$, $R^5$, $R^6$ and $R^7$ bound to the same carbon atom may be combined to form a $C_{3-12}$ cycloalkyl, $C_{6-12}$ aryl, 3-12 membered heteroalicyclic ring or 5-12 membered heteroaryl ring; and each hydrogen in $R^4$, $R^5$, $R^6$ and $R^7$ is optionally substituted by $R^8$, or two hydrogen atoms on the same carbon atom in $R^4$, $R^5$, $R^6$ and $R^7$ is optionally an oxo substituent; $R^8$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl ring, —NH$_2$, —CN, —OH, —O—C$_{1-12}$alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic) or —O—(CH$_2$)$_n$(5-12 membered heteroaryl ring); and each hydrogen in $R^8$ is optionally substituted by $R^{11}$;

$R^{11}$ is independently halogen, $C_{1-12}$ alkyl, $C_{1-12}$ alkoxy, $C_{3-12}$ cycloalkyl, $C_{6-12}$ aryl, 3-12 membered heteroalicyclic, 5-12 membered heteroaryl ring, —O—C$_{1-12}$ alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic), —O—(CH$_2$)$_n$(5-12 membered heteroaryl ring) or —CN, and each hydrogen in $R^{11}$ is optionally substituted by halogen, —OH, —CN, —C$_{1-12}$ alkyl which may be partially or fully halogenated, —O—C$_{1-12}$ alkyl which may be partially or fully halogenated, or substituted with —CO;

$R^{12}$ is hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl ring, —S(O)$_m$R$^4$, —SO$_2$NR$^4$R$^5$, —S(O)$_2$OR$^4$, SF$_5$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, and each hydrogen in $R^{12}$ is optionally substituted by $R^3$; each m is independently 0, 1 or 2; each n is independently 0, 1, 2, 3 or 4; or a pharmaceutically acceptable salt, hydrate or solvate thereof.

In another embodiment, the invention provides a compound with the following stereo-configuration:

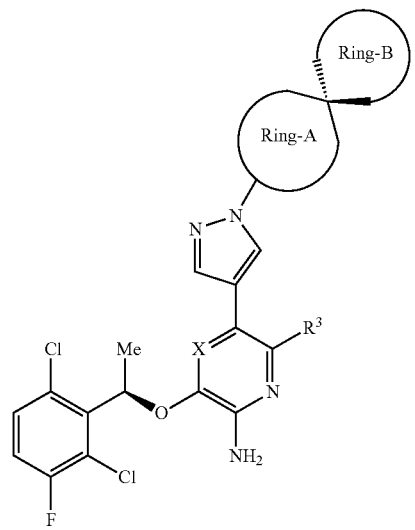

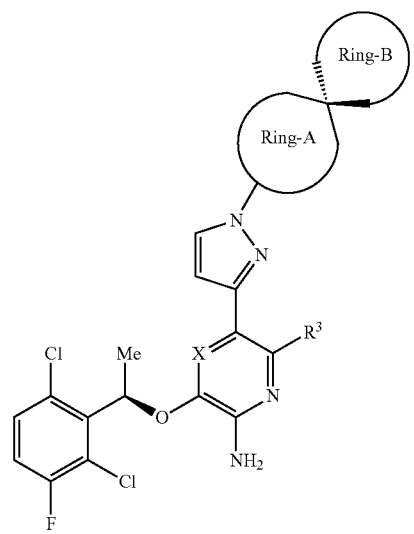

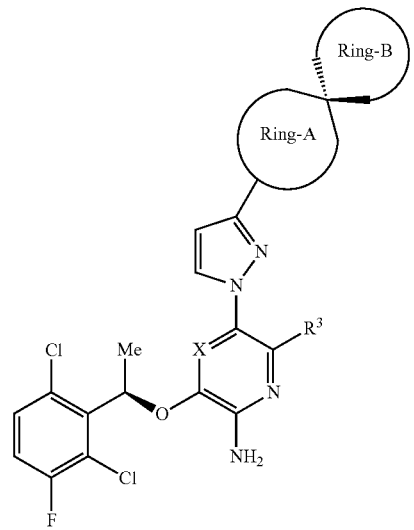

33
-continued
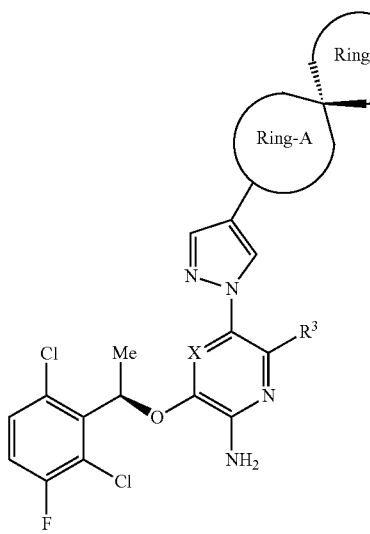
wherein:
Ring A, Ring B, X and R³ are defined as aforesaid.
In another embodiment, the invention provides stable isotope-labeled compounds of Formula I.
In another embodiment, the invention provides a compound of the following structure:
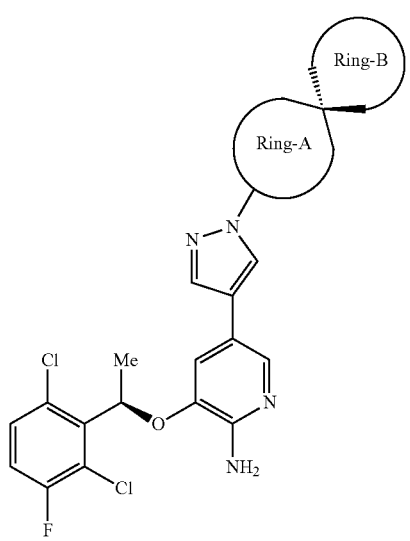
wherein
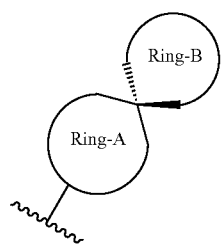
34
is selected from the group consisting of:
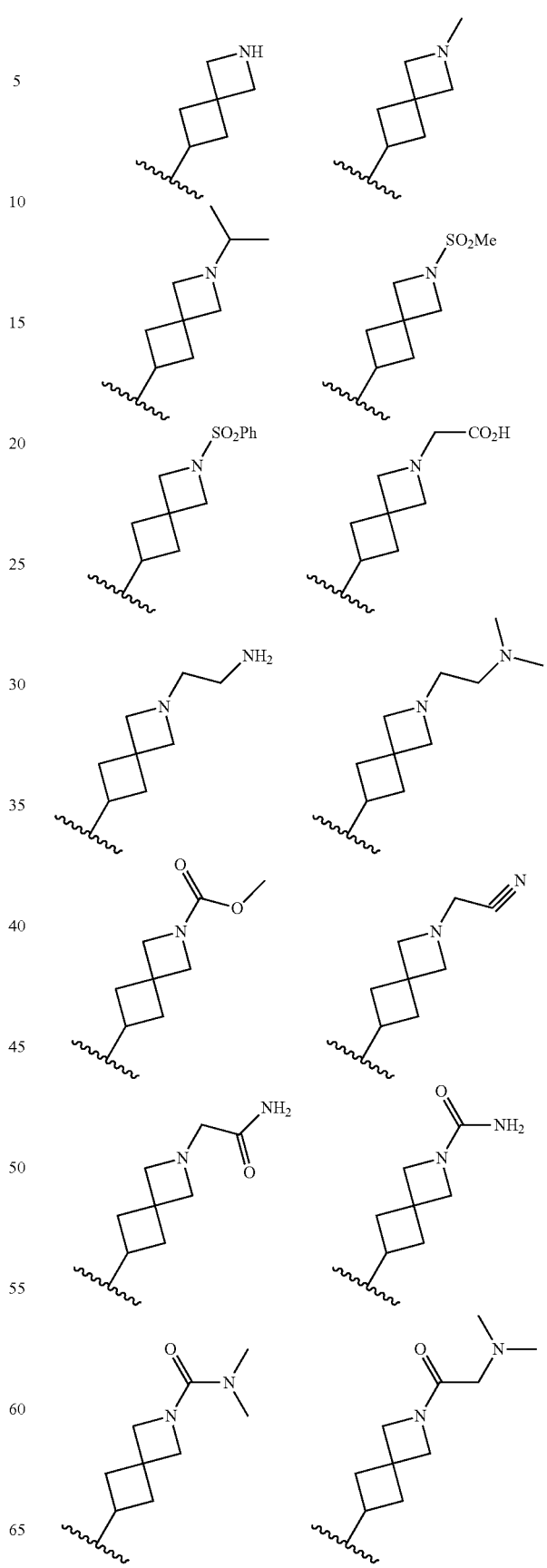

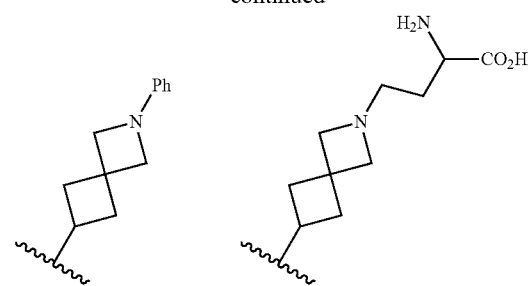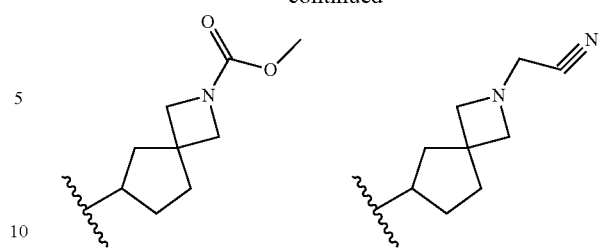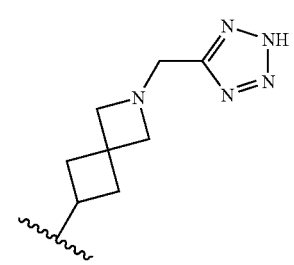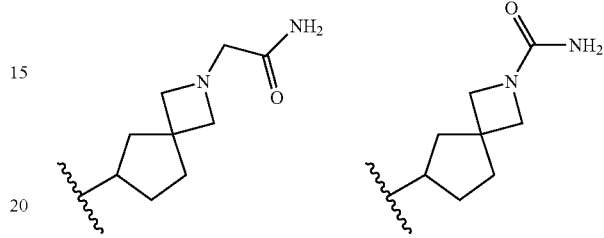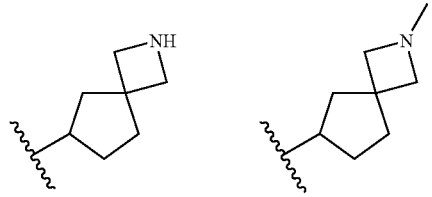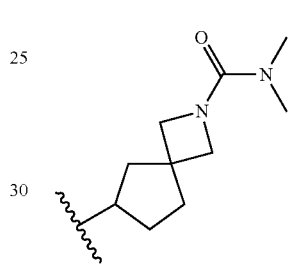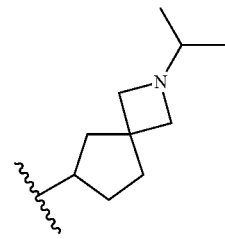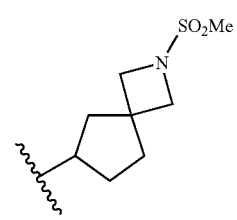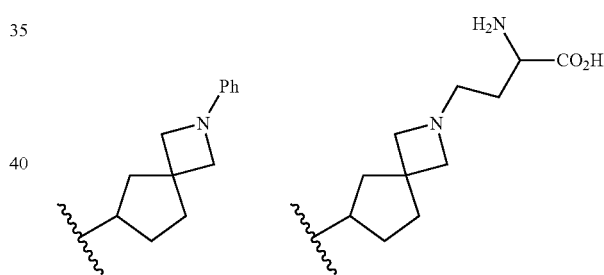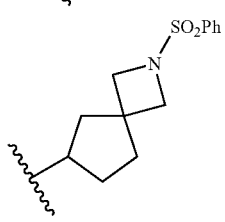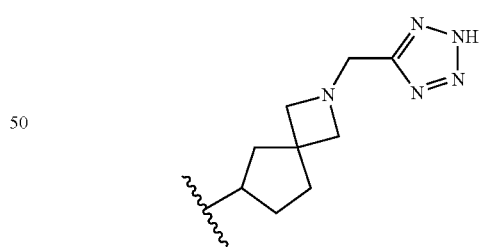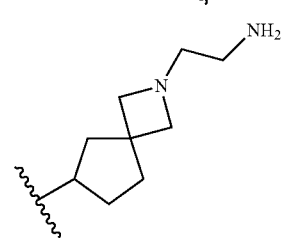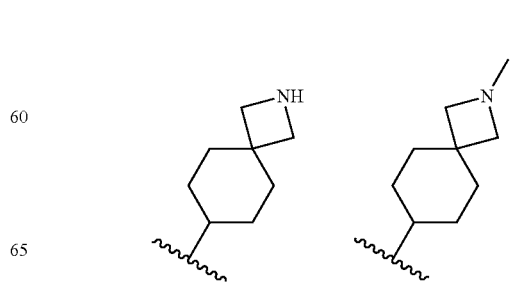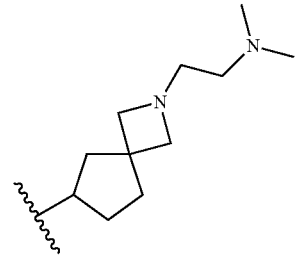

-continued
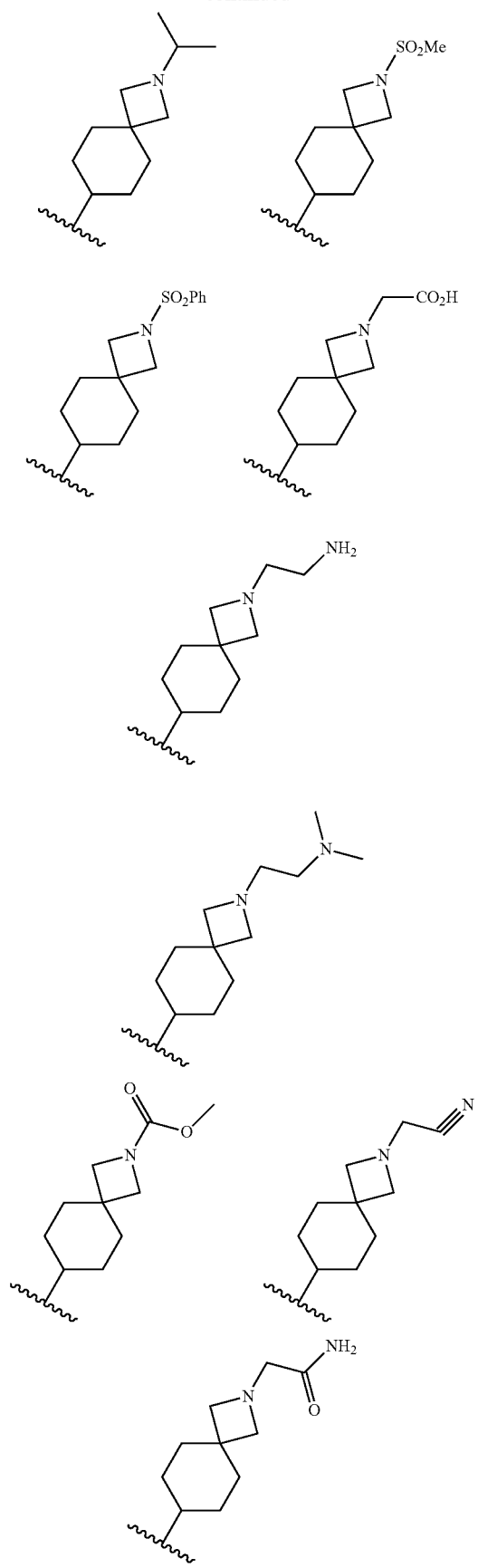
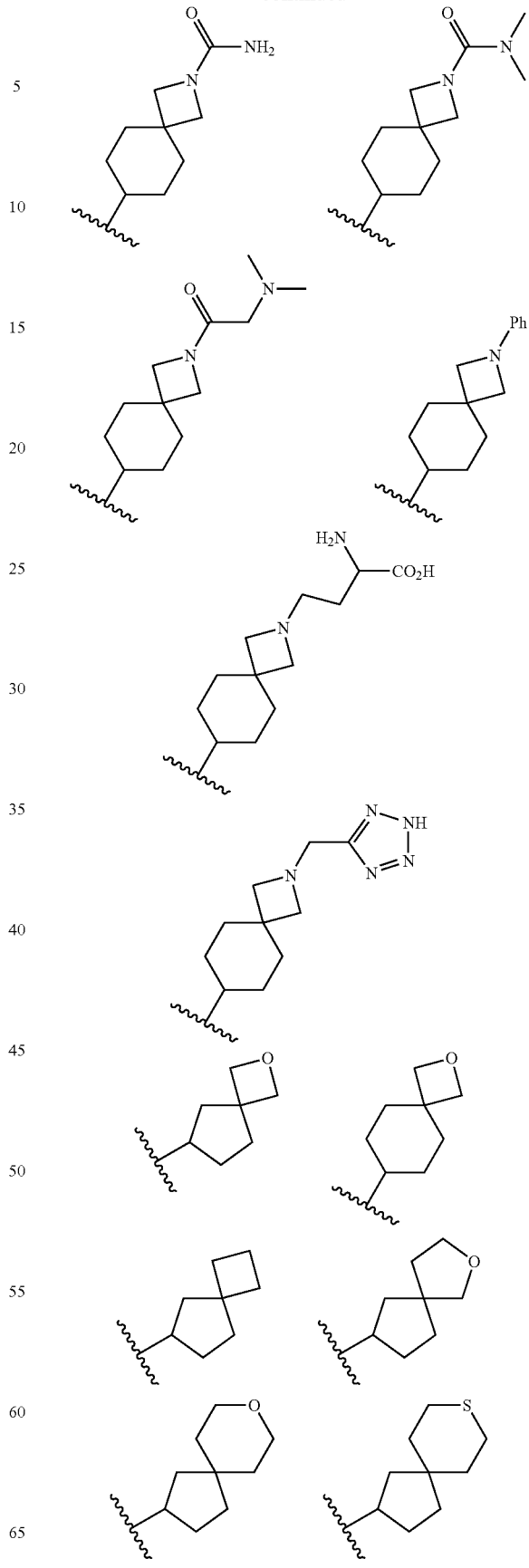

-continued
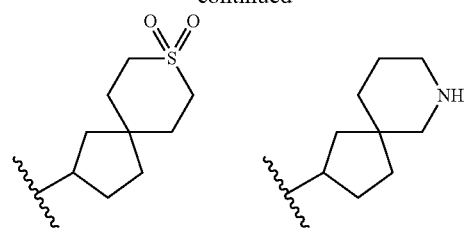 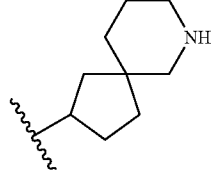
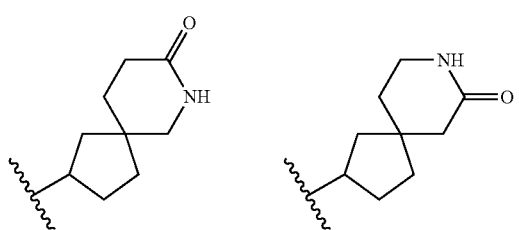 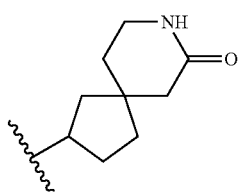
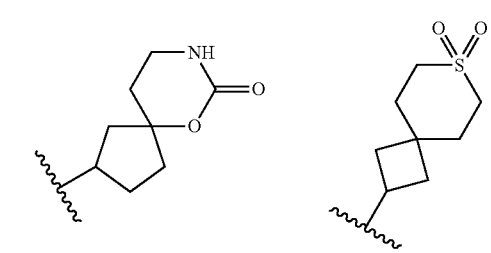 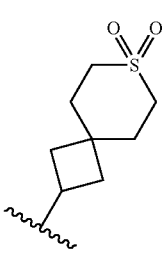
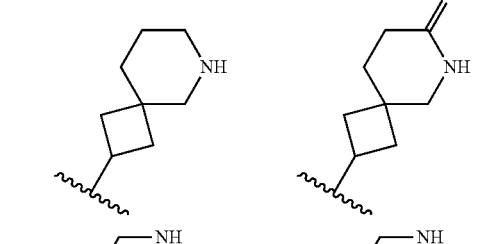 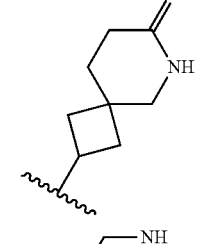
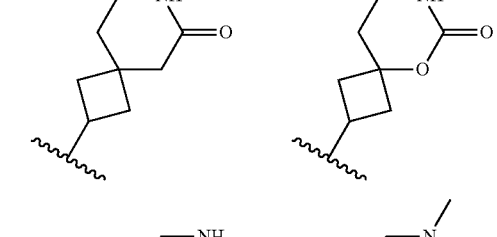 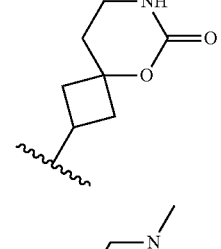
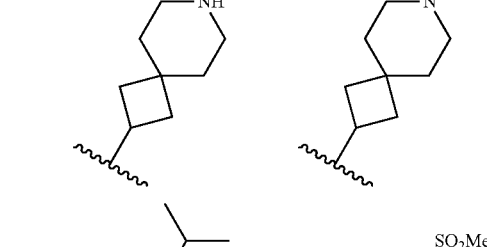 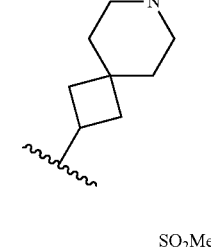
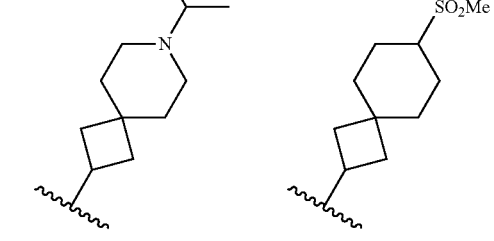 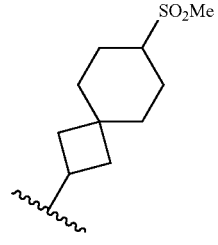
-continued
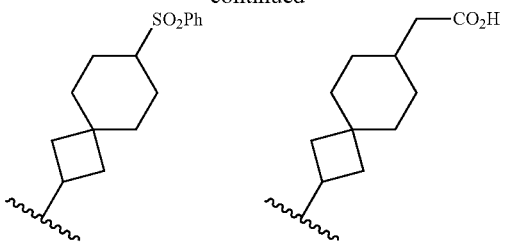 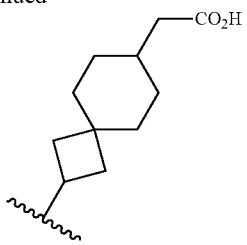
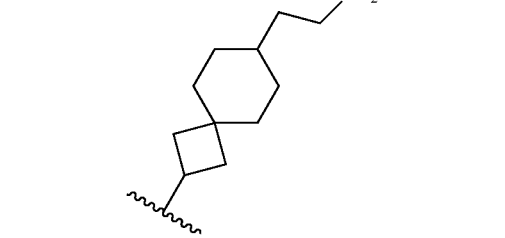
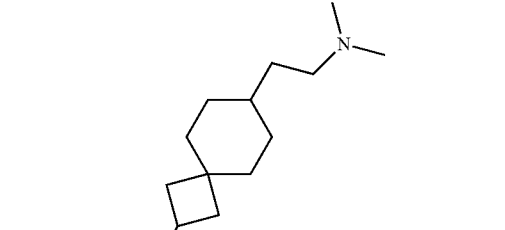
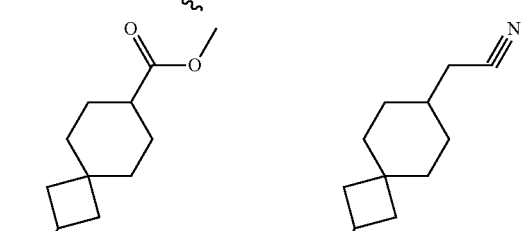
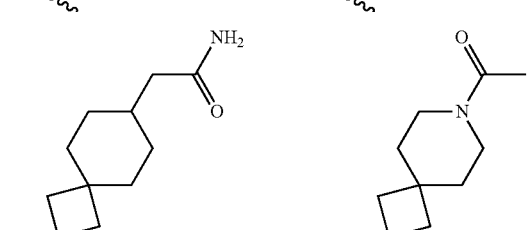
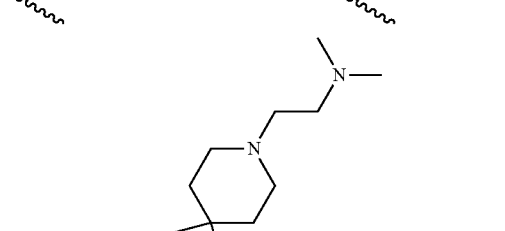

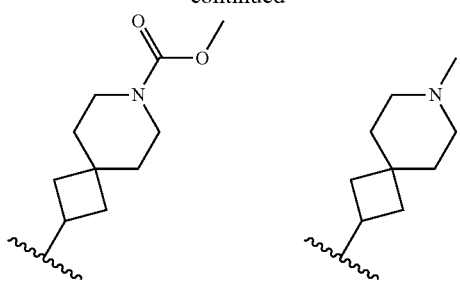
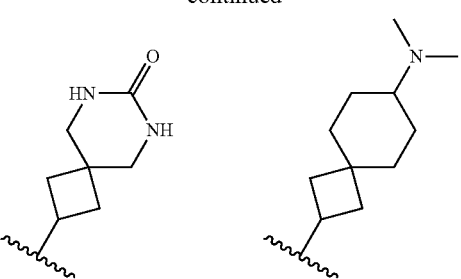
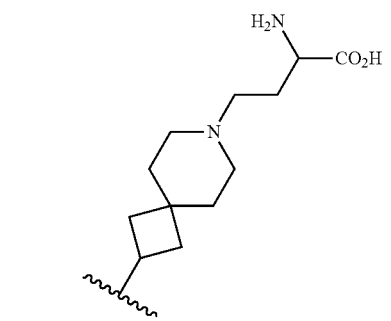
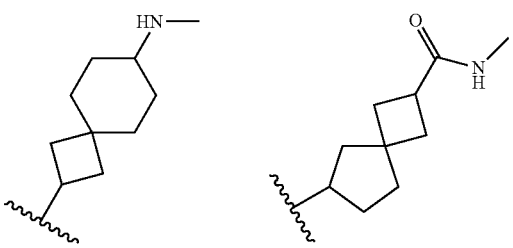
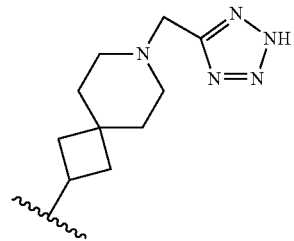
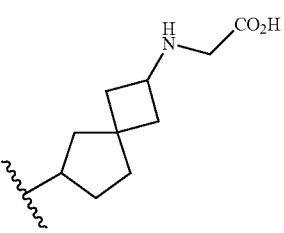
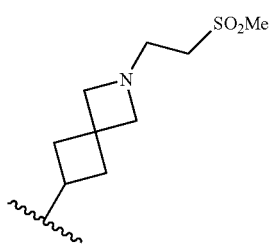
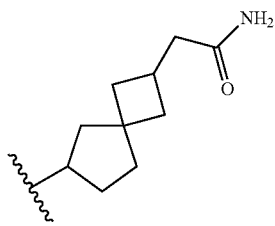
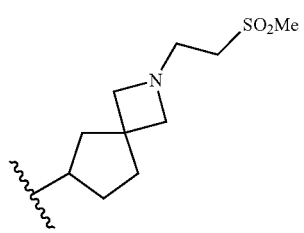
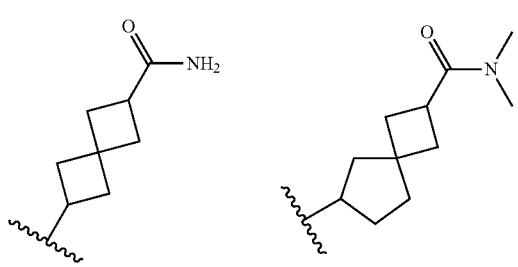
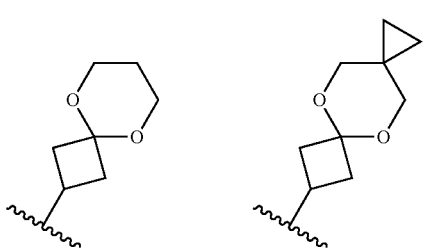
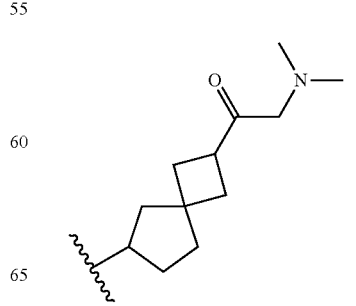
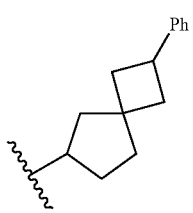

-continued

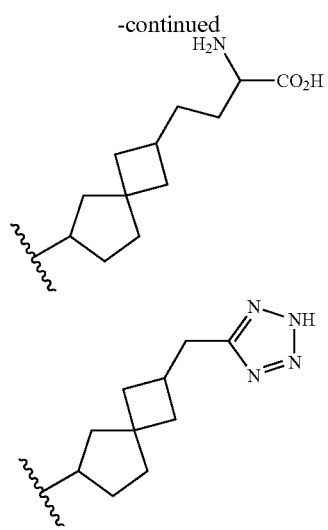

Optical Isomers-Diastereomers-Geometric Isomers-Tautomers:

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or EtOAc or a mixture thereof. The pair of enantiomers thus obtained may be separated into individual stereoisomers by conventional means, for example by the use of an optically active amine or acid as a resolving agent or on a chiral HPLC column.

Alternatively, any enantiomer of a compound of the general Formula I may be obtained by stereospecific synthesis using optically pure starting materials or reagents of known configuration.

Stable Isotope-Labeled Analogs:

One or more than one of the protons in compounds of Formula I can be replaced with deuterium atom(s), thus providing deuterated analogs that may have improved pharmacological activities.

Salts and Formulation

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzyl ethylenediamine, diethylamine, 2-diethyl-aminoethanol, 2-dimethylaminoethanol, ethanolamine, ethylenediamine, N-ethyl-morpholine, N-ethylpiperidine, glucamine, glucosamine, histidine, hydramine, isopropyl-amine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycet-anol, or condensation products of ethylene oxide with partial esters derived from fatty acids and a hexitol such as polyoxy-ethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an I atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns).

This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from log to 20 mg of the compound of the invention per actuation and the actuation volume may vary from 11 to 100l. A typical formulation may comprise a compound of formula I, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 fig to 10 mg of the compound of formula I. The overall daily dose will typically be in the range 1 lag to 10 mg which may be administered in a single dose or, more usually, as divided doses throughout the day.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature and not as restrictive and the full scope of the subject matter is set forth in the claims.

Utilities

The compounds of the present invention are useful for treating diseases associated with abnormal activities of cMET and ALK.

The present invention also comprises methods of treating diseases in a patient by using methods comprising administering to the patient a therapeutically effective amount of a compound having formula I.

More especially, the compounds according to the invention will be useful in the treatment of diseases of abnormal cell growth and/or dysregulated apoptosis, such as mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblasitoma, or a combination thereof. Still another embodiment comprises methods of treating mesothioloma, bladder cancer, pancreatic cancer, skin cancer, cancer of the head or neck, cutaneous or intraocular melanoma, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblasitoma, or a combination of one or more of the above cancers in a patient, said methods comprising administering thereto a therapeutically effective amount of a compound having Formula I.

The present invention relates also to pharmaceutical compositions comprising at least one compound of formula I on its own or in combination with one or more pharmaceutically acceptable excipients.

Among the pharmaceutical compositions according to the invention there may be mentioned more especially those that are suitable for oral, parenteral, nasal, per- or transcutaneous, rectal, perlingual, ocular or respiratory administration, especially tablets or dragees, sublingual tablets, sachets, packets, gelatin capsules, glossettes, lozenges, suppositories, creams, ointments, dermal gels, and drinkable or injectable ampoules.

The dosage varies according to the sex, age and weight of the patient, the route of administration, the nature of the therapeutic indication, or any associated treatments, and ranges from 0.01 mg to 1 g per 24 hours in one or more administrations.

Moreover, the present invention relates also to the combination of a compound of formula I with one or more anticancer agents selected from cytotoxic agents, mitotic poisons, anti-metabolites, proteasome inhibitors and kinase inhibitors, and to the use of that type of combination in the manufacture of medicaments for use in the treatment of cancer.

The compounds of the invention may also be used in combination with radiotherapy in the treatment of cancer.

Compounds having formula I are also expected to be useful as chemotherapeutic agents in combination with therapeutic agents that include, but are not limited to, angiogenesis inhibitors, antiproliferative agents, other kinase inhibitors, other receptor tyrosine kinase inhibitors, aurora kinase inhibitors, polo-like kinase inhibitors, bcr-abl kinase inhibitors, growth factor inhibitors, COX-2 inhibitors, EP4 antagonists, non-steroidal anti-inflammatory drugs (NSAIDS), antimitotic agents, alkylating agents, antimetabolites, intercalating antibiotics, platinum containing agents, growth factor inhibitors, ionizing radiation, cell cycle inhibitors, enzymes, topoisomerase inhibitors, biologic response modifiers, immunologicals, antibodies, hormonal therapies, retinoids/deltoids plant alkaloids, proteasome inhibitors, HSP-90 inhibitors, histone deacetylase inhibitors (HDAC) inhibitors, purine analogs, pyrimidine analogs, MEK inhibitors, CDK inhibitors, ErbB2 receptor inhibitors, mTOR inhibitors, Bcl inhibitors, Mcl inhibitors and combinations thereof as well as other antitumor agents.

Angiogenesis inhibitors include, but are not limited to, EGFR inhibitors, PDGFR inhibitors, VEGFR inhibitors, TTE2 inhibitors, IGFIR inhibitors, matrix metalloproteinase 2 (MMP-2) inhibitors, matrix metalloproteinase 9 (MMP-9) inhibitors, thrombospondin analogs such as thrombospondin-1 and N-Ac-Sar-Gly-Val-D-alloIle-Thr-Nva-Ile-Arg-Pro-NHCH$_2$CH$_3$ or a salt thereof and analogues of N-Ac-Sar-Gly-Val-D-alloIle-Thr-Nva-Ile-Arg-Pro-NHCH$_2$CH$_3$ such as N-Ac-Gly-Val-D-alloIle-Ser-Gln-Ile-Arg-Pro-NHCH$_2$CH$_3$ or a salt thereof.

Examples of EGFR inhibitors include, but are not limited to, Iressa (gefitinib), Tarceva (erlotinib or OSI-774), Icotinib, Erbitux (cetuximab), EMD-7200, ABX-EGF, HR3, IgA antibodies, TP-38 (IVAX), EGFR fusion protein, EGF-vaccine, anti-EGFr immunoliposomes and Tykerb (lapatinib).

Examples of PDGFR inhibitors include, but are not limited to, CP-673,451 and CP-868596.

Examples of VEGFR inhibitors include, but are not limited to, Avastin (bevacizumab), Sutent (sunitinib, SUI 1248), Nexavar (sorafenib, BAY43-9006), CP-547,632, axitinib (AG13736), Apatinib, cabozantinib, Zactima (vandetanib, ZD-6474), AEE788, AZD-2171, VEGF trap, Vatalanib (PTK-787, ZK-222584), Macugen, M862, Pazopanib (GW786034), ABT-869, BC-00016 and angiozyme.

Examples of thrombospondin analogs include, but are not limited to, ABT-510.

Examples of BCL inhibitors include, but not limited to, ABT263, ABT199 and GX-015.

Examples of aurora kinase inhibitors include, but are not limited to, VX-680, AZD-1152 and MLN-8054. Example of polo-like kinase inhibitors include, but are not limited to, BI-2536.

Examples of bcr-abl kinase inhibitors include, but are not limited to, Gleevec (imatinib) and Dasatinib (BMS354825).

Examples of platinum containing agents includes, but are not limited to, cisplatin, Paraplatin (carboplatin), eptaplatin, lobaplatin, nedaplatin, Eloxatin (oxaliplatin) or satraplatin.

Examples of mTOR inhibitors includes, but are not limited to, CCI-779, rapamycin, temsirolimus, everolimus, RAD001, INK-128 and ridaforolimus.

Examples of HSP-90 inhibitors includes, but are not limited to, geldanamycin, radicicol, 17-AAG, KOS-953, 17-DMAG, CNF-101, CNF-1010, 17-AAG-nab, NCS-683664, Mycograb, CNF-2024, PU3, PU24FC1, VER49009, IPI-504, SNX-2112 and STA-9090.

Examples of histone deacetylase inhibitors (HDAC) includes, but are not limited to, Suberoylanilide hydroxamic acid (SAHA), MS-275, valproic acid, TSA, LAQ-824, Trapoxin, tubacin, tubastatin, ACY-1215 and Depsipeptide.

Examples of MEK inhibitors include, but are not limited to, PD325901, ARRY-142886, ARRY-438162 and PD98059.

Examples of CDK inhibitors include, but are not limited to, flavopyridol, MCS-5A, CVT-2584, seliciclib (CYC-202, R-roscovitine), ZK-304709, PHA-690509, BMI-1040, GPC-286199, BMS-387,032, PD0332991 and AZD-5438.

Examples of COX-2 inhibitors include, but are not limited to, celecoxib, parecoxib, deracoxib, ABT-963, etoricoxib, lumiracoxib, BMS347070, RS 57067, NS-398, valdecoxib, paracoxib, rofecoxib, SD-8381, 4-Methyl-2-(3,4-dimethylphenyl)-l-(4-sulfamoyl-phenyl-IH-pyrrole, T-614, JTE-522, S-2474, SVT-2016, CT-3, SC-58125 and etoricoxib.

Examples of non-steroidal anti-inflammatory drugs (NSAIDs) include, but are not limited to, Salsalate (Amigesic), Diflunisal (Dolobid), Ibuprofen (Motrin), Ketoprofen (Orudis), Nabumetone (Relafen), Piroxicam (Feldene), Naproxen (Aleve, Naprosyn), Diclofenac (Voltaren), Indomethacin (Indocin), Sulindac (Clinoril), Tolmetin (Tolectin), Etodolac (Lodine), Ketorolac (Toradol) and Oxaprozin (Daypro).

Examples of ErbB2 receptor inhibitors include, but are not limited to, CP-724-714, CI-1033, (canertinib), Herceptin (trastuzumab), Omitarg (2C4, petuzumab), TAK-165, GW-572016 (lonafarnib), GW-282974, EKB-569, PI-166, dHER2 (HER2 Vaccine), APC8024 (HER2 Vaccine), anti-HER/2neu bispecific antibody, B7.her2IgG3, AS HER2 trifunctional bispecfic antibodies, mAB AR-209 and mAB 2B-1.

Examples of alkylating agents include, but are not limited to, nitrogen mustard N-oxide, cyclophosphamide, ifosfamide, trofosfamide, Chlorambucil, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, KW-2170, mafosfamide, and mitolactol, carmustine (BCNU), lomustine (CCNU), Busulfan, Treosulfan, Decarbazine and Temozolomide.

Examples of antimetabolites include but are not limited to, methotrexate, 6-mercaptopurine riboside, mercaptopurine, uracil analogues such as 5-fluorouracil (5-FU) alone or in combination with leucovorin, tegafur, UFT, doxifluridine, carmofur, cytarabine, cytarabine, enocitabine, S-I, Alimta (premetrexed disodium, LY231514, MTA), Gemzar (gemcitabine), fludarabine, 5-azacitidine, capecitabine, cladribine, clofarabine, decitabine, eflornithine, ethnylcytidine, cytosine arabinoside, hydroxyurea, TS-I, melphalan, nelarabine, nolatrexed, ocfosate, disodium premetrexed, pentostatin, pelitrexol, raltitrexed, triapine, trimetrexate, vidarabine, vincristine, vinorelbine, mycophenolic acid, tiazofurin, Ribavirin, EICAR, hydroxyurea and deferoxamine.

Examples of antibiotics include intercalating antibiotics but are not limited to, aclarubicin, actinomycins such as actinomycin D, amrubicin, annamycin, adriamycin, bleomycin a, bleomycin b, daunorubicin, doxorubicin, elsamitrucin, epirbucin, glarbuicin, idarubicin, mitomycin C, nemorubicin, neocarzinostatin, peplomycin, pirarubicin, rebeccamycin, stimalamer, streptozocin, valrubicin, zinostatin and combinations thereof.

Examples of topoisomerase inhibiting agents include, but are not limited to, one or more agents selected from the group consisting of aclarubicin, amonafide, belotecan, camptothecin, 10-hydroxycamptothecin, 9-aminocamptothecin, diflomotecan, irinotecan HCL (Camptosar), edotecarin, epirubicin (Ellence), etoposide, exatecan, gimatecan, lurtotecan, orathecin (Supergen), BN-80915, mitoxantrone, pirarbucin, pixantrone, rubitecan, sobuzoxane, SN-38, tafluposide and topotecan.

Examples of antibodies include, but are not limited to, Rituximab, Cetuximab,

Bevacizumab, Trastuzimab, specific CD40 antibodies and specific IGF1R antibodies, Examples of hormonal therapies include, but are not limited to, exemestane (Aromasin), leuprolide acetate, anastrozole (Arimidex), fosrelin (Zoladex), goserelin, doxercalciferol, fadrozole, formestane, tamoxifen citrate (tamoxifen), Casodex, Abarelix, Trelstar, finasteride, fulvestrant, toremifene, raloxifene, lasofoxifene, letrozole, flutamide, bicalutamide, megesterol, mifepristone, nilutamide, dexamethasone, predisone and other glucocorticoids.

Examples of retinoids/deltoids include, but are not limited to, seocalcitol (EB 1089, CB 1093), lexacalcitrol (KH 1060), fenretinide, Aliretinoin, Bexarotene and LGD-1550.

Examples of plant alkaloids include, but are not limited to, vincristine, vinblastine, vindesine and vinorelbine.

Examples of proteasome inhibitors include, but are not limited to, bortezomib (Velcade), MGI 32, NPI-0052 and PR-171.

Examples of immunologicals include, but are not limited to, interferons and numerous other immune enhancing agents. Interferons include interferon alpha, interferon alpha-2a, interferon, alpha-2b, interferon beta, interferon gamma-1a, interferon gamma-1b (Actimmune), or interferon gamma-nl and combinations thereof. Other agents include filgrastim, lentinan, sizofilan, TheraCys, ubenimex, WF-10, aldesleukin, alemtuzumab, BAM-002, decarbazine, daclizumab, denileukin, gemtuzumab ozogamicin, ibritumomab, imiquimod, lenograstim, lentinan, melanoma vaccine (Corixa), molgramostim, OncoVAC-CL, sargaramostim, tasonermin, tecleukin, thymalasin, tositumomab, Virulizin, Z-100, epratuzumab, mitumomab, oregovomab, pemtumomab (Y-muHMFGI), Provenge (Dendreon), CTLA4 (cytotoxic lymphocyte antigen 4) antibodies and agents capable of blocking CTLA4 such as MDX-010.

Examples of biological response modifiers are agents that modify defense mechanisms of living organisms or biological responses, such as survival, growth, or differentiation of tissue cells to direct them to have anti-tumor activity. Such agents include krestin, lentinan, sizofrran, picibanil and ubenimex.

Examples of pyrimidine analogs include, but are not limited to, 5-Fluorouracil,

Floxuridine, Doxifluridine, Ratitrexed, cytarabine (ara C), Cytosine arabinoside, Fludarabine, and Gemcitabine.

Examples of purine analogs include but are not limited to, Mercaptopurine and thioguanine.

Examples of antimitotic agents include, but are not limited to, paclitaxel, docetaxel, epothilone D (KOS-862) and ZK-EPO.

Synthesis

The compounds of the present invention may be prepared according to the following synthetic scheme:

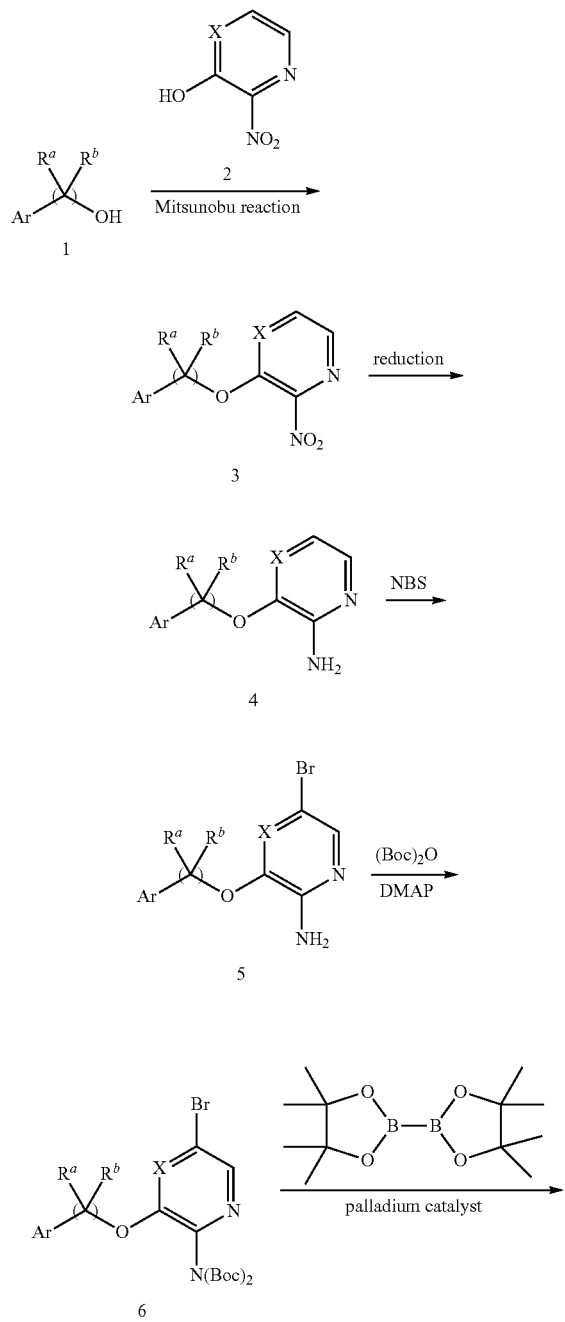

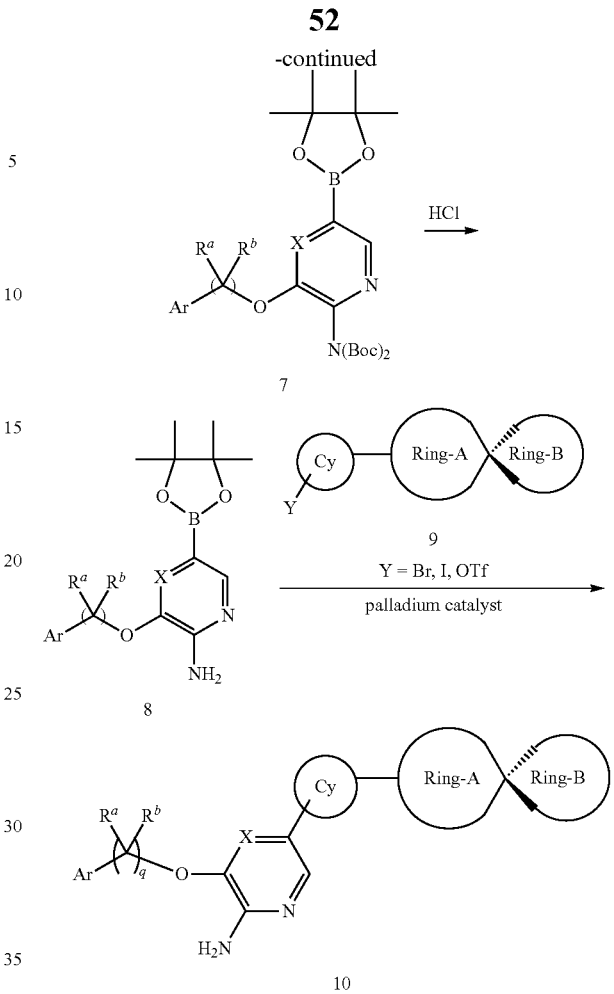

Mitsunobu reaction of alcohol 1 with 2 under standard conditions provides aryl ether 3, which can be reduced to aniline 4. Bromination of 4 with NBS yields bromide 5. The NH₂ group in bromide 5 can be protected with BOC group to give compound 6. Reaction of 6 with 4,4,4',4',5,5,5',5'-octamethyl-2,2'-bi(1,3,2-dioxaborolane) and a palladium catalyst gives rise to boronate 7. The Boc group in 7 can be cleaved under acidic conditions to give compound 8. Cross-coupling reaction of 8 with an appropriate coupling partner 9 which contains a spiro-moiety can yields the desired product 10. A deprotection step maybe used to produce the final product in various salt forms.

Compounds of the present invention may be made by synthetic chemical processes, examples of which are shown herein below. It is meant to be understood that the order of the steps in the processes may be varied, that reagents, solvents and reaction conditions may be substituted for those specifically mentioned, and that vulnerable moieties may be protected and deprotected, as necessary.

The following abbreviations have the meanings indicated. DBU means 1,8-diazabicyclo[5.4.0]undec-7-ene; DIBAL means diisobutylaluminum hydride; DIEA means diisopropylethylamine; DMAP means N,N-dimethylaminopyridine; DME means 1,2-dimethoxyethane; DMF means N,N-dimethylformamide; dmpe means 1,2-bis(dimethylphosphino)ethane; DMSO means dimethylsulfoxide; dppb means 1,4-bis(diphenylphosphino)butane; dppe means 1,2-bis(diphenylphosphino)ethane; dppf means 1,1'-bis(diphenylphosphino)ferrocene; dppm means 1,1'-bis (diphenylphosphino)methane; DIAD means diisopropylazodicarboxylate; EDCI means 1-(3-dimethylaminopropyl)-3-ethylcarbodiimide; HATU means 2-(7-Aza-1H-benzotriazole-1-yl)-1,1,3,3-tetramethyluronium hexafluorophosphate; HMPA means hexamethylphosphoramide; IPA means isopropyl alcohol; LDA means lithium diisopropylamide; LHMDS means lithium bis(hexamethyldisilylamide); LAH means lithium aluminum hydride; NCS means N-chlorosuccinimide; PyBOP means benzotriazol-1-yloxytripyrrolidinophosphonium hexafluorophosphate; TDA-I means tris(2-(2-methoxyethoxy)ethyl)amine; DCM means dichloromethame; TEA means triethylamine; TFA means trifluoroacetic acid; THF means tetrahydrofuran; NCS means N-chlorosuccinimide; NMM means N-methylmorpholine; NMP means N-methylpyrrolidine; PPh$_3$ means triphenylphosphine, RBF means round-bottom flask.

The following preparations and Examples illustrate the invention but do not limit it in any way. The present invention will be more readily understood by referring to the following examples which are given to illustrate the invention rather than to limit its scope.

Example 1

(±)5-(1-(2-azaspiro[3.3]heptan-6-yl)-1H-pyrazol-4-yl)-3-(1-(2,6-dichloro-3-fluorophenyl)ethoxy)pyridin-2-amine

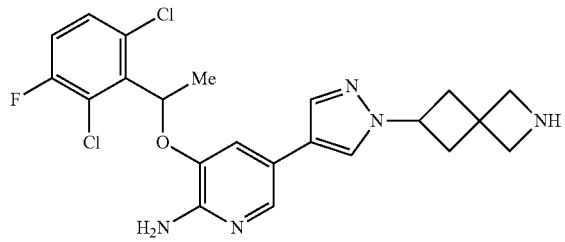 [SMILES: CC(Oc1cc(-c2cnn(C3CC4(CNC4)C3)c2)cnc1N)c1c(Cl)ccc(F)c1Cl]

Step 1 (±)1-(2,6-dichloro-3-fluorophenyl)ethanol

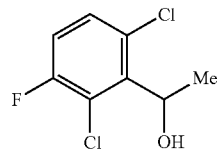 [SMILES: CC(O)c1c(Cl)ccc(F)c1Cl]

To a solution of 2',6'-dichloro-5'-fluoroacetophenone (10.4 g, 50 mmol) in MeOH (anhydrous, 80 mL) was added NaBH$_4$ (3.78 g, 100 mmol) in portions at 0° C. After the addition of NaBH$_4$, the solution was stirred at 0° C. for 10 min, then allowed to warm to room temperature and stirred at room temperature for 30 min. The reaction solution was concentrated to remove the solvent to give the residue. A saturated solution of NH$_4$Cl (60 mL) was added slowly. The aqueous phase was then extracted with EtOAc (3×65 mL). The combined organic phase was washed with H$_2$O (50 mL) and brine (50 mL), dried over anhydrous Na$_2$SO$_4$, concentrated by evaporation in vacuo to afford (±)1-(2,6-dichloro-3-fluorophenyl)ethanol (11 g, 100%) as a colorless oil.

$^1$HNMR (300 MHz, CDCl$_3$): δ 7.26 (dd, 1H), 7.02 (dd, 1H), 5.57 (m, 1H), 2.97 (d, 1H), 1.64 (d, 3H).

Step 2 (±)3-(1-(2,6,-dichloro-3-fluorophenyl)ethoxy)-2-nitropyridine

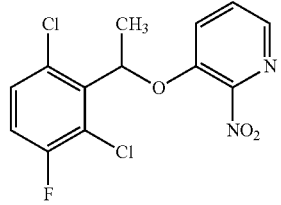

To a solution of triphenylphosphine (24.29 g, 92.6 mmol) in THF (dry, 160 mL) was added DIAD (18.23 mL, 92.6 mmol) dropwise at 0° C. under N$_2$. After addition of DIAD, a solution of 1-(2,6-dichloro-3-fluorophenyl)ethanol (13.35 g, 63.86 mmol) and 3-hydroxy-2-nitropyridine (10.29 g, 73.44 mmol) in THF (anhydrous, 160 mL) was added dropwise. The ice-bath was removed and the reaction mixture was allowed to warm to room temperature and stirred at room temperature for 4 hrs. The reaction mixture was concentrated by evaporator to give a yellow residue. A saturated solution of NH$_4$Cl (200 mL) was added. The aqueous phase was extracted with EtOAc (3×150 mL). The combined organic phase was washed with brine (2×80 mL), dried over anhydrous Na$_2$SO$_4$, concentrated by evaporation in vacuo to give a yellow residue which was purified by CombiFlash (220 g silica gel column, Hexane/EtOAc) to afford (±)-3-(1-(2,6,-dichloro-3-fluorophenyl)ethoxy)-2-nitropyridine (21.1 g, 100%) as a white solid.

$^1$HNMR (300 MHz, CDCl$_3$): δ 8.04 (d, 1H), 7.37 (m, 1H), 7.30 (dd, 1H), 7.21 (d, 1H), 7.09 (t, 1H), 6.10 (q, 1H), 1.85 (d, 3H).

Step 3 (±)-3-(1-(2,6-dichloro-3-fluorophenyl)ethoxy)pyridin-2-amine

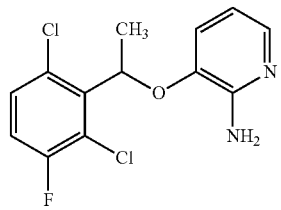 [SMILES: CC(Oc1cccnc1[N+](=O)[O-])c1c(Cl)ccc(F)c1Cl]

To a suspension of 3-(1-(2,6-dichloro-3-fluorophenyl)ethoxy)-2-nitropyridine (10 g, 30 mmol) in EtOH/AcOH (200/250 mL) was added iron powder (16.75 g, 300 mmol) in one portion. The mixture was then refluxed for 75 min. The reaction mixture was allowed to cool to room temperature. The precipitate was collected by filtration. The filtrate was concentrated by evaporator and in vacuo to give black residue. The black residue was combined with the collected solid. Water (300 mL) was added and the aqueous mixture was neutralized with Na$_2$CO$_3$, then extracted with ether (3×200 mL). The combined ethereal solution was washed with saturated NaHCO$_3$ (2×60 mL), H$_2$O (60 mL) and brine (60 mL), dried over anhydrous Na$_2$SO$_4$, concentrated by evaporator in vacuo to afford 3-(1-(2,6-dichloro-3-fluorophenyl)ethoxy)pyridin-2-amine (8.67 g, 96%) as an off-white solid.

$^{1}$HNMR (300 MHz, CDCl$_3$): δ 7.59 (d, 1H), 7.28 (dd, 1H), 7.05 (t, 1H), 6.70 (d, 1H), 6.46 (dd, 1H), 6.01 (q, 1H), 4.92 (s, br, 2H), 1.82 (d, 3H).

Step 4 (±)-5-bromo-3-(1-(2,6-dichloro-3-fluorophenyl)ethoxy)pyridin-2-amine

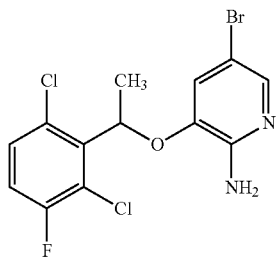 [SMILES: CC(Oc1cc(Br)cnc1N)c1c(Cl)ccc(F)c1Cl]

To a solution of 3-(1-(2,6-dichloro-3-fluorophenyl)ethoxy)pyridine-2-amine (7.49 g, 24.87 mmol) in CH$_3$CN/DCM (100/30 mL) was added NBS (4.43 g, 24.87 mmol) in portions at 0° C. The reaction solution was stirred at 0° C. for 10 min. The precipitate was removed by filtration. The black filtrate was concentrated to give a black residue which was purified by CombiFlash (80 g silica gel column, EtOAc/Hexane) to afford 5-bromo-3-(1-(2,6-dichloro-3-fluorophenyl)ethoxy)pyridin-2-amine (7.8 g, 82%) as a pale yellow solid.

$^{1}$HNMR (300 MHz, CDCl$_3$): δ 7.67 (d, 1H), 7.31 (dd, 1H), 7.08 (t, 1H), 6.83 (s, 1H), 4.83 (s, br, 2H), 1.82 (t, 3H).

Step 5 (±)-Bis(Boc) protected 5-bromo-3-(1-(2,6-dichloro-3-fluorophenyl)ethoxy)pyridin-2-amine

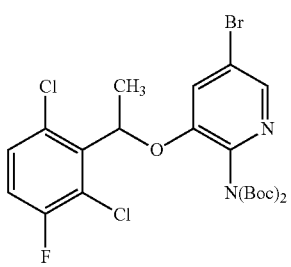

To a solution of 5-bromo-3-(1-(2,6-dichloro-3-fluorophenyl)ethoxy)pyridin-2-amine (5.7 g, 15 mmol) in dry DMF (50 mL) was added di-t-butyl dicarbonate (9.82 g, 45 mmol) and DMAP (367 mg, 3.0 mmol). The resulting yellow solution was stirred at room temperature for 18 hrs. A saturated solution of NaHCO$_3$ (150 mL) was added. The aqueous phase was extracted with EtOAc (3×100 mL). The combined organic phase was washed with H$_2$O (3×80 mL), saturated NaHCO$_3$ (80 mL), brine (80 mL), dried over anhydrous Na$_2$SO$_4$ and then concentrated to afford bis(Boc) protected 5-bromo-3-(1-(2,6-dichloro-3-fluorophenyl)ethoxy)pyridin-2-amine (8.69 g, 100%) as a foam solid.

$^{1}$HNMR (300 MHz, CDCl$_3$): δ 8.17 (s, 1H), 7.83 (s, 1H), 7.56 (m, 1H), 7.49 (t, 1H), 6.26 (q, 1H), 1.74 (d, 3H), 1.38 (s, 9H), 1.20 (s, 9H).

Step 6 (±)-bis(Boc) protected 3-(1-(2,6-dichloro-3-fluorophenyl)ethoxy)-5-(4,4,5,5-tetramethyl-1,3,2-dioxaborolan-2-yl)pyridin-2-amine

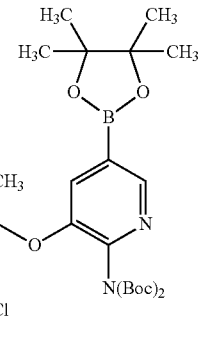

A flame dried round bottom flask was filled N$_2$. DMSO (15 mL), bis(Boc) protected 5-bromo-3-(1-(2,6-dichloro-3-fluorophenyl)ethoxy)pyridin-2-amine (4.34 g, 7.5 mmol) and bis (pinacolato)diboron (2.29 g, 9.0 mmol) and potassium acetate (2.5 g, 25.5 mmol) were added. The solution was degassed by vacuum and refilled with N$_2$. Pd(dppf)Cl$_2$.DCM (306 mg, 0.375 mmol) was added in one portion. The solution was degassed by cacuum and refilled with N$_2$ again, then stirred at 80° C. for 2 hrs. EtOAc (100 mL) was added. The mixture was passed through a pad of celite, eluted with EtOAc (100 mL). The combined organic solution was washed with H$_2$O (3×60 mL), brine (60 mL), dried over anhydrous Na$_2$SO$_4$ and concentrated by evaporator in vacuo to give the crude residue which was purified by CombiFlash (80 g silica gel, Hexane/EtOAc) to afford (±)-bis(Boc) protected 3-(1-(2,6-dichloro-3-fluorophenyl)ethoxy)-5-(4,4,5,5-tetramethyl-1,3,2-dioxaborolan-2-yl)pyridin-2-amine (3.83 g, 81%) as a foam.

$^{1}$HNMR (300 MHz, CDCl$_3$): δ 8.38 (s, 1H), 7.53 (s, 1H), 7.28 (dd, 1H), 7.04 (t, 1H), 6.11 (q, 1H), 1.79 (d, 3H), 1.39 (m, 32H).

Step 7 (±)-3-(1-(2,6-dichloro-3-fluorophenyl)ethoxy)-5-(4,4,5,5-tetramethyl-1,3,2-dioxaborolan-2-yl)pyridin-2-amine

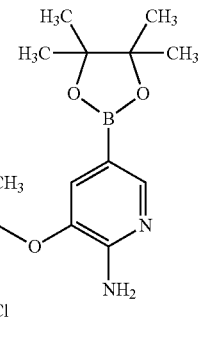

To a solution of (±)-bis(Boc) protected 3-(1-(2,6-dichloro-3-fluorophenyl)ethoxy)-5-(4,4,5,5-tetramethyl-1,3,2-dioxaborolan-2-yl)pyridin-2-amine (3.83 g, 6.1 mmol) in DCM (15 mL) was added a solution of HCl in dioxane (4.0 N, 7.6 mL). The solution was stirred at room temperature for 18 hrs and 40° C. for 8 hrs. The solution was concentrated to give the residue which was dissolved in EtOAc (180 mL). The solution was washed with saturated NaHCO₃ solution (2×50 mL), brine (50 mL), dried over anhydrous Na₂SO₄, and then concentrated by evaporator in vacuo to afford (±)-3-(1-(2,6-dichloro-3-fluorophenyl)ethoxy)-5-(4,4,5,5-tetramethyl-1,3,2-dioxaborolan-2-yl)pyridin-2-amine (2.6 g, 100%) as a pale yellow solid.

¹HNMR (300 MHz, CDCl₃): δ 8.01 (s, 1H), 7.27 (dd, 1H), 7.17 (s, 1H), 7.06 (t, 1H), 6.12 (q, 1H), 5.02 (s, br, 2H), 1.81 (d, 3H), 1.30 (s, 6H), 1.28 (s, 6H).

Step 8 tert-butyl 6-hydroxy-2-azaspiro[3.3]heptane-2-carboxylate

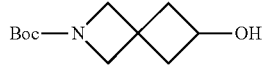

To a solution of tert-butyl 6-oxo-2-azaspiro[3.3]heptane-2-carboxylate (507 mg, 2.4 mmol) in MeOH (5.0 mL) was added NaBH₄ (182 mg, 4.8 mmol) at 0° C. under N₂. It was stirred at 0° C. for 30 min. The solution was concentrated by evaporator in vacuo to give crude solid. A saturated solution of NaHCO₃ (30 mL) was added. The aqueous mixture was extracted with DCM (4×30 mL). The combined organic solution was dried over anhydrous Na₂SO₄ and then concentrated by evaporation in vacuo to afford tert-butyl 6-hydroxy-2-azaspiro[3.3]heptane-2-carboxylate (511 mg, 100%) as a white solid.

¹HNMR (300 MHz, CDCl₃): δ 4.18 (m, 1H), 3.88 (d, 4H), 2.53 (m, 2H), 2.08 (m, 2H), 1.42 (s, 9H).

Step 9 tert-butyl 6-((methylsulfonyl)oxy)-2-azaspiro[3.3]heptane-2-carboxylate

tert-Butyl 6-hydroxy-2-azaspiro[3.3]heptane-2-carboxylate (505 mg, 2.37 mmol) was dissolved in DCM (6.0 mL). The solution was cooled to 0° C. with an external ice-bath. Et₃N (330 µL, 2.37 mmol) and DMAP (3.0 mg, 0.0237 mmol) were added. Methanesulfonyl chloride (184 µL, 2.37 mmol) was then added dropwise by syringe. The solution was stirred at 0° C. for 2.0 hrs, was then allowed to warm to room temperature and stirred at room temperature for 18 hrs. A saturated solution of NH₄Cl (20 mL) was added and stirred at room temperature for 10 min. The layers were separated. The aqueous phase was extracted with DCM (3×30 mL). The combined organic phase was dried over anhydrous Na₂SO₄, concentrated by evaporation in vacuo to afford tert-butyl 6-((methylsulfonyl)oxy)-2-azaspiro[3.3]heptane-2-carboxylate (684 mg, 99%) as a white solid.

¹HNMR (300 MHz, CDCl₃): δ 4.89 (m, 1H), 3.93 (s, 4H), 2.99 (s, 3H), 2.68 (m, 1H), 2.48 (m, 2H), 1.43 (s, 9H).

Step 10 tert-butyl 6-(4-bromo-1H-pyrazol-1-yl)-2-azaspiro[3.3]heptane-2-carboxylate

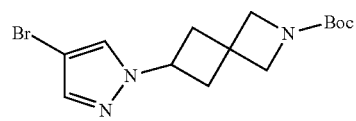 [SMILES: CC(C)(C)OC(=O)N1CC2(CC(n3cc(Br)cn3)C2)C1]

To a solution of 4-bromopyrazole (111 mg, 0.755 mmol) in DMF (dry, 2.5 mL) was added NaH (60 wt % in oil, 33 mg, 0.82 mmol) in portions at 0° C. under N₂. The mixture was stirred at 0° C. for 15 min, the ice-bath was removed. The mixture was stirred at room temperature for 90 min. tert-butyl 6-((methylsulfonyl)oxy)-2-azaspiro[3.3]heptane-2-carboxylate (200 mg, 0.686 mmol) was added in one portion. The mixture was stirred at room temperature for 1 h, then 80° C. for 18 hrs. The mixture was concentrated in vacuo to give the residue which was dissolved in DCM (30 mL). A saturated solution of NH₄Cl (30 mL) was added. The layers were separated. The aqueous phase was extracted with DCM (2×30 mL). The combined organic phase was dried over anhydrous Na₂SO₄ and then concentrated to give the crude residue which was purified by CombiFlash (40 g silica gel column, Hexane/EtOAc) to afford tert-butyl 6-(4-bromo-1H-pyrazol-1-yl)-2-azaspiro[3.3]heptane-2-carboxylate (74 mg, 31%) as a white solid.

¹HNMR (300 MHz, CDCl₃): δ 7.46 (s, 1H), 7.39 (s, 1H), 4.58 (m, 1H), 4.00 (s, 2H), 3.93 (s, 2H), 2.69 (d, 4H), 1.42 (s, 9H).

Step 11 (±)-tert-butyl 6-(4-(6-amino-5-(1-(2,6-dichloro-3-fluorophenyl)ethoxy)pyridin-3-yl)-1H-pyrazol-1-yl)-2-azaspiro[3.3]heptane-2-carboxylate

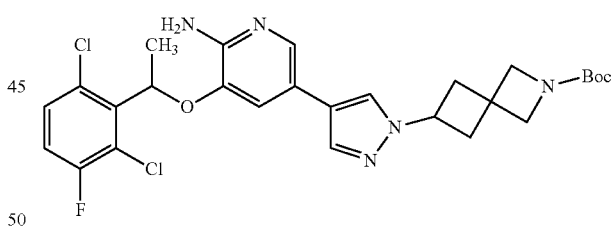

tert-Butyl 6-(4-bromo-1H-pyrazol-1-yl)-2-azaspiro[3.3]heptane-2-carboxylate (145 mg, 0.42 mmol) and (±)-3-(1-(2,6-dichloro-3-fluorophenyl)ethoxy)-5-(4,4,5,5-tetramethyl-1,3,2-dioxaborolan-2-yl)pyridin-2-amine (268 mg, 0.63 mmol) were added to a round bottom flask. It was vacuumed and refilled with N₂ (3 times). DME (2.0 mL) and a solution of Na₂CO₃ (2.0 M, 1.0 mL) were sequentially added. It was vacuumed and refilled with N₂ (3 times). Pd(PPh₃)₂Cl₂ (14.7 mg, 0.021 mmol) was added. It was degassed again refilled with N₂ (2 times). The mixture was stirred at 90° C. (heating bath) for 16 hrs. The reaction mixture was cooled to room temperature and H₂O (30 mL) was added. The aqueous phase was extracted with EtOAc (30 mL) and DCM (3×30 mL). The combined organic phase was dried over anhydrous Na₂SO₄, concentrated by evaporation in vacuo to give black residue which was purified by CombiFlash (40 g silica gel column, Hexane/EtOAc) to afford (±)-tert-butyl 6-(4-(6-amino-5-(1-(2,6-dichloro-3-fluorophenyl)ethoxy)pyridin-3-yl)-1H-pyrazol-1-yl)-2-azaspiro[3.3]heptane-2-carboxylate (106 mg, 45%) as a off-white solid.

¹HNMR (300 MHz, CDCl₃): δ 7.74 (d, 1H), 7.58 (s, 1H), 7.44 (s, 1H), 7.30 (m, 1H), 7.05 (t, 1H), 6.85 (d, 1H), 6.06 (q, 1H), 4.80 (s, 2H), 4.63 (m, 1H), 4.04 (s, 2H), 3.97 (s, 2H), 2.75 (m, 4H), 1.85 (d, 3H), 1.45 (s, 9H).

Step 12 (±)-5-(1-(2-azaspiro[3.3]heptan-6-yl)-1H-pyrazol-4-yl)-3-(1-(2,6-dichloro-3-fluorophenyl)ethoxy)pyridin-2-amine formate

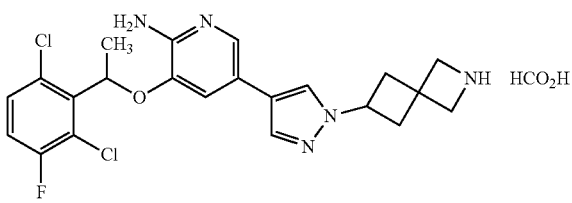 [SMILES: CC(Oc1cc(-c2cnn(C3CC4(CNC4)C3)c2)cnc1N)c1c(Cl)ccc(F)c1Cl ; "HCO2H"]

tert-Butyl 6-(4-(6-amino-5-(1-(2,6-dichloro-3-fluorophenyl)ethoxy)pyridin-3-yl)-1H-pyrazol-1-yl)-2-azaspiro[3.3]heptane-2-carboxylate (53 mg, 0.094 mmol) was dissolved in formic acid (3 mL). The solution was sonicated at room temperature for 1.0 h and then concentrated by evaporation in vacuo to give the residue. Toluene (2×5 mL) was added and evaporated again. Ether (10 mL) was added and the mixture was stirred at room temperature for 1.0 h. The solid was collected by filtration, washed with ether (10 mL) and then dried under high vacuum to afford (±)-5-(1-(2-azaspiro[3.3]heptan-6-yl)-1H-pyrazol-4-yl)-3-(1-(2,6-dichloro-3-fluorophenyl)ethoxy)pyridin-2-amine formate (29 mg, 61%) as an off-white solid.

¹HNMR (300 MHz, CD₃OD): δ 8.49 (s, 1H), 7.76 (s, 1H), 7.65 (s, 1H), 7.58 (s, 1H), 7.44 (dd, 1H), 7.23 (t, 1H), 6.92 (s, 1H), 6.17 (q, 1H), 4.77 (m, 1H), 4.20 (s, 2H), 4.14 (s, 2H), 2.82 (m, 4H), 1.87 (d, 3H).

Example 2

(R)-5-(1-(2-azaspiro[3.3]heptan-6-yl)-1H-pyrazol-4-yl)-3-(1-(2,6-dichloro-3-fluorophenyl)ethoxy)pyridin-2-amine

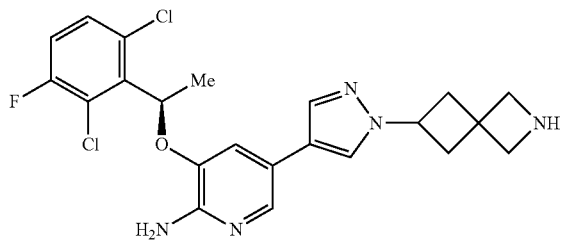 [SMILES: C[C@@H](Oc1cc(-c2cnn(C3CC4(CNC4)C3)c2)cnc1N)c1c(Cl)ccc(F)c1Cl]

Step 1 (S)1-(2,6-dichloro-3-fluorophenyl)ethanol

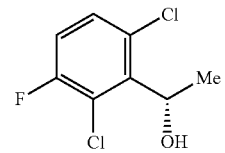

To (R)-2-methyl-CBS-oxazaborolidine (Aldrich or Callery Chemical Co, 1M in toluene, 1 eq.) at −45° C. is added BH3. Me2S (1.06 eq.). To the previous solution is added at −30° C. a 1M dichloromethane solution of 1-(2,6-dichloro-3-fluorophenyl)ethanone. After completion of the reaction, excess MeOH is added followed by 1N HCl. After warming up to room temperature, the resulting mixture is filtered through a pad of celite and silica gel and washed with 30% EtOAc in hexane. The solvent is removed under reduced pressure and the resulting oil is purified by flash chromatography (20% EtOAc in hexane) to afford (S)-1-(2,6-dichloro-3-fluorophenyl)ethanol (optically enriched).

Step 2 (R)-5-(1-(2-azaspiro[3.3]heptan-6-yl)-1H-pyrazol-4-yl)-3-(1-(2,6-dichloro-3-fluorophenyl)ethoxy)pyridin-2-amine can be prepared by following the procedures described for Example 1.

Example 3

(R)-5-(1-(7-azaspiro[3.5]nonan-2-yl)-1H-pyrazol-4-yl)-3-((R)-1-(2,6-dichloro-3-fluorophenyl)ethoxy)pyridin-2-amine

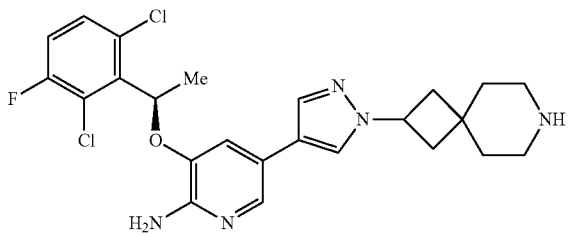 [SMILES: C[C@@H](Oc1cc(-c2cnn(C3CC4(CCNCC4)C3)c2)cnc1N)c1c(Cl)ccc(F)c1Cl]

Step 1 tert-butyl 4-methylenepiperidine-1-carboxylate

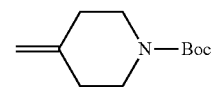

To a suspension of methyltriphenylphosphonium bromide (36.3 g, 101.6 mmol, 1.35 equiv) in ether (dry, 300 mL) was added potassium t-butoxide (11 g, 98 mmol, 1.3 equiv) in one portion at 0° C. under nitrogen balloon. The mixture was then stirred at reflux for 2 hrs. The hot reaction mixture was cooled to 0° C. with an external ice-bath and then a solution of tert-butyl 4-oxopiperidine-1-carboxylate (15 g, 75.3 mmol, 1.0 equiv) in ether (60 mL) was added dropwise. The mixture was allowed to warm to room temperature and stirred at room temperature for 1 h. The mixture was then stirred at reflux overnight (16 h). The mixture was cooled to room temperature and hexane (300 mL) was added. The mixture was stirred for 10 min, filtered and eluted with Hexane/EtOAc (100/100 mL). The combined organic solution was concentrated to give the residue which was purified by CombiFlash (100 g silica gel column, EtOAc/Hex=0-30%) to afford 14 g (yield 94%) of tert-butyl 4-methylenepiperidine-1-carboxylate as a colorless oil.

¹HNMR (400 MHz, CDCl₃): δ 4.74 (s, 2H), 3.42 (t, 4H), 2.18 (t, 4H), 1.47 (s, 9H).

Step 2 tert-butyl 2-oxo-7-azaspiro[3.5]nonane-7-carboxylate

To a flame-dried RB flask with tert-butyl 4-methylenepiperidine-1-carboxylate (2.96 g, 15 mmol, 1.0 equiv) and Zn/Cu couple (6.54 g, 172.5 mmol, 11.5 equiv) under vacuum, t-BuOMe (60 mL) was charged and refilled the flask with N₂ balloon. To the mixture thus obtained stirred at 15° C., a solution of 2,2,2-trichloroacetyl chloride in DME (20 mL) was added dropwise. The mixture was stirred at room temperature overnight after addition. To the reaction mixture stirred in an external ice-bath, a saturated solution of NH₄Cl (60 mL) was added slowly and carefully (especially the first few drops). After addition, the mixture was stirred at room temperature for 4 h, filtered to remove the solid. The phases were separated. The aqueous phase was extracted with EtOAc. The combined organic phase was washed with brine, dried over anhydrous Na₂SO₄, concentrated to give the residue which was purified by CombiFlash (40 g silica gel column, EtOAc/Hexane: 0-40%) to afford 619 mg (15%) of tert-butyl 2-oxo-7-azaspiro[3.5]nonane-7-carboxylate.

¹H NMR (CDCl₃, 300 MHz): δ3.41 (t, 4H), 2.82 (s, 4H), 1.70 (t, 4H), 1.47 (s, 9H).

Step 3 tert-butyl 2-hydroxy-7-azaspiro[3.5]nonane-7-carboxylate

To a solution of tert-butyl 2-oxo-7-azaspiro[3.5]nonane-7-carboxylate (600 mg, 2.5 mmol, 1.0 equiv) in MeOH (6.0 mL) was added sodium borohydride (190 mg, 5.0 mmol, 2.0 equiv) in portions at 0° C. under nitrogen. The mixture was stirred at room temperature for 2.0 hrs. The solution was concentrated by evaporator to give the white solid. Saturated NaHCO₃ solution (40 mL) was added. The aqueous phase was extracted with DCM (4×30 mL). The combined organic phase was dried over anhydrous Na₂SO₄, concentrated to give the crude which was purified by CombiFlash (24 g silica gel column, EtOAc/Hexane=0-60%) to afford 334 mg (yield 57%) of tert-butyl 2-hydroxy-7-azaspiro[3.5]nonane-7-carboxylate as a white solid.

¹H NMR (CDCl₃, 300 MHz): δ4.30 (m, 1H), 3.30 (m, 4H), 2.27 (m, 2H), 1.87 (d, 1H), 1.67 (m, 2H), 1.48 (m, 4H), 1.44 (s, 9H).

Step 4 tert-butyl 2-(methylsulfonyloxy)-7-azaspiro [3.5]nonane-7-carboxylate

tert-butyl 2-hydroxy-7-azaspiro[3.5]nonane-7-carboxylate (392 mg, 1.62 mmol, 1.0 equiv) was dissolved in DCM (6.0 mL). The solution was cooled to 0° C. with an external ice-bath. Et₃N (237 µL, 1.706 mmol, 1.05 equiv)) and DMAP (2.0 mg, 1 mol %) were added. Methanesulfonyl chloride (132 µL, 1.706 mmol, 1.05 equiv) was then added dropwise by a syringe. The solution was stirred at 0° C. for 2.0 hrs, was then allowed to warm to room temperature and stirred at room temperature for 18 hrs. Et₃N (23 µL, 0.1 equiv) and methanesulfonyl chloride (13 µL, 0.1 equiv) were added and the mixture was stirred for another 6 h. A saturated solution of NH₄Cl (20 mL) was added and stirred at room temperature for 10 min. The layers were separated. The aqueous phase was extracted with DCM (3×30 mL). The combined organic phase were washed with HCl (1N, 20 mL) and water (20 mL) and were dried over anhydrous Na₂SO₄, concentrated in vacuo to afford 482 mg (yield 93%) of tert-butyl 2-(methylsulfonyloxy)-7-azaspiro[3.5]nonane-7-carboxylate as a white solid.

¹H NMR (CDCl₃, 300 MHz): δ 5.04 (m, 1H), 3.33 (m, 4H), 3.00 (s, 3H), 2.43 (m, 2H), 2.08 (m, 2H), 1.56 (m, 4H), 1.45 (s, 9H).

Step 5 tert-butyl 2-(4-iodo-1H-pyrazol-1-yl)-7-azaspiro[3.5]nonane-7-carboxylate

To a solution of 4-bromopyrazole (141 mg, 0.729 mmol, 1.2 equiv) in DMF (dry, 3 mL) was added NaH (60 wt % in oil, 29 mg, 0.729 mmol, 1.2 equiv) in portions at 0° C. under N₂. The mixture was stirred at 0° C. for 15 min, the ice-bath was removed. The mixture was stirred at room temperature for 90 min. tert-butyl 2-(methylsulfonyloxy)-7-azaspiro[3.5] nonane-7-carboxylate (200 mg, 0.607 mmol, 1.0 equiv) was added in one portion. The mixture was stirred at room temperature for 1.0 h, then 80° C. for 18 hrs. The mixture was diluted with EtOAc (30 mL) and washed with a saturated solution of NH₄Cl (30 mL). The layers were separated. The aqueous phase was extracted with EtOAc (30 mL). The combined organic phase was dried over anhydrous Na₂SO₄ and then concentrated to give the crude residue which was purified by CombiFlash (40 g silica gel column, Hexane/EtOAc) to afford 225 mg (yield 88.8%) of tert-butyl 2-(4-iodo-1H-pyrazol-1-yl)-7-azaspiro[3.5]nonane-7-carboxylate as a colorless oil.

$^1$H NMR (CDCl$_3$, 300 MHz): δ 7.53 (s, 1H), 7.46 (s, 1H), 4.76 (m, 1H), 3.40 (t, 2H), 3.32 (t, 2H), 2.42 (m, 2H), 2.30 (m, 2H), 1.62 (m, 4H), 1.45 (s, 9H).

Step 6 tert-butyl 2-(4-(6-amino-5-((R)-1-(2,6-dichloro-3-fluorophenyl)ethoxy)pyridin-3-yl)-1H-pyrazol-1-yl)-7-azaspiro[3.5]nonane-7-carboxylate

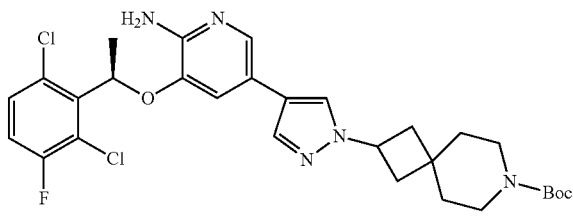 [SMILES: C[C@@H](Oc1cc(-c2cnn(C3CC4(CCN(C(=O)OC(C)(C)C)CC4)C3)c2)cnc1N)c1c(Cl)ccc(F)c1Cl]

(R)-3-(1-(2,6-dichloro-3-fluorophenyl)ethoxy)-5-(4,4,5,5-tetramethyl-1,3,2-dioxaborolan-2-yl)pyridin-2-amine (104 mg, 0.244 mmol, 1.0 equiv), tert-butyl 2-(4-iodo-1H-pyrazol-1-yl)-7-azaspiro[3.5]nonane-7-carboxylate (112 mg, 0.268 mmol, 1.1 equiv) were added to a RBF (25 mL). It was vacuumed and refilled with N$_2$ (3 times). Dioxane (1.0 mL) and a solution of Na$_2$CO$_3$ (2.0 M, 0.4 mL) were added sequentially. It was vacuumed again and refilled with N$_2$ (3 times). Pd(PPh$_3$)$_2$Cl$_2$ catalyst (9 mg, 5 mol %) was added last. It was vacuumed and refilled with N$_2$ (3 times). The mixture was then heated to 80° C. (oil bath) and stirred at this temperature under N$_2$ for 24 hrs. The mixture was cooled to room temperature, and concentrated to give black residue which was treated with H$_2$O (30 mL). The aqueous phase was extracted with EtOAc (4×30 mL). The combined organic phase was washed with brine (30 mL), dried over anhydrous Na$_2$SO$_4$, concentrated to give black green residue which was purified by CombiFlash (12 g silica gel column; EtOAc/Hexane: 0-100%) to afford 105 mg (yield 73%) of (R)-tert-butyl 2-(4-(6-amino-5-(1-(2,6-dichloro-3-fluorophenyl)ethoxy)pyridin-3-yl)-1H-pyrazol-1-yl)-7-azaspiro[3.5]nonane-7-carboxylate as a pale yellow solid.

$^1$H NMR (CDCl$_3$, 300 MHz): δ 7.75 (s, 1H), 7.59 (s, 1H), 7.48 (s, 1H), 7.29 (m, 1H), 7.04 (t, 1H), 6.86 (s, 1H), 6.06 (q, 1H), 4.87 (s, br, 2H), 4.75 (t, 1H), 3.42 (t, 2H), 3.34 (t, 2H), 2.44 (m, 2H), 2.34 (m, 2H), 1.85 (d, 3H), 1.66 (m, 4H), 1.46 (s, 9H).

Step 7 (R)-5-(1-(7-azaspiro[3.5]nonan-2-yl)-1H-pyrazol-4-yl)-3-((R)-1-(2,6-dichloro-3-fluorophenyl)ethoxy)pyridin-2-amine

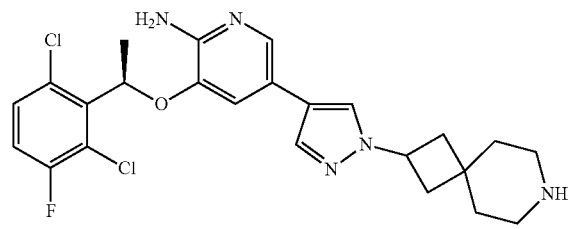 [SMILES: C[C@@H](Oc1cc(-c2cnn(C3CC4(CCNCC4)C3)c2)cnc1N)c1c(Cl)ccc(F)c1Cl]

(R)-tert-butyl 2-(4-(6-amino-5-(1-(2,6-dichloro-3-fluorophenyl)ethoxy)pyridin-3-yl)-1H-pyrazol-1-yl)-7-azaspiro[3.5]nonane-7-carboxylate (105 mg, 0.178 mmol, 1.0 equiv) was dissolved in formic acid (6 mL). The solution was sonicated at room temperature for 90 min (the temperature of sonication bath reached about 40° C. after 90 min). The solution was cooled to room temperature and concentrated by rotavapor to give the residue which was dissolved in EtOAc (20 mL). A solution of Na$_2$CO$_3$ (2.0 M, 20 mL) was added. The mixture was stirred at room temperature for 30 min. H$_2$O (10 mL) was added. The layers were separated. The aqueous phase was extracted with DCM (3×30 mL). The combined organic phase was washed with brine (30 mL), dried over anhydrous Na$_2$SO$_4$, concentrated to give pale yellow solid which was purified by CombiFlash [12 g silica gel column; (MeOH/NH$_4$OH=10/1)/DCM: 0-20%] to afford 77 mg (yield 88%) of (R)-5-(1-(7-azaspiro[3.5]nonan-2-yl)-1H-pyrazol-4-yl)-3-(1-(2,6-dichloro-3-fluorophenyl)ethoxy)pyridin-2-amine as a off-white foam solid.

$^1$H NMR (CDCl$_3$, 300 MHz): δ 7.76 (s, 1H), 7.59 (s, 1H), 7.49 (s, 1H), 7.29 (m, 1H), 7.05 (t, 1H), 6.86 (s, 1H), 6.07 (q, 1H), 4.76 (s, 2H), 4.74 (t, 1H), 2.86 (t, 2H), 2.79 (t, 2H), 2.36 (m, 5H), 1.85 (d, 3H), 1.68 (m, 4H).

Example 4

(R)-5-(1-(2-azaspiro[3.5]nonan-7-yl)-1H-pyrazol-4-yl)-3-((R)-1-(2,6-dichloro-3-fluorophenyl)ethoxy)pyridin-2-amine

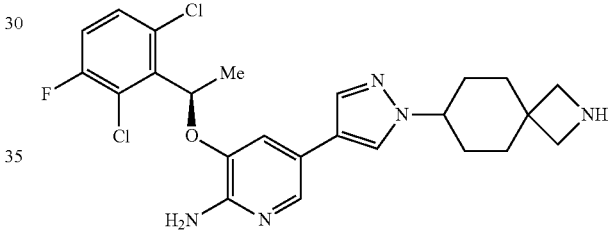

Step 1 4-(benzyloxy)cyclohexanecarboxamide

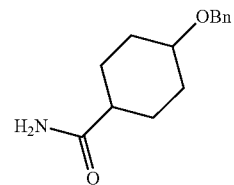 [SMILES: NC(=O)C1CCC(OCc2ccccc2)CC1]

To a solution of 4-(benzyloxy)cyclohexanecarboxylic acid (5.4 g, 23 mmol, 1.0 equiv) and triethylamine (4.82 mL, 34.57 mmol, 1.5 equiv) in DCM (dry, 40 mL) was added ethyl chloroformate (3.0 mL, 31.1 mmol, 1.35 equiv) dropwise between −20 and −10° C. under N$_2$. The white precipitate appeared. The mixture was stirred at about −15° C. for 10 min, dried NH$_3$ was bubbled rapidly into the liquid for 20 min. The mixture was stirred at −15° C. for 30 min, then put into the fridge (−20° C.) overnight. The flask was released the pressure and warm to room temperature. H$_2$O (100 mL) was added. The layer was separated and the aqueous phase was extracted with DCM (3×100 mL). The combined organic solution was washed with brine (50 mL), dried over anhydrous Na$_2$SO$_4$, concentrated to give 5.2 g (96.7%) of 4-(benzyloxy)cyclohexanecarboxamide as a off-white solid.

$^1$H NMR (CDCl$_3$, 300 MHz): δ 7.31 (m, 5H), 5.55 (m, 2H), 4.56 (s, 2H), 3.35 (m, 1H), 2.17 (m, 3H), 1.98 (m, 2H), 1.50 (2H), 1.33 (m, 2H).

Step 2 4-(benzyloxy)cyclohexanecarbonitrile

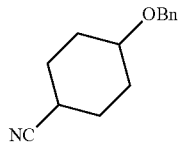 [SMILES: N#CC1CCC(OCc2ccccc2)CC1]

To a suspension of 4-(benzyloxy)cyclohexanecarboxamide (2.33 g, 10 mmol, 1.0 equiv) in THF (dry, 50 mL) was added trifluoroacetic anhydride (4.16 mL, 30 mmol, 3.0 equiv) dropwise at room temperature. The resulting clear solution was stirred at room temperature for 30 min and then concentrated to give the residue. H$_2$O (50 mL) was added. The aqueous phase was extracted with MTBE (3×50 mL). The combined organic solution was washed with brine (50 mL), dried over anhydrous Na$_2$SO$_4$, concentrated to give 2.1 g (yield 97%) of 4-(benzyloxy)cyclohexanecarbonitrile as a pale yellow oil.

$^1$H NMR (CDCl$_3$, 300 MHz): δ 7.33 (m, 5H), 4.52 (s, 2H), 3.48 (m, 1H), 2.60 (m, 1H), 2.04 (m, 4H), 1.65 (m, 4H).

Step 3 ethyl 4-(benzyloxy)-1-cyanocyclohexanecarboxylate

To a solution of 4-(benzyloxy)cyclohexanecarbonitrile (1.26 g, 5.85 mmol, 1.0 equiv) in THF (dry, 30 mL) was added a solution of LDA (3.95 mL, 2.0 M Heptane/THF/toluene, 1.35 equiv) dropwise at −78° C. under N$_2$. The resulting yellow solution was stirred at −78° C. for 2 hrs. Ethyl chloroformate (2.79 mL, 29.26 mmol, 5.0 equiv) was then added by syringe dropwise. The solution was stirred at −78° C. and allowed to warm to room temperature slowly and stirred overnight. The reaction was quenched by addition of H$_2$O (20 mL), HCl (1.0 N, 20 mL). It was then extracted with EtOAc (3×40 mL). The combined organic solution was washed with brine (50 mL), dried over anhydrous Na$_2$SO$_4$ and then concentrated to give pale yellow residue. Ether (40 mL) was added and stirred for 5 min, filtered to remove the white solid. The ethereal solution was concentrated to give the yellow oil which was purified by CombiFlash (25 g silica gel column, EtOAc/Hexane: 0-20%) to afford 565 mg (yield 33%) of ethyl 4-(benzyloxy)-1-cyanocyclohexanecarboxylate as a pale yellow oil.

$^1$H NMR (CDCl$_3$, 300 MHz): δ 7.34 (m, 5H), 4.57 (s, 2H), 4.26 (q, 2H), 3.38 (m, 1H), 2.14 (m, 4H), 1.87 (m, 4H), 1.32 (t, 3H).

Step 4 4-(benzyloxy)-1-(hydroxymethyl)cyclohexanecarbonitrile

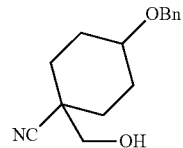 [SMILES: N#CC1(CO)CCC(OCc2ccccc2)CC1]

To a solution of sodium borohydride (186 mg, 4.92 mmol, 2.5 equiv) in THF/H$_2$O (5/0.5 mL) was added a solution of ethyl 4-(benzyloxy)-1-cyanocyclohexanecarboxylate (565 mg, 1.97 mmol, 1.0 equiv) in THF (dry, 3 mL) dropwise. The reaction mixture was stirred at room temperature for 18 hrs. It was concentrated to give the white solid. H$_2$O (20 mL) was added. The aqueous phase was extracted with EtOAc (4×30 mL). The combined organic solution was washed with brine (30 mL), dried over anhydrous Na$_2$SO$_4$ and then concentrated to give 565 mg of crude 4-(benzyloxy)-1-(hydroxymethyl) cyclohexanecarbonitrile as a colorless sticky oil which was not purified and submitted for the next reaction.

Step 5 (4-(benzyloxy)-1-cyanocyclohexyl)methyl 4-methylbenzenesulfonate

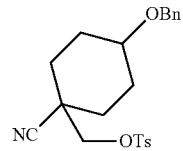 [SMILES: Cc1ccc(S(=O)(=O)OCC2(C#N)CCC(OCc3ccccc3)CC2)cc1]

To a solution of 4-(benzyloxy)-1-(hydroxymethyl)cyclohexanecarbonitrile (crude 770 mg, 1.0 equiv) in DCM (7 mL) was added p-toluenesulfonyl chloride (898 mg, 1.5 equiv), triethylamine (1.44 mL, 3.3 equiv) and DMAP (38 mg, 0.1 equiv). The solution was stirred at room temperature overnight. It was concentrated to give the residue. EtOAc (120 mL) was added. The organic solution was washed with saturated NaHCO$_3$ (30 mL), H$_2$O (30 mL) and HCl (1.0 N, 30 mL), brine (30 mL), dried over anhydrous Na$_2$SO$_4$ and then concentrated to give yellow solid which was purified by CombiFlash (24 g silica gel column, EtOAc/Hexane: 0-30%) to afford 450 mg (yield 36%) of (4-(benzyloxy)-1-cyanocyclohexyl)methyl 4-methylbenzenesulfonate as a white solid.

$^1$H NMR (CDCl$_3$, 300 MHz): δ 7.81 (d, 2H), 7.33 (m, 7H), 4.55 (s, 2H), 3.95 (s, 2H), 3.30 (m, 1H), 2.46 (s, 3H), 2.07 (t, 4H), 1.66 (m, 2H), 1.38 (m, 2H).

Step 6 tert-butyl 7-(benzyloxy)-2-azaspiro[3.5]nonane-2-carboxylate

To a solution of (4-(benzyloxy)-1-cyanocyclohexyl)methyl 4-methylbenzenesulfonate (450 mg, 1.126 mmol, 1.0 equiv) in THF (dry, 10 mL) was added LiAlH₄ (51 mg, 1.352 mmol, 1.2 equiv) in portions at 0° C. under nitrogen. After addition, the reaction mixture was allowed to warm to room temperature slowly. The reaction mixture was stirred at room temperature for 4 hrs and was then cooled to about 0° C. with an external ice-H₂O bath. H₂O (0.05 mL), a solution of NaOH (0.05 mL, 15 wt %) and H₂O (0.1 mL) were added sequentially (be careful!). After addition, the mixture was stirred at room temperature for 10 min, then passed through a pad of celite, eluted with THF (40 mL). The combined organic phase was dried over anhydrous Na₂SO₄, concentrated to give pale yellow liquid which was dissolved in DCM (10 mL), Boc anhydride (295 mg, 1.352 mmol, 1.2 equiv) was added in one portion. The solution was stirred at room temperature for 16 h. The mixture was concentrated to remove DCM. A solution of Na₂CO₃ (10 mL, 2.0 M) and a saturated solution of NaHCO₃ (10 mL) was added. The mixture was stirred at room temperature for 10 min, then extracted with EtOAc (3×30 mL). The combined organic solution was washed with brine (20 mL), dried over anhydrous Na₂SO₄, concentrated to give pale yellow oil which was purified by CombiFlash (24 g silica gel column, EtOAc/Hexane: 0-25%) to afford 290 mg (yield 77%) of tert-butyl 7-(benzyloxy)-2-azaspiro[3.5]nonane-2-carboxylate as a colorless oil.

¹H NMR (CDCl₃, 300 MHz): δ 7.33 (m, 5H), 4.53 (s, 2H), 3.60 (s, 2H), 3.57 (s, 2H), 3.38 (m, 1H), 1.88 (m, 4H), 1.49 (m, 4H), 1.44 (s, 9H).

Step 7 tert-butyl 7-hydroxy-2-azaspiro[3.5]nonane-2-carboxylate

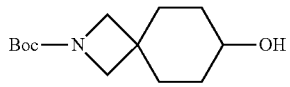 [SMILES: CC(C)(C)OC(=O)N1CC2(CCC(O)CC2)C1]

To a solution of tert-butyl 7-(benzyloxy)-2-azaspiro[3.5]nonane-2-carboxylate (290 mg, 0.96 mmol, 1.0 equiv) in MeOH (8 mL) was added Pd(OH)₂ (43.5 mg, 15 wt %). The mixture was carefully vacuumed and refilled with Hydrogen. The mixture was then stirred at room temperature under hydrogen balloon for 2 hrs. The mixture was passed through a pad of celite and eluted with MeOH (50 mL). The combined methanol solution was concentrated to afford 218 mg (yield 94%) of tert-butyl 7-hydroxy-2-azaspiro[3.5]nonane-2-carboxylate as a pale yellow solid.

¹H NMR (CDCl₃, 300 MHz): δ 3.20 (m, 1H), 3.61 (s, 2H), 3.57 (s, 2H), 1.86 (m, 3H), 1.51 (m, 2H), 1.44 (s, 9H), 1.35 (m, 3H).

Step 8 tert-butyl 7-(methylsulfonyloxy)-2-azaspiro[3.5]nonane-2-carboxylate

The title compound was prepared from tert-butyl 7-hydroxy-2-azaspiro[3.5]nonane-2-carboxylate under the conditions described in Step 4 of Example 3.

¹H NMR (CDCl₃, 300 MHz): δ 4.75 (m, 1H), 3.62 (s, 2H), 3.59 (s, 2H), 3.01 (s, 3H), 1.90 (m, 4H), 1.65 (m, 4H), 1.44 (s, 9H).

Step 9 tert-butyl 7-(4-iodo-1H-pyrazol-1-yl)-2-azaspiro[3.5]nonane-2-carboxylate

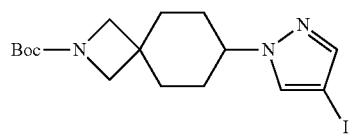 [SMILES: CC(C)(C)OC(=O)N1CC2(CCC(n3cc(I)cn3)CC2)C1]

To a solution of 4-iodo-1H-pyrazole and tert-butyl 7-(methylsulfonyloxy)-2-azaspiro[3.5]nonane-2-carboxylate (70 mg, 0.219 mmol, 1.0 equiv) and 4-iodo-1H-pyrazole in DMF (1 mL) was added Cs₂CO₃ (79 mg, 0.241 mmol, 1.1 equiv). The mixture was stirred at 80° C. for 3 hrs. It was concentrated by rotary evaporator in vacuo to give the residue which was purified by CombiFlash (12 g silica gel column, EtOAc/Hex: 0-40%) to afford 74 mg (yield 81%) of tert-butyl 7-(4-iodo-1H-pyrazol-1-yl)-2-azaspiro[3.5]nonane-2-carboxylate as a off-white solid.

¹H NMR (CDCl₃, 400 MHz): δ 7.50 (s, 1H), 7.44 (s, 1H), 4.08 (m, 1H), 3.69 (s, 2H), 3.62 (s, 2H), 2.07 (m, 4H), 1.64 (m, 4H), 1.45 (s, 9H).

Step 10 tert-butyl 7-(4-(6-amino-5-((R)-1-(2,6-dichloro-3-fluorophenyl)ethoxy)pyridin-3-yl)-1H-pyrazol-1-yl)-2-azaspiro[3.5]nonane-2-carboxylate

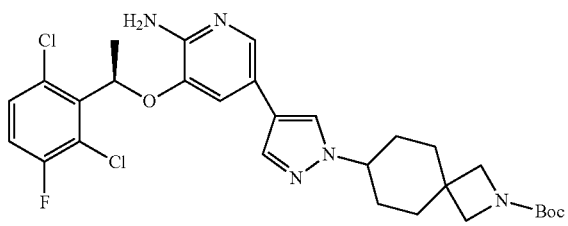 [SMILES: C[C@@H](Oc1cc(-c2cnn(C3CCC4(CC3)CN(C(=O)OC(C)(C)C)C4)c2)cnc1N)c1c(Cl)ccc(F)c1Cl]

The title compound was prepared as a off-white solid from (R)-3-(1-(2,6-dichloro-3-fluorophenyl)ethoxy)-5-(4,4,5,5-tetramethyl-1,3,2-dioxaborolan-2-yl)pyridin-2-amine and tert-butyl 7-(4-iodo-1H-pyrazol-1-yl)-2-azaspiro[3.5]nonane-2-carboxylate under the conditions described in Step 6 of Example 3.

¹H NMR (CDCl₃, 400 MHz): δ 7.75 (d, 1H), 7.58 (d, 1H), 7.46 (s, 1H), 7.29 (m, 1H), 7.05 (m, 1H), 6.87 (d, 1H), 6.08 (q, 1H), 4.85 (s, 2H), 4.83 (m, 1H), 3.72 (s, 2H), 3.63 (s, 2H), 2.09 (m, 4H), 1.85 (d, 3H), 1.80 (m, 2H), 1.64 (m, 2H), 1.45 (s, 9H).

Step 11 5-(1-(2-azaspiro[3.5]nonan-7-yl)-1H-pyrazol-4-yl)-3-(R)-1-(2,6-dichloro-3-fluorophenyl)ethoxy)pyridin-2-amine

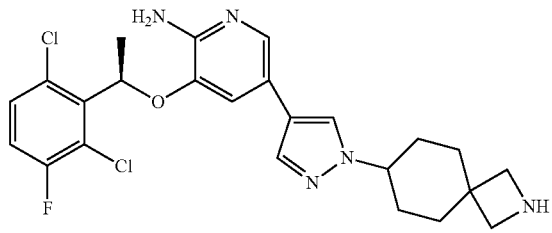 [SMILES: C[C@@H](Oc1cc(-c2cnn(C3CCC4(CC3)CNC4)c2)cnc1N)c1c(Cl)ccc(F)c1Cl]

The title compound was prepared as a off-white solid from (R)-tert-butyl 7-(4-(6-amino-5-((R)-1-(2,6-dichloro-3-fluorophenyl)ethoxy)pyridin-3-yl)-1H-pyrazol-1-yl)-2-azaspiro[3.5]nonane-2-carboxylate under the conditions described in Step 7 of Example 3.

$^1$H NMR (CDCl$_3$, 400 MHz): δ 7.75 (d, 1H), 7.54 (s, 1H), 7.46 (s, 1H), 7.30 (m, 1H), 7.05 (t, 1H), 6.86 (d, 1H), 6.07 (q, 1H), 4.77 (s, 2H), 4.04 (m, 1H), 3.18 (s, 2H), 3.09 (s, 2H), 2.09 (m, 4H), 1.85 (d, 3H), 1.80 (m, 2H), 1.58 (m, 2H).

LC-MS: 490 (M$^+$+H$^+$) C$_{24}$H$_{26}$Cl$_2$FN$_5$O Exact Mass: 489.15.

Example 5

((R)-5-(1-(6-azaspiro[3.5]nonan-2-yl)-1H-pyrazol-4-yl)-3-(1-(2,6-dichloro-3-fluorophenyl)ethoxy)pyridin-2-amine

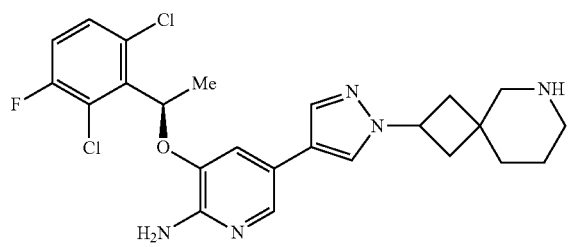 [SMILES: C[C@@H](Oc1cc(-c2cnn(C3CC4(CCCNC4)C3)c2)cnc1N)c1c(Cl)ccc(F)c1Cl]

Step 1 tert-butyl 3-oxopiperidine-1-carboxylate

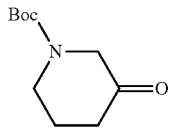

To a solution of tert-butyl 3-hydroxypiperidine-1-carboxylate (5 g, 24.84 mmol, 1.0 equiv) in DCM (125 mL) was added Dess-Martin periodinane (11.59 g, 27.33 mmol, 1.1 equiv) at 0° C. in a few portions. The solution was stirred at 0° C. for a while and allowed to warm to room temperature slowly. The solution was stirred at room temperature for 18 hrs. A lot of white solid suspended. The white solid was removed by filtration, eluted with EtOAc (100 mL). The combined organic phase was washed with saturated solution of NaHCO$_3$ (50 mL), dried over anhydrous Na$_2$SO$_4$, concentrated to afford 4.28 g (yield 86%) of tert-butyl 3-oxopiperidine-1-carboxylate as a white solid.

$^1$H NMR (CDCl$_3$, 400 MHz): δ 4.01 (s, 2H), 3.59 (t, 2H), 2.47 (t, 2H), 1.98 (m, 2H), 1.47 (s, 9H).

Step 2 tert-butyl 3-methylenepiperidine-1-carboxylate

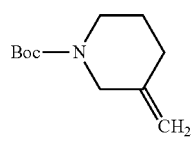

The title compound was prepared from tert-butyl 3-oxopiperidine-1-carboxylate under the conditions described in Step 1 of Example 3.

$^1$H NMR (CDCl$_3$, 400 MHz): δ 4.82 (s, 1H), 4.75 (s, 1H), 3.87 (s, 2H), 3.44 (t, 2H), 2.26 (t, 2H), 1.62 (m, 2H), 1.46 (s, 9H).

Step 3 tert-butyl 2-oxo-6-azaspiro[3.5]nonane-6-carboxylate

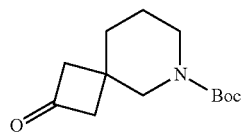 [SMILES: CC(C)(C)OC(=O)N1CCCC2(CC(=O)C2)C1]

The title compound was prepared as an oil from tert-butyl 3-methylenepiperidine-1-carboxylate under the conditions described in Step 2 of Example 3.

$^1$H NMR (CDCl$_3$, 400 MHz): δ 3.45 (s, 2H), 3.41 (t, 2H), 2.85 (m, 2H), 2.70 (m, 2H), 1.76 (t, 2H), 1.59 (m, 2H), 1.46 (s, 9H).

Step 4 tert-butyl 2-hydroxy-6-azaspiro[3.5]nonane-6-carboxylate

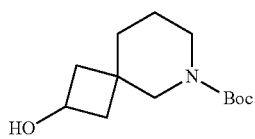

The title compound was prepared as an oil from tert-butyl 2-oxo-6-azaspiro[3.5]nonane-6-carboxylate under the conditions described in Step 3 of Example 3.

$^1$H NMR (CDCl$_3$, 400 MHz): δ 4.30 (s, br, 1H), 3.30 (s, 3H), 3.24 (s, 1H), 2.26 (m, 1H), 2.15 (m, 1H), 1.74 (m, 2H), 1.57 (m, 4H), 1.46 (s, 9H).

Step 5 tert-butyl 2-(methylsulfonyloxy)-6-azaspiro[3.5]nonane-6-carboxylate

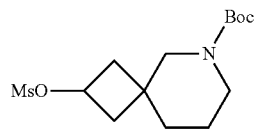

The title compound was prepared as an oil from tert-butyl 2-hydroxy-6-azaspiro[3.5]nonane-6-carboxylate under the conditions described in Step 4 of Example 3.

$^1$H NMR (CDCl$_3$, 400 MHz): δ 5.02 (m, 1H), 3.31 (m, 4H), 3.00 (s, 3H), 2.40 (m, 1H), 2.29 (m, 1H), 2.14 (m, 1H), 1.99 (m, 1H), 1.60 (m, 3H), 1.49 (m, 1H), 1.46 (s, 9H).

Step 6 tert-butyl 2-(4-bromo-1H-pyrazol-1-yl)-6-azaspiro[3.5]nonane-6-carboxylate

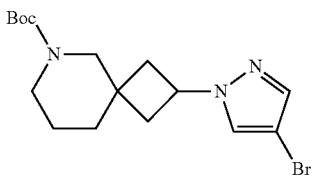 [SMILES: CC(C)(C)OC(=O)N1CCCC2(CC(n3cc(Br)cn3)C2)C1]

To a solution of 4-bromo-1H-pyrazole (210 mg, 1.428 mmol, 1.2 equiv) and tert-butyl 2-(methylsulfonyloxy)-6-azaspiro[3.5]nonane-6-carboxylate (380 mg, 1.19 mmol, 1.0 equiv) in DMF (2.5 mL) was added Cs$_2$CO$_3$ (465 mg, 1.428 mmol, 1.2 equiv). The mixture was stirred at 80° C. for 3 hrs. It was concentrated by rotary evaporator to give the residue which was purified by CombiFlash (25 g silica gel column, EtOAc/Hex: 0-40%) to afford 110 mg (yield 25%) of tert-butyl 2-(4-bromo-1H-pyrazol-1-yl)-6-azaspiro[3.5]nonane-6-carboxylate (cis and trans isomers) as a colorless oil.

LC-MS: 370 (M$^+$+H$^+$), C$_{16}$H$_{24}$BrN$_3$O$_2$ Exact Mass: 369.11

Step 7 (R)-tert-butyl 2-(4-(6-amino-5-(1-(2,6-dichloro-3-fluorophenyl)ethoxy)pyridin-3-yl)-1H-pyrazol-1-yl)-6-azaspiro[3.5]nonane-6-carboxylate

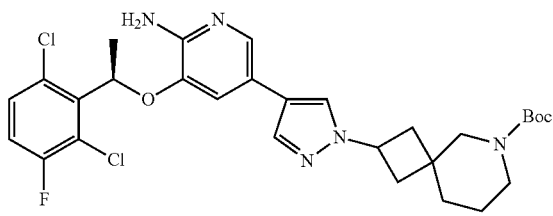 [SMILES: C[C@@H](Oc1cc(-c2cnn(C3CC4(CCCN(C(=O)OC(C)(C)C)C4)C3)c2)cnc1N)c1c(Cl)ccc(F)c1Cl]

The title compound was prepared as a pale yellow solid from (R)-3-(1-(2,6-dichloro-3-fluorophenyl)ethoxy)-5-(4,4,5,5-tetramethyl-1,3,2-dioxaborolan-2-yl)pyridin-2-amine under the conditions described in Step 6 of Example 3.

$^1$H NMR (CDCl$_3$, 400 MHz): δ 7.76 (d, 1H), 7.55 (m, 2H), 7.28 (m, 1H), 7.05 (t, 1H), 6.88 (m, 1H), 6.08 (m, 1H), 4.76 (m, 3H), 3.42 (s, 2H), 3.35 (s, 2H), 2.44-2.26 (m, 4H), 1.85 (d, 3H), 1.70 (m, 2H), 1.57 (m, 2H), 1.48, 1.45 (s, 9H).

Step 8 (R)-5-(1-(6-azaspiro[3.5]nonan-2-yl)-1H-pyrazol-4-yl)-3-(1-(2,6-dichloro-3-fluorophenyl)ethoxy)pyridin-2-amine

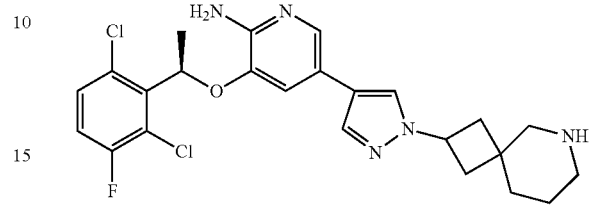

The title compound was prepared as a off-white solid from (R)-tert-butyl 2-(4-(6-amino-5-(1-(2,6-dichloro-3-fluorophenyl)ethoxy)pyridin-3-yl)-1H-pyrazol-1-yl)-6-azaspiro[3.5]nonane-6-carboxylate under the conditions described in Step 7 of Example 3.

$^1$H NMR (CDCl$_3$, 400 MHz): δ 7.76 (d, 1H), 7.58 (m, 1H), 7.48 (s, 1H), 7.29 (m, 1H), 7.05 (t, 1H), 6.86 (d, 1H), 6.06 (q, 1H), 4.79 (s, br, 2H), 4.70 (m, 1H), 2.85 (m, 2H), 2.79 (m, 2H), 2.49-2.24 (m, 4H), 1.85 (d, 3H), 1.69 (m, 2H), 1.55 (m, 2H).

LC-MS: 490 (M$^+$+H$^+$). C$_{24}$H$_{26}$Cl$_2$FN$_5$O Exact Mass: 489.15.

Biochemical Evaluation

The inhibitory activities of compounds of Formula I were assay at Reaction Biology Corporation, One Great Valley Parkway, Malvern, Pa., USA. Human ALK and cMet enzymes were used and the substrate was a peptide substrate, poly[Glu:Tyr] (4:1) at a concentration of 0.2 mg/ml. The ATP concentration for the assay was 10 μM and Staurosporine was used as a standard with an IC$_{50}$ of 2.3 nM, and 75 nM, respectively for ALK and cMet.

| Inhibitory Activities | | |
|---|---|---|
| | IC$_{50}$, nM | |
| Compound | ALK | cMet |
| Example 2 | 2.21 | 6.32 |
| Example 3 | 1.20 | 8.9 |
| Example 4 | 4.31 | 4.80 |
| Example 5 | 1.92 | 2.09 |

| Activities against ALK Mutants (IC$_{50}$) | | | | | |
|---|---|---|---|---|---|
| ALK Enzyme Inhibition IC$_{50}$, nM | | | | | |
| Compound | WT | C1156Y | F1174L | L1196M | R1275Q |
| Example 3 | 1.2 | <1.2 | 1.4 | 1.8 | 1.5 |
| Crizotinib | 2.1 nM | <1.2 nM | 2.7 nM | 7.4 nM | 2.9 nM |

While preferred embodiments have been described above and illustrated in the accompanying drawings, it will be evident to those skilled in the art that modifications may be made without departing from this disclosure. Such modifications are considered as possible variants comprised in the scope of the disclosure.

What is claimed is:

1. A compound of Formula I

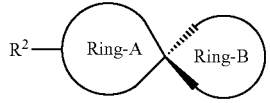

or a pharmaceutically acceptable salt, hydrate or solvate thereof, wherein:

the Ring A-Ring B portion is selected from the group consisting of

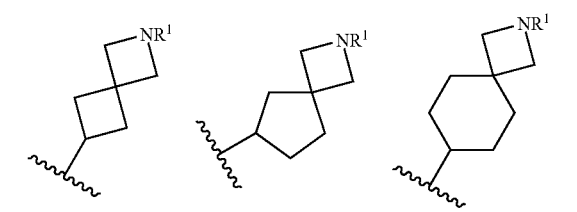

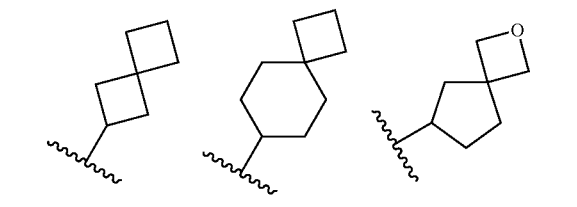

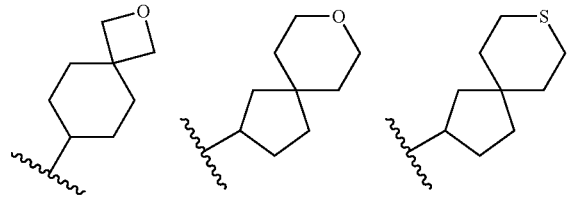

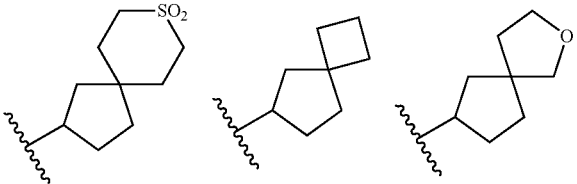

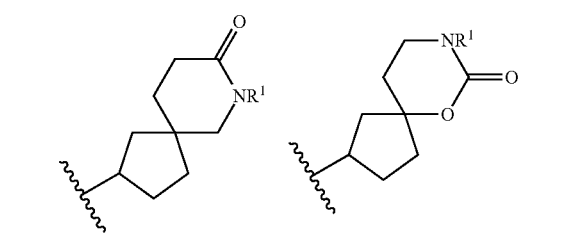

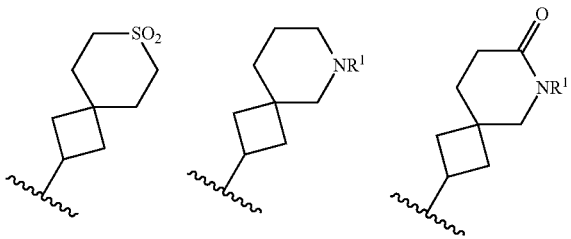

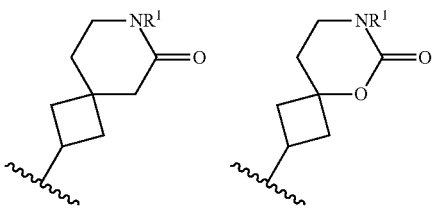

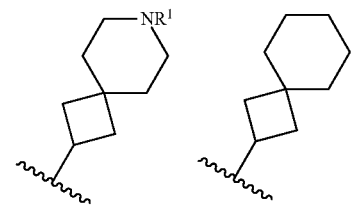

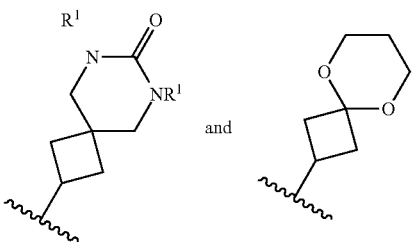

and each ring is unsubstituted or substituted by one or more $R^c$;

$R^1$ is independently chosen from hydrogen, $C_{1-12}$ alkyl, $C_{1-12}$ alkyl in which one carbon atom is replaced with Si, O, S atom, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —S(O)$_m$R$^4$, —SO$_2$NR$^4$R$^5$, —S(O)$_2$OR$^4$, —C(O)R$^4$, —NR$^4$C(O)R$^5$, —(CR$^6$R$^7$)$_n$C(O)OR$^4$, —(CR$^6$R$^7$)$_n$OR$^4$, —(CR$^6$R$^7$)$_n$C(O)NR$^4$R$^5$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, and wherein each hydrogen in $R^1$ is unsubstituted or substituted by $R^c$, or one of the hydrogen in $R^1$ is replaced with —P(O)(OR$^9$)$_2$—;

$R^c$ is independently chosen from halogen, $C_{1-12}$alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —NH$_2$, —CN, SF$_5$, —OH, —O—$C_{1-12}$alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic ring) or —O—(CH$_2$)$_n$(5-12 membered heteroaryl ring);

$R^2$ is selected from

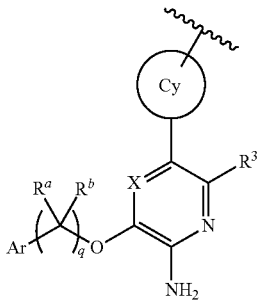

wherein:

X is N or $CR^{12}$;

Ar is $C_{6-12}$ aryl, 5-12 membered heteroaryl ring, $C_{3-12}$ cycloalkyl or 3-12 membered heteroalicyclic ring, and Ar is unsubstituted or substituted by one or more $R^c$ groups;

is selected from $C_{6-12}$ aryl, 5-12 membered heteroaryl ring, $C_{3-12}$ cycloalkyl or 3-12 membered heteroalicyclic ring, wherein

is unsubstituted or substituted by one, two or three $R^c$ groups;

$R^3$ is chosen from hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —S(O)$_m$R$^4$, —SO$_2$NR$^4$R$^5$, —S(O)$_2$OR$^4$, SF$_5$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, and each hydrogen in R$^3$ is unsubstituted or substituted by R$^8$;

R$^c$ is independently chosen from halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —S(O)$_m$R$^4$, —S(O)$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$OR$^4$, —(CR$^6$R$^7$)$_n$C(O)NR$^4$R$^5$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, and wherein each hydrogen in R$^c$ is unsubstituted or substituted by R$^8$, and wherein R$^c$ groups on adjacent atoms are uncombined or combine to form a $C_{6-12}$ aryl, 5-12 membered heteroaryl ring, $C_{3-12}$ cycloalkyl or 3-12 membered heteroalicyclic ring;

R$^4$, R$^5$, R$^6$ and R$^7$ are independently chosen from hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring;

or any two of R$^4$, R$^5$, R$^6$ and R$^7$ bound to the same nitrogen atom, together with the nitrogen to which they are bound, combine to form a 3 to 12 membered heteroalicyclic ring or a 5-12 membered heteroaryl ring or a 3 to 12 membered heteroalicyclic ring or a 5-12 membered heteroaryl ring containing 1 to 3 heteroatoms selected from N, O, and S;

or any two of R$^4$, R$^5$, R$^6$ and R$^7$ bound to the same carbon atom combine to form a $C_{3-12}$ cycloalkyl, $C_{6-12}$ aryl, 3-12 membered heteroalicyclic or 5-12 membered heteroaryl ring;

and each hydrogen in R$^4$, R$^5$, R$^6$ and R$^7$ is unsubstituted or substituted by R$^8$, or two hydrogen atoms on the same carbon atom in R$^4$, R$^5$, R$^6$ and R$^7$ is unsubstituted or are an oxo substituent;

R$^8$ is independently chosen from halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —NH$_2$, —CN, —OH, —O—C$_{1-12}$alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic ring) or —O—(CH$_2$)$_n$(5-12 membered heteroaryl ring); and each hydrogen in R$^8$ is unsubstituted or substituted by R$^{11}$;

R$^9$ is independently chosen from a $C_{1-12}$ alkyl, aryl, heteroaryl which is unsubstituted or substituted;

R$^{10}$ is independently chosen from a $C_{1-12}$ alkyl which is unsubstituted or substituted;

R$^{11}$ is independently chosen from halogen, $C_{1-12}$ alkyl, $C_{1-12}$ alkoxy, $C_{3-12}$ cycloalkyl, $C_{6-12}$ aryl, 3-12 membered heteroalicyclic ring, 5-12 membered heteroaryl ring, —O—C$_{1-12}$ alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heteroalicyclic ring), —O—(CH$_2$)$_n$(5-12 membered heteroaryl ring) or —CN, and each hydrogen in R$^{11}$ is unsubstituted or substituted by halogen, —OH, —CN, —C$_{1-12}$ alkyl which is unsubstituted, or partially halogenated or fully halogenated, —O—C$_{1-12}$ alkyl which is unsubstituted or partially halogenated or fully halogenated, or substituted with —CO;

R$^{12}$ is chosen from hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —S(O)$_m$R$^4$, —SO$_2$NR$^4$R$^5$, —S(O)$_2$OR$^4$, —NO$_2$, —NR$^4$R$^5$, —(CR$^6$R$^7$)$_n$OR$^4$, —CN, —C(O)R$^4$, —OC(O)R$^4$, —O(CR$^6$R$^7$)$_n$R$^4$, —NR$^4$C(O)R$^5$, —(CR$^6$R$^7$)$_n$C(O)OR$^4$, —(CR$^6$R$^7$)$_n$NCR$^4$R$^5$, —C(=NR$^6$)NR$^4$R$^5$, —NR$^4$C(O)NR$^5$R$^6$, —NR$^4$S(O)$_2$R$^5$ or —C(O)NR$^4$R$^5$, and each hydrogen in R$^{12}$ is unsubstituted or substituted by R$^3$;

R$^a$ and R$^b$ is independently chosen from hydrogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, —(CR$^6$R$^7$)$_n$OR$^4$, —CN, —C(O)R$^4$, —(CR$^6$R$^7$)$_n$C(O)OR$^4$, —(CR$^6$R$^7$)$_n$NCR$^4$R$^5$ or —C(O)NR$^4$R$^5$; and R$^a$ or R$^b$ are uncombined or together with the carbon to which they are attached to, R$^a$ or R$^b$ combine to form a 3-12 membered ring or a 3-12 membered ring which contains one or more heteroatom chosen from NR$^4$, O, S, Si; or R$^a$ and R$^b$ combine with a ring atom of Ar or a substituent of Ar to form a $C_{5-12}$ cycloalkyl, 5-12 membered heteroalicyclic ring fused to Ar; and each hydrogen in R$^a$ and R$^b$ is unsubstituted or substituted by R$^c$;

each m is independently 0, 1 or 2;

each n is independently 0, 1, 2, 3 or 4;

q is 1, 2, 3 or 4.

2. The method according to claim 1, wherein

is selected from

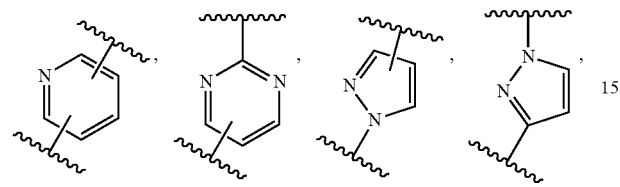

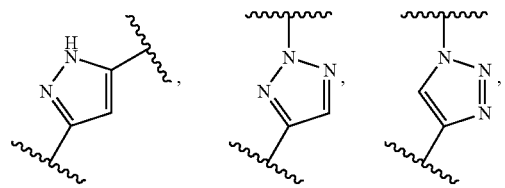

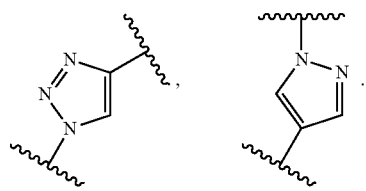

or an aryl, bicyclic aryl, bicyclic heteroaryl, unsubstituted or substituted by one, two or three $R^c$ groups.

3. The compound of claim 1, wherein said compound is selected from:

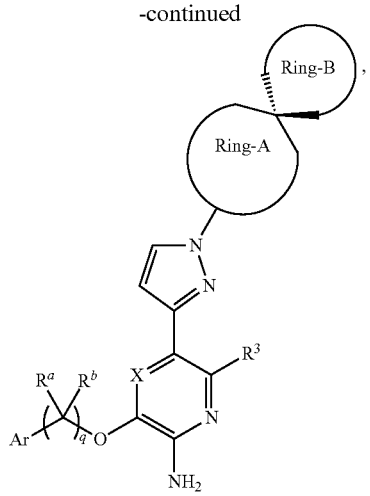

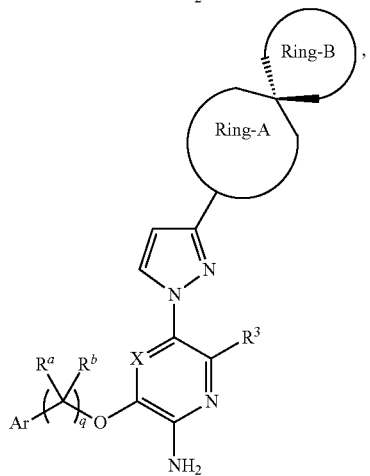

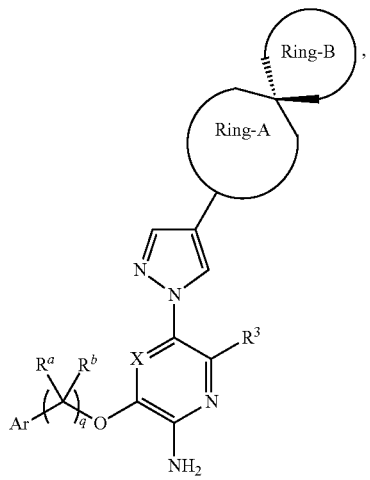

wherein:
$R^1$ is independently chosen from hydrogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, $-S(O)_m R^4$, $-SO_2 NR^4 R^5$, $-S(O)_2 OR^4$, $-C(O)R^4$, $-NR^4 C(O)R^5$, $-(CR^6 R^7)_n C(O)OR^4$, $-(CR^6 R^7)_n OR^4$, $-(CR^6 R^7)_n C(O)NR^4 R^5$, $-(CR^6 R^7)_n NCR^4 R^5$, $-C(=NR^6)NR^4 R^5$, $-NR^4 C(O)NR^5 R^6$, $-NR^4 S(O)_2 R^5$ or $-C(O)NR^4 R^5$, and wherein each hydrogen in $R^1$ is unsubstituted or substituted by $R^c$;

X is N or $CR^{12}$;

Ar is $C_{6-12}$ aryl, 5-12 membered heteroaryl ring, $C_{3-12}$ cycloalkyl or 3-12 membered heteroalicyclic ring, and wherein Ar is unsubstituted or substituted by one or more $R^c$ groups;

$R^3$ is chosen from hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, $-S(O)_mR^4$, $-SO_2NR^4R^5$, $-S(O)_2OR^4$, $SF_5$, $-NO_2$, $-NR^4R^5$, $-(CR^6R^7)_nOR^4$, $-CN$, $-C(O)R^4$, $-OC(O)R^4$, $-O(CR^6R^7)_nR^4$, $-NR^4C(O)R^5$, $-(CR^6R^7)_nC(O)OR^4$, $-(CR^6R^7)_nNCR^4R^5$, $-C(=NR^6)NR^4R^5$, $-NR^4C(O)NR^5R^6$, $-NR^4S(O)_2R^5$ or $-C(O)NR^4R^5$, and wherein each hydrogen in $R^3$ is unsubstituted or substituted by $R^8$;

$R^c$ is independently chosen from halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, $-S(O)_mR^4$, $-S(O)_2NR^4R^5$, $-S(O)_2OR^4$, $SF_5$, $-NO_2$, $-NR^4R^5$, $-(CR^6R^7)_nOR^4$, $-CN$, $-C(O)R^4$, $-OC(O)R^4$, $-O(CR^6R^7)_nR^4$, $-NR^4C(O)R^5$, $-(CR^6R^7)_nC(O)OR^4$, $-(CR^6R^7)_nOR^4$, $-(CR^6R^7)_nC(O)NR^4R^5$, $-(CR^6R^7)_nNCR^4R^5$, $-C(=NR^6)NR^4R^5$, $-NR^4C(O)NR^5R^6$, $-NR^4S(O)_2R^5$ or $-C(O)NR^4R^5$, and wherein each hydrogen in $R^c$ is unsubstituted or substituted by $R^8$, and wherein $R^c$ groups on adjacent atoms are uncombined or combine to form a $C_{6-12}$ aryl, 5-12 membered heteroaryl ring, $C_{3-12}$ cycloalkyl or 3-12 membered heteroalicyclic ring;

$R^4$, $R^5$, $R^6$ and $R^7$ is independently chosen from hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring; or any two of $R^4$, $R^5$, $R^6$ and $R^7$ bound to the same nitrogen atom, together with the nitrogen to which they are bound, combine to form a 3 to 12 membered heteroalicyclic ring or a 5-12 membered heteroaryl ring or a 3 to 12 membered heteroalicyclic ring or a 5-12 membered heteroaryl ring containing 1 to 3 heteroatoms selected from N, O, and S; or any two of $R^4$, $R^5$, $R^6$ and $R^7$ bound to the same carbon atom combine to form a $C_{3-12}$ cycloalkyl, $C_{6-12}$ aryl, 3-12 membered heteroalicyclic ring or 5-12 membered heteroaryl ring; and each hydrogen in $R^4$, $R^5$, $R^6$ and $R^7$ is unsubstituted or substituted by $R^8$, or two hydrogen atoms on the same carbon atom in $R^4$, $R^5$, $R^6$ and $R^7$ is unsubstituted or an oxo substituent;

$R^8$ is independently chosen from halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, $-NH_2$, $-CN$, $-OH$, $-O-C_{1-12}$alkyl, $-O-(CH_2)_nC_{3-12}$ cycloalkyl, $-O-(CH_2)_nC_{6-12}$ aryl, $-O-(CH_2)_n$(3-12 membered heteroalicyclic ring) or $-O-(CH_2)_n$(5-12 membered heteroaryl ring); and each hydrogen in $R^8$ is unsubstituted or substituted by $R^{11}$;

$R^{11}$ is independently chosen from halogen, $C_{1-12}$ alkyl, $C_{1-12}$ alkoxy, $C_{3-12}$ cycloalkyl, $C_{6-12}$ aryl, 3-12 membered heteroalicyclic ring, 5-12 membered heteroaryl ring, $-O-C_{1-12}$ alkyl, $-O-(CH_2)_nC_{3-12}$ cycloalkyl, $-O-(CH_2)_nC_{6-12}$ aryl, $-O-(CH_2)_n$(3-12 membered heteroalicyclic ring), $-O-(CH_2)_n$(5-12 membered heteroaryl ring) or $-CN$, and each hydrogen in $R^{11}$ is unsubstituted or substituted by halogen, $-OH$, $-CN$, $-C_{1-12}$ alkyl which is unsubstituted or partially halogenated or fully halogenated, $-O-C_{1-12}$ alkyl which is unsubstituted or partially halogenated or fully halogenated, or substituted with $-CO$;

$R^{12}$ is chosen from hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, $-S(O)_mR^4$, $-SO_2NR^4R^5$, $-S(O)_2OR^4$, $-NO_2$, $-NR^4R^5$, $-(CR^6R^7)_nOR^4$, $-CN$, $-C(O)R^4$, $-OC(O)R^4$, $-O(CR^6R^7)_nR^4$, $-NR^4C(O)R^5$, $-(CR^6R^7)_nC(O)OR^4$, $-(CR^6R^7)_nNCR^4R^5$, $-C(=NR^6)NR^4R^5$, $-NR^4C(O)NR^5R^6$, $-NR^4S(O)_2R^5$ or $-C(O)NR^4R^5$, and each hydrogen in $R^{12}$ is unsubstituted or substituted by $R^3$;

$R^a$ and $R^b$ is independently chosen from hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic ring, 5-12 membered heteroaryl ring, $-S(O)_mR^4$, $-SO_2NR^4R^5$, $-S(O)_2OR^4$, $-NO_2$, $-NR^4R^5$, $-(CR^6R^7)_nOR^4$, $-CN$, $-C(O)R^4$, $-OC(O)R^4$, $-NR^4C(O)R^5$, $-(CR^6R^7)_nC(O)OR^4$, $-(CR^6R^7)_nNCR^4R^5$, $-NR^4C(O)NR^5R^6$, $-NR^4S(O)_2R^5$ or $-C(O)NR^4R^5$; or together with the carbon to which they are attached to, $R^a$ or $R^b$ combine to form a 3-12 membered ring which may contains one or more heteroatom chosen from $NR^4$, O, S, Si, or $R^a$ and $R^b$ combine with a ring atom of A or a substituent of A to form a $C_{3-12}$ cycloalkyl, a 3-12 membered heteroalicyclic ring, $C_{6-12}$ aryl or a 5-12 membered heteroaryl ring fused to A; and each hydrogen in $R^a$ and $R^b$ is unsubstituted or substituted by $R^c$;

each m is independently 0, 1 or 2;

each n is independently 0, 1, 2, 3 or 4;

q is 1, 2, 3 or 4;

or a pharmaceutically acceptable salt, hydrate or solvate thereof.

4. The compound of claim 3, wherein said compound is selected from:

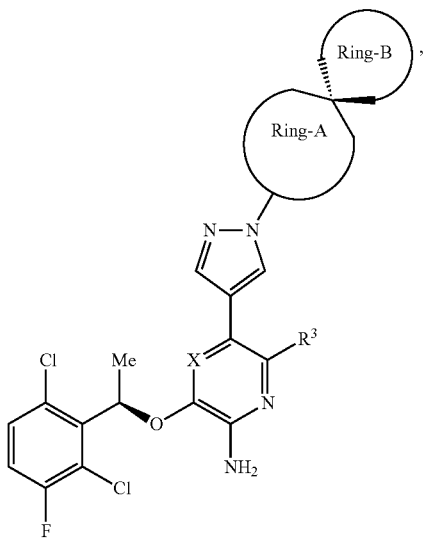

-continued
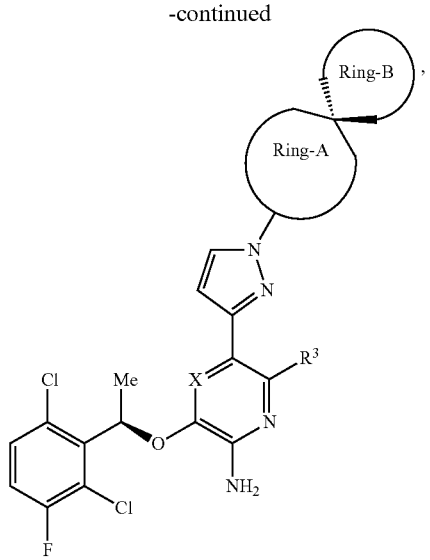
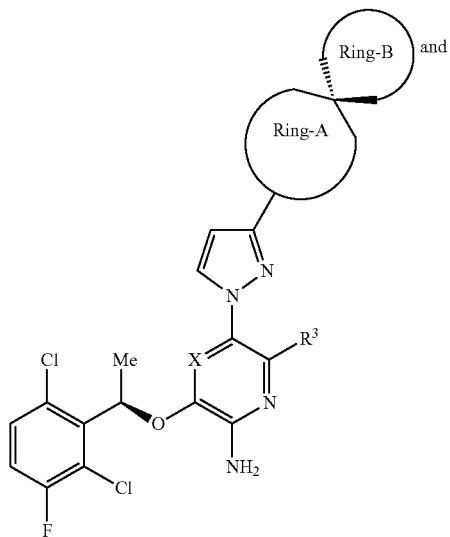
5. The compound of claim 4, wherein said compound has the formula:
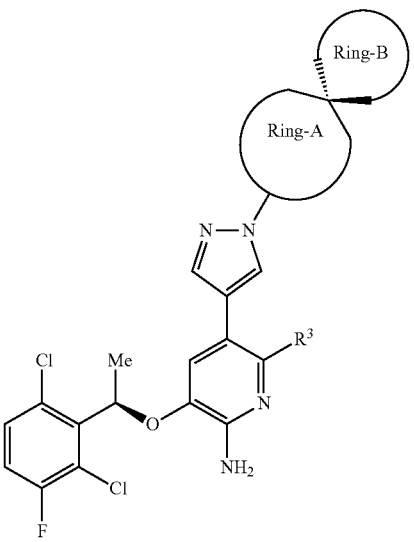
6. The compound according to claim 1, wherein
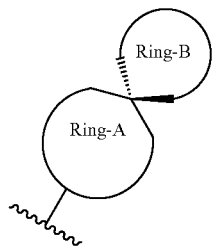
is selected from the group consisting of:
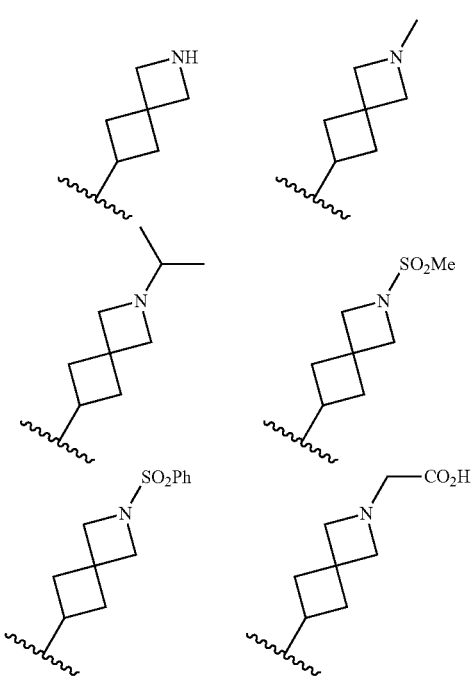

83
-continued
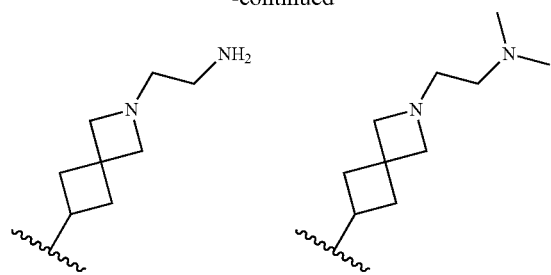
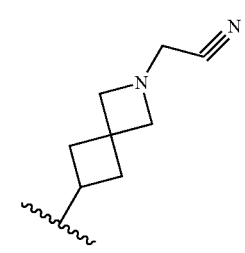
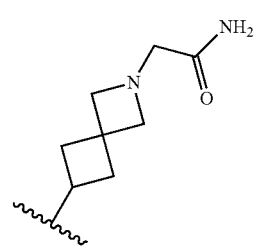
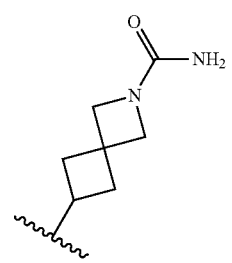
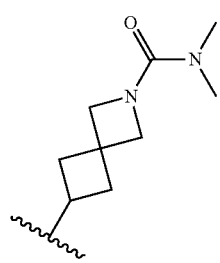
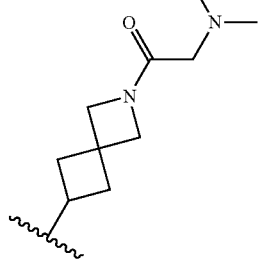
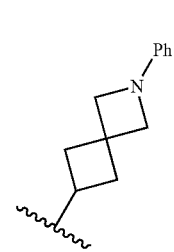
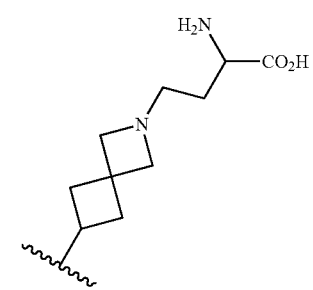
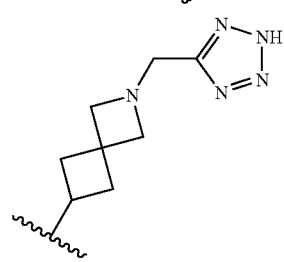
84
-continued
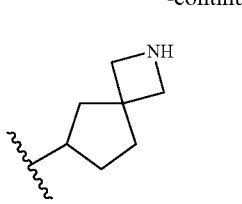
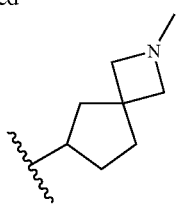
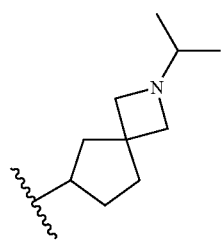
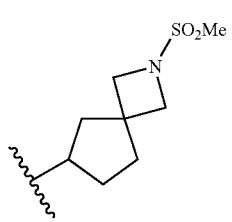
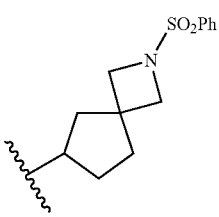
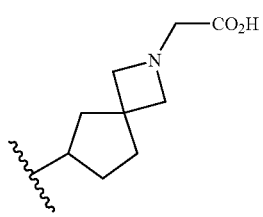
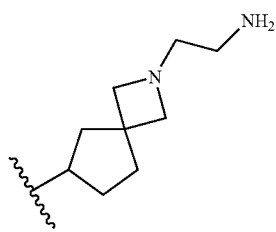
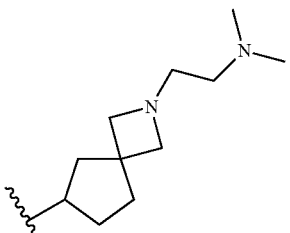
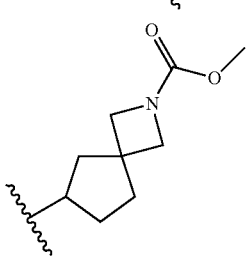
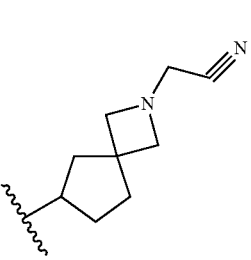
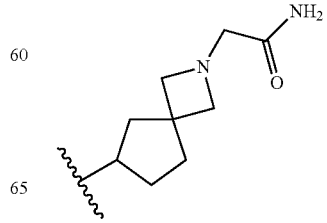
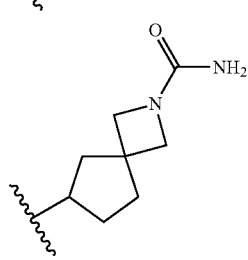

85
-continued
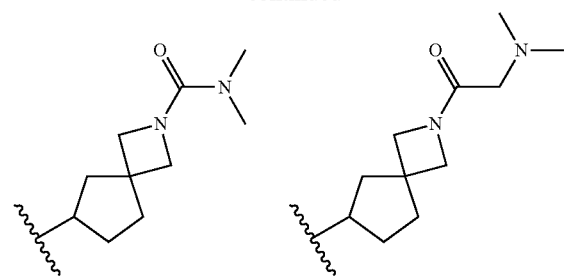
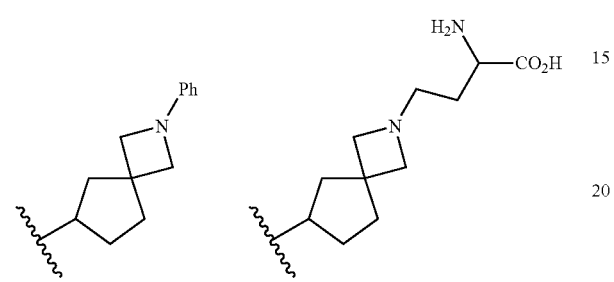
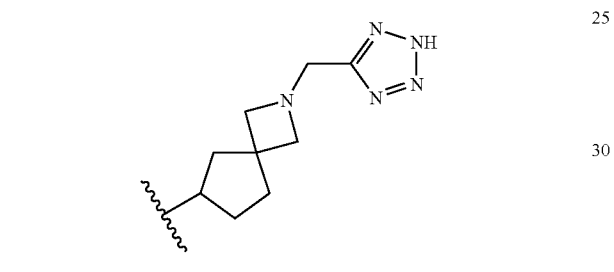
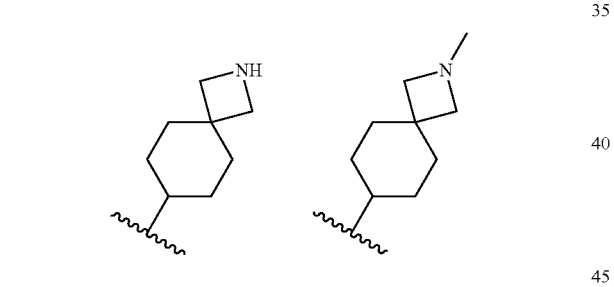
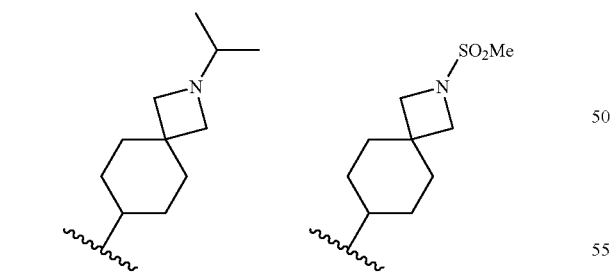
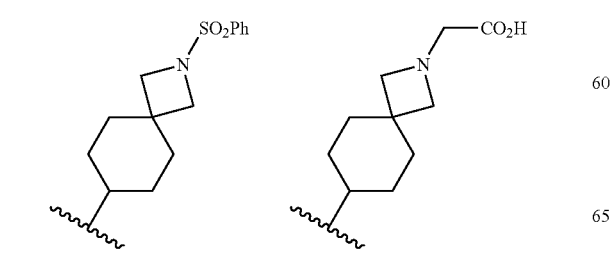
86
-continued
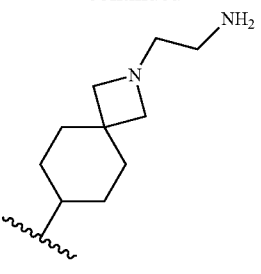
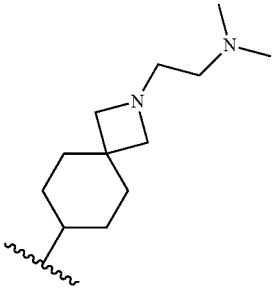
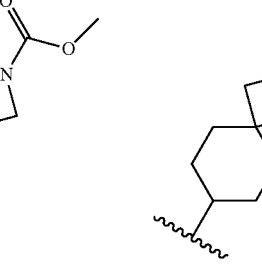
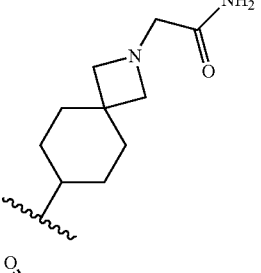
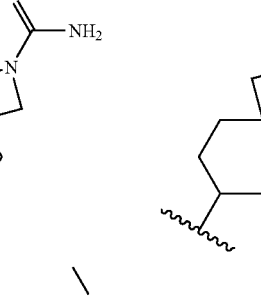
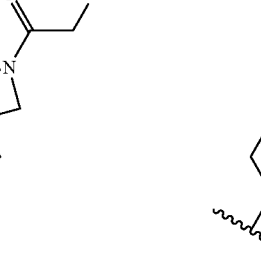

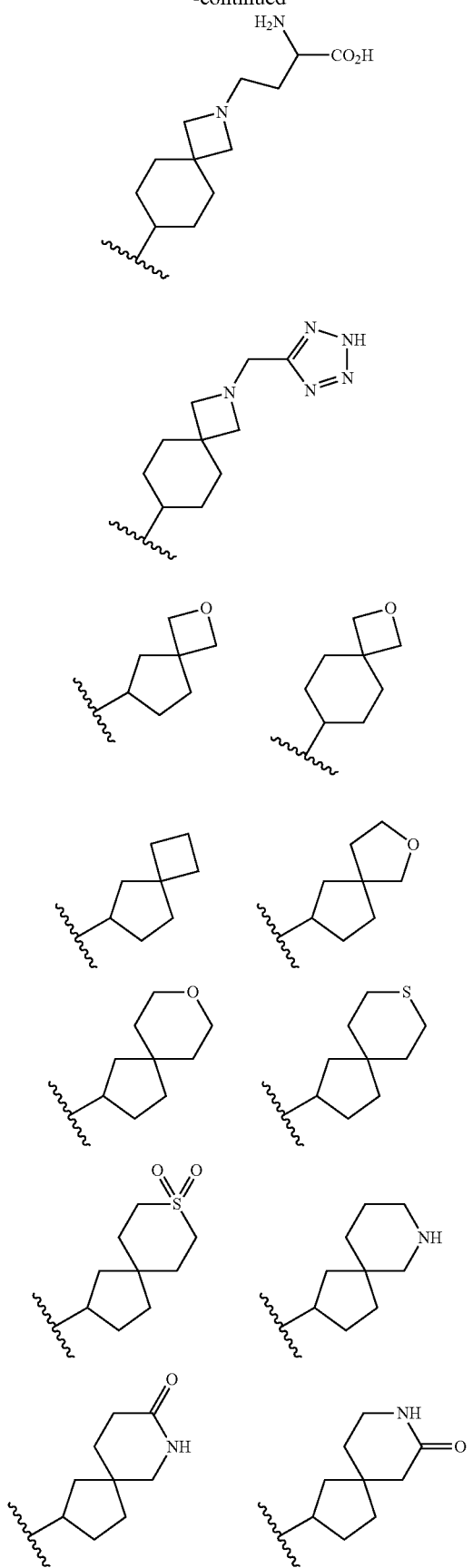
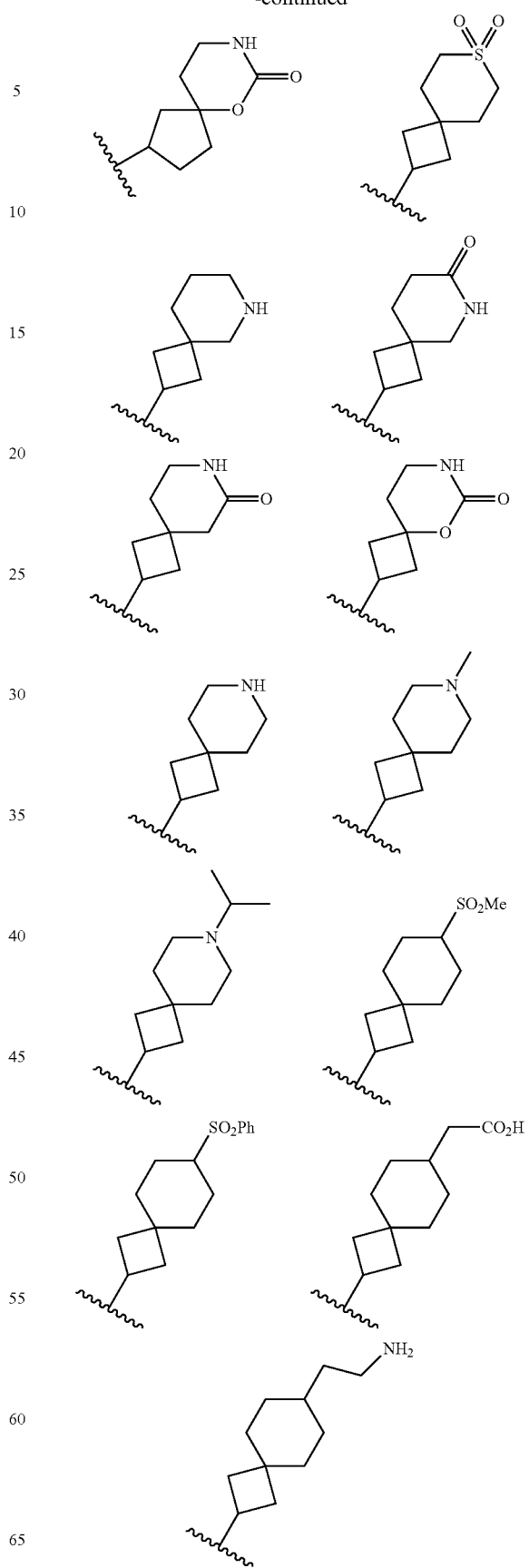

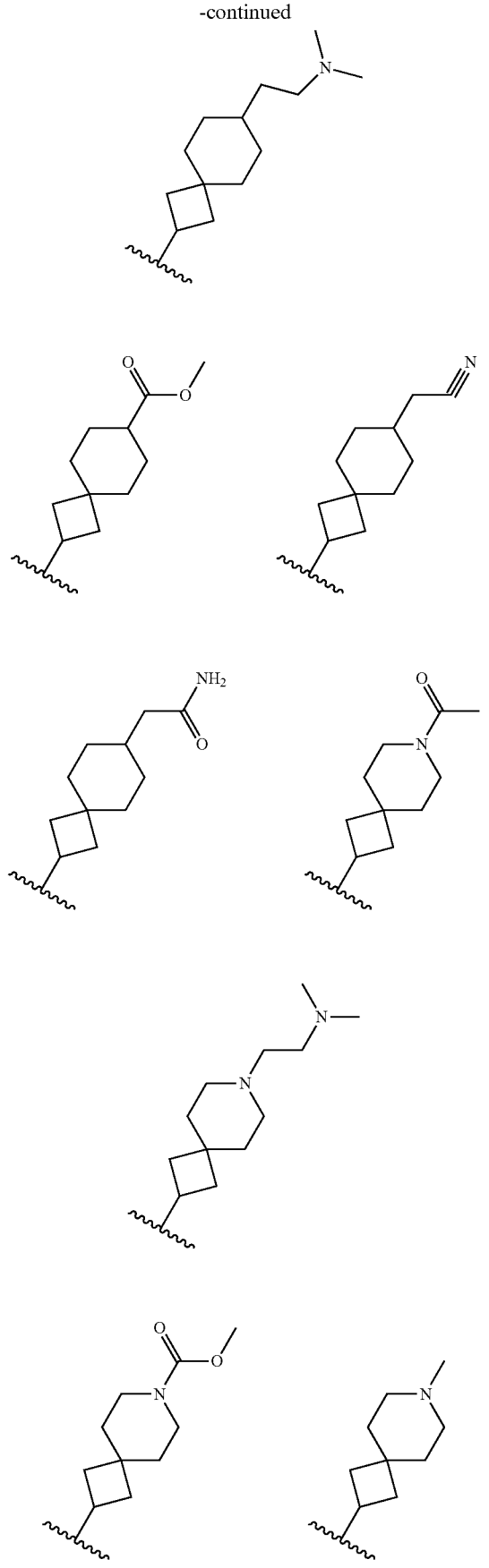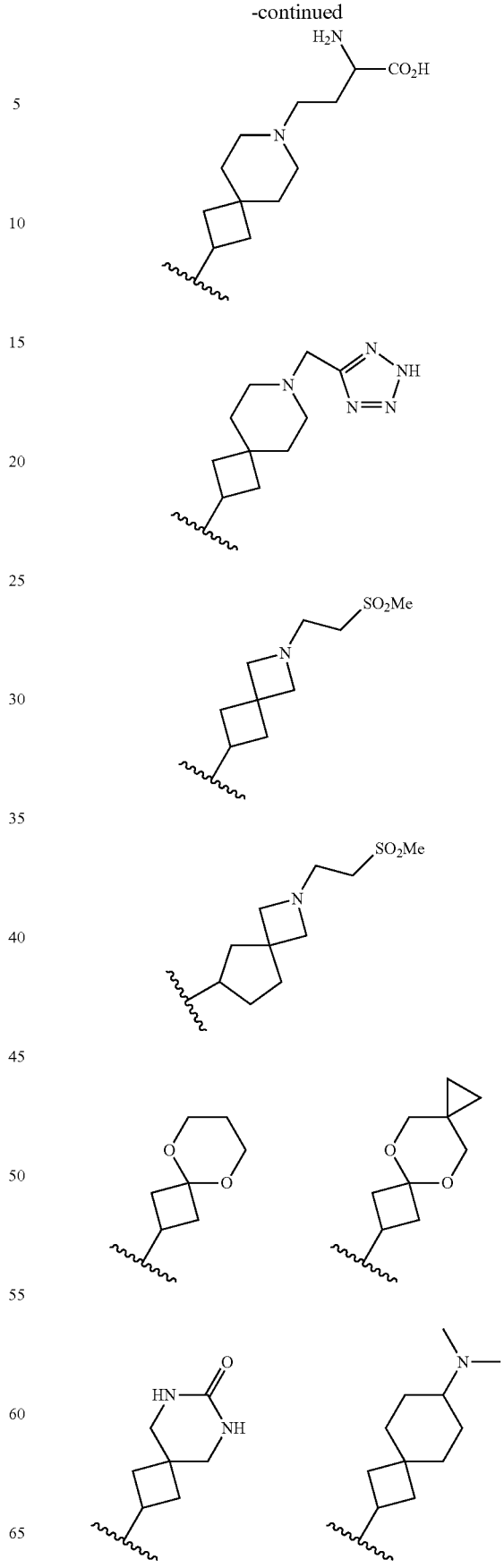

-continued

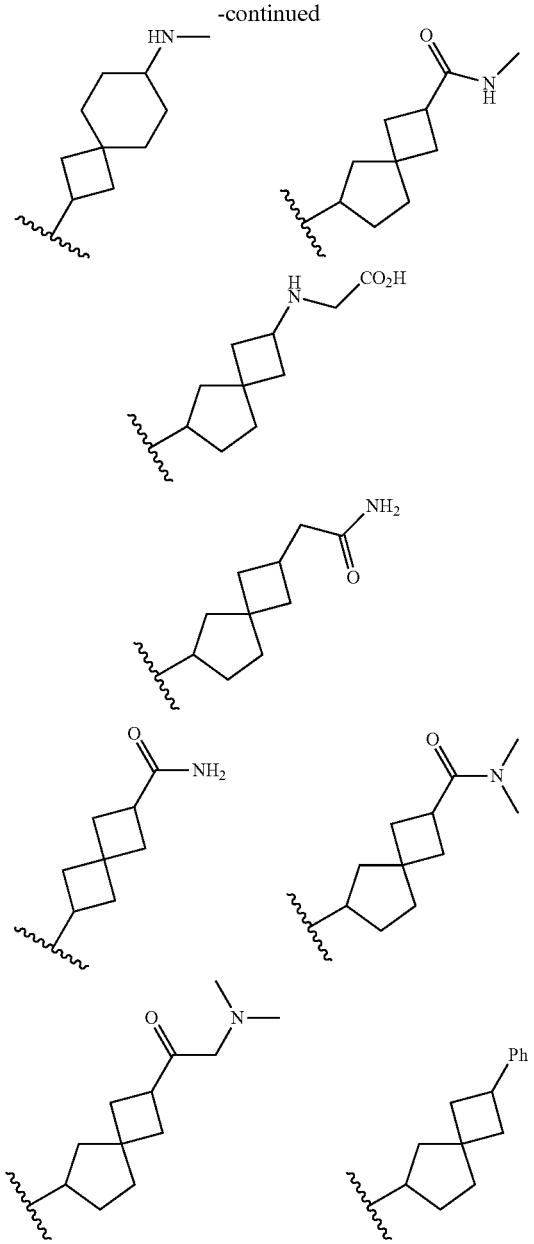

-continued

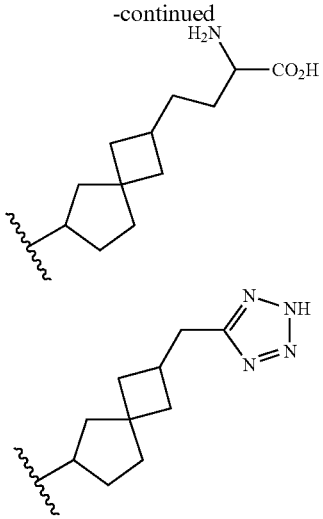

7. The compounds of claim 5, wherein said compounds are:
(±)-5-(1-(2-azaspiro[3.3]heptan-6-yl)-1H-pyrazol-4-yl)-3-((R)-1-(2,6-dichloro-3-fluorophenyl)ethoxy)pyridin-2-amine;
(R)-5-(1-(2-azaspiro[3.3]heptan-6-yl)-1H-pyrazol-4-yl)-3-((R)-1-(2,6-dichloro-3-fluorophenyl)ethoxy)pyridin-2-amine;
(R)-5-(1-(7-azaspiro[3.5]nonan-2-yl)-1H-pyrazol-4-yl)-3-((R)-1-(2,6-dichloro-3-fluorophenyl)ethoxy)pyridin-2-amine;
(R)-5-(1-(2-azaspiro[3.5]nonan-7-yl)-1H-pyrazol-4-yl)-3-((R)-1-(2,6-dichloro-3-fluorophenyl)ethoxy)pyridin-2-amine; and
(R)-5-(1-(6-azaspiro[3.5]nonan-2-yl)-1H-pyrazol-4-yl)-3-(1-(2,6-dichloro-3-fluorophenyl)ethoxy)pyridin-2-amine.

8. A composition comprising a combination of a compound of claim 1 and an additional anti-cancer agent.

9. A method treating a cancer in a patient in need thereof by administering to said patient a therapeutically effective amount of a compound of claim 1, or the composition of claim 8, wherein said cancer is selected from the group consisting of breast cancer, liver cancer, non-small-cell lung cancer, prostate cancer, and renal cell cancer.

10. The method of claim 9, further comprising administering radiotherapy.

* * * * *